United States Patent
Chataigner et al.

(10) Patent No.: US 9,877,842 B2
(45) Date of Patent: Jan. 30, 2018

(54) ANCHORING DEVICE FOR A SPINAL IMPLANT, SPINAL IMPLANT AND IMPLANTATION INSTRUMENTATION

(71) Applicant: LDR Medical, Rosières Près Troyes (FR)

(72) Inventors: Hervé Chataigner, Boussieres (FR); Craig Chebuhar, Marietta, GA (US); Pierre Bernard, Bordeaux (FR); Hervé Dinville, St-Parres-aux-Tertres (FR); Emmanuel Bougere, Bordeaux (FR)

(73) Assignee: LDR Medical, Sainte-Savine (FR)

( * ) Notice: Subject to any disclaimer, the term of this patent is extended or adjusted under 35 U.S.C. 154(b) by 489 days.

(21) Appl. No.: 14/252,852

(22) Filed: Apr. 15, 2014

(65) Prior Publication Data
US 2015/0209089 A1 Jul. 30, 2015

(30) Foreign Application Priority Data

Jan. 30, 2014 (FR) .................................... 14 50749

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4425* (2013.01);
(Continued)

(58) Field of Classification Search
CPC ...... A61F 2/4455; A61F 2/446; A61F 2/4465; A61F 2/447; A61F 2002/30331; A61F 2002/30841; A61F 2002/4475
See application file for complete search history.

(56) References Cited

U.S. PATENT DOCUMENTS 344,683 A 6/1886 Sherer
1,025,596 A 5/1912 Strawser
(Continued)

FOREIGN PATENT DOCUMENTS

FR 2891135 3/2007
RU 2004218 12/1993
(Continued)

OTHER PUBLICATIONS

Apparatus and Method for Fusing Opposing Spinal Vertebrae, Bramlet, Dale G. et al., U.S. Appl. No. 09/635,436, filed Aug. 11, 2000.
(Continued)

*Primary Examiner* — Christian Sevilla
*Assistant Examiner* — Eric S Gibson
(74) *Attorney, Agent, or Firm* — Lauff Law PLLC

(57) ABSTRACT

Anchoring devices for rachidian implants, implants, surgical instruments, and surgical systems and methods are disclosed. In some embodiments, an anchor comprises a stiff plate with a longitudinal axis, configured for penetration of its anterior end into a vertebral surface while its posterior end remains engaged with the implant. An implant may include a locking mechanism for the anchor. An anchor may include an abutment configured to abut a complementary abutment of an implant. In some configurations, inserting an anchor in a passage of an implant may displace a locking mechanism, which may resile and lock the anchor in the implant with complementary abutments of the anchor and implant abutting.

20 Claims, 26 Drawing Sheets

(52) U.S. Cl.
CPC .......... *A61F 2/4611* (2013.01); *A61F 2/4637* (2013.01); *A61F 2002/305* (2013.01); *A61F 2002/30135* (2013.01); *A61F 2002/30136* (2013.01); *A61F 2002/30161* (2013.01); *A61F 2002/30331* (2013.01); *A61F 2002/30373* (2013.01); *A61F 2002/30401* (2013.01); *A61F 2002/30476* (2013.01); *A61F 2002/30492* (2013.01); *A61F 2002/30517* (2013.01); *A61F 2002/30579* (2013.01); *A61F 2002/30604* (2013.01); *A61F 2002/30772* (2013.01); *A61F 2002/30782* (2013.01); *A61F 2002/30841* (2013.01); *A61F 2002/30879* (2013.01); *A61F 2002/30889* (2013.01); *A61F 2002/30904* (2013.01); *A61F 2002/4641* (2013.01); *A61F 2002/4642* (2013.01)

(56) References Cited

U.S. PATENT DOCUMENTS

| | | |
|---|---|---|
| 1,121,484 A | 12/1914 | Crites |
| 4,135,506 A | 1/1979 | Ulrich |
| 4,790,303 A | 12/1988 | Steffee |
| 4,892,545 A | 1/1990 | Day et al. |
| 4,904,261 A | 2/1990 | Dove et al. |
| 5,397,364 A | 3/1995 | Kozak et al. |
| 5,425,772 A | 6/1995 | Brantigan |
| 5,443,514 A | 8/1995 | Steffee |
| 5,522,845 A | 6/1996 | Wenstrom, Jr. |
| 5,522,899 A | 6/1996 | Michelson |
| 5,554,191 A | 9/1996 | Lahille et al. |
| 5,571,109 A | 11/1996 | Bertagnoli |
| 5,609,635 A | 3/1997 | Michelson |
| 5,713,899 A | 2/1998 | Marnay et al. |
| 5,776,199 A | 7/1998 | Michelson |
| 5,782,919 A | 7/1998 | Zdeblick et al. |
| 5,800,547 A | 9/1998 | Schafer et al. |
| 5,849,004 A | 12/1998 | Bramlet |
| 6,059,787 A | 5/2000 | Allen |
| 6,066,175 A | 5/2000 | Henderson et al. |
| 6,099,531 A | 8/2000 | Bonutti |
| 6,102,950 A | 8/2000 | Vaccaro |
| 6,143,032 A | 11/2000 | Schafer et al. |
| 6,174,311 B1 | 1/2001 | Branch et al. |
| 6,179,873 B1 | 1/2001 | Zientek |
| 6,179,875 B1 | 1/2001 | Von Strempel |
| 6,206,923 B1 | 3/2001 | Boyd et al. |
| 6,235,059 B1 | 5/2001 | Benezech et al. |
| 6,241,769 B1 | 6/2001 | Nicholson et al. |
| 6,302,914 B1 | 10/2001 | Michelson |
| 6,342,074 B1 | 1/2002 | Simpson |
| 6,371,987 B1 | 4/2002 | Weiland et al. |
| 6,419,703 B1 | 7/2002 | Fallin et al. |
| 6,423,063 B1 | 7/2002 | Bonutti |
| 6,447,544 B1 | 9/2002 | Michelson |
| 6,447,546 B1 | 9/2002 | Bramlet et al. |
| 6,447,547 B1 | 9/2002 | Michelson |
| 6,471,724 B2 | 10/2002 | Zdeblick et al. |
| 6,478,823 B1 | 11/2002 | Michelson |
| 6,482,233 B1 | 11/2002 | Aebi et al. |
| 6,485,517 B1 | 11/2002 | Michelson |
| 6,500,205 B1 | 12/2002 | Michelson |
| 6,540,753 B2 | 4/2003 | Cohen |
| 6,558,423 B1 | 5/2003 | Michelson |
| 6,565,605 B2 | 5/2003 | Goble et al. |
| 6,607,530 B1 | 8/2003 | Carl et al. |
| 6,635,086 B2 | 10/2003 | Lin |
| 6,648,893 B2 | 11/2003 | Dudasik |
| 6,706,067 B2 | 3/2004 | Shimp et al. |
| 6,709,458 B2 | 3/2004 | Michelson |
| 6,716,247 B2 | 4/2004 | Michelson |
| 6,723,128 B2 | 4/2004 | Uk |
| 6,733,535 B2 | 5/2004 | Michelson |
| 6,749,636 B2 | 6/2004 | Michelson |
| 6,767,367 B1 | 7/2004 | Michelson |
| 6,770,096 B2 | 8/2004 | Bolger et al. |
| 6,793,679 B2 | 9/2004 | Michelson |
| 6,805,714 B2 | 10/2004 | Sutcliffe |
| 6,808,537 B2 | 10/2004 | Michelson |
| 6,835,206 B2 | 12/2004 | Jackson |
| 6,849,093 B2 | 2/2005 | Michelson |
| 6,890,355 B2 | 5/2005 | Michelson |
| 6,902,580 B2 | 6/2005 | Fallin et al. |
| 6,923,811 B1 | 8/2005 | Carl et al. |
| 6,923,830 B2 | 8/2005 | Michelson |
| 6,955,691 B2 | 10/2005 | Chae et al. |
| 6,962,606 B2 | 11/2005 | Michelson |
| 6,964,687 B1 | 11/2005 | Bernard et al. |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 7,001,385 B2 | 2/2006 | Bonutti |
| 7,008,453 B1 | 3/2006 | Michelson |
| 7,018,412 B2 | 3/2006 | Ferreira et al. |
| 7,033,394 B2 | 4/2006 | Michelson |
| 7,041,135 B2 | 5/2006 | Michelson |
| 7,041,136 B2 | 5/2006 | Goble et al. |
| 7,060,097 B2 | 6/2006 | Fraser et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,112,206 B2 | 9/2006 | Michelson |
| 7,118,579 B2 | 10/2006 | Michelson |
| 7,118,598 B2 | 10/2006 | Michelson |
| 7,128,760 B2 | 10/2006 | Michelson |
| 7,128,761 B2 | 10/2006 | Kuras et al. |
| 7,163,561 B2 | 1/2007 | Michelson |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,223,289 B2 | 5/2007 | Trieu et al. |
| 7,232,463 B2 | 6/2007 | Falahee |
| 7,232,464 B2 | 6/2007 | Mathieu et al. |
| 7,235,082 B2 | 6/2007 | Bartish et al. |
| 7,238,205 B2 | 7/2007 | Karahalios |
| 7,291,170 B2 | 11/2007 | Huppert |
| 7,326,248 B2 | 2/2008 | Michelson |
| 7,361,196 B2 | 4/2008 | Fallin et al. |
| 7,410,501 B2 | 8/2008 | Michelson |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,636 B2 | 11/2008 | Michelson |
| 7,455,692 B2 | 11/2008 | Michelson |
| 7,465,317 B2 | 12/2008 | Malberg et al. |
| 7,479,160 B2 | 1/2009 | Branch et al. |
| 7,503,933 B2 | 3/2009 | Michelson |
| 7,540,882 B2 | 6/2009 | Michelson |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,608,107 B2 | 10/2009 | Michelson |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,637,951 B2 | 12/2009 | Michelson |
| 7,637,953 B2 | 12/2009 | Branch et al. |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |

(56) References Cited

U.S. PATENT DOCUMENTS

| | | |
|---|---|---|
| 7,695,517 B2 | 4/2010 | Benzel et al. |
| 7,727,280 B2 | 6/2010 | McLuen |
| 7,744,602 B2 | 6/2010 | Teeny et al. |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,905,886 B1 | 3/2011 | Curran et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | McLuen |
| 8,216,312 B2 | 7/2012 | Gray |
| 8,241,359 B2 | 8/2012 | Davis et al. |
| 8,267,999 B2 | 9/2012 | Beaurain et al. |
| 8,313,528 B1* | 11/2012 | Wensel ............ A61F 2/447 623/17.11 |
| 8,333,804 B1 | 12/2012 | Wensel |
| 8,343,219 B2* | 1/2013 | Allain ............ A61B 17/0642 606/100 |
| 8,349,015 B2 | 1/2013 | Bae et al. |
| 8,382,839 B1* | 2/2013 | Wensel ............ A61B 17/864 623/17.11 |
| 8,460,388 B2* | 6/2013 | Kirwan ............ A61F 2/4455 623/17.11 |
| 8,696,681 B2 | 4/2014 | Harris et al. |
| 8,968,405 B2* | 3/2015 | Kirwan ............ A61F 2/4455 623/17.11 |
| 9,039,774 B2* | 5/2015 | Chataigner ............ A61F 2/442 606/86 A |
| 9,044,337 B2* | 6/2015 | Dinville ............ A61F 2/447 |
| 9,078,765 B2 | 7/2015 | Louis et al. |
| 9,173,683 B2* | 11/2015 | Hawkins ............ A61B 17/0401 |
| 9,173,745 B2* | 11/2015 | Dinville ............ A61F 2/447 |
| 9,463,091 B2* | 10/2016 | Brett ............ A61F 2/442 |
| 9,517,144 B2* | 12/2016 | McAtamney ............ A61F 2/4455 |
| 2002/0016592 A1 | 2/2002 | Branch et al. |
| 2002/0026243 A1 | 2/2002 | Lin |
| 2002/0040243 A1 | 4/2002 | Attali et al. |
| 2002/0161444 A1 | 10/2002 | Choi |
| 2002/0165612 A1 | 11/2002 | Gerber et al. |
| 2002/0165613 A1 | 11/2002 | Lin et al. |
| 2002/0193880 A1 | 12/2002 | Fraser |
| 2003/0028249 A1 | 2/2003 | Baccelli et al. |
| 2003/0069640 A1 | 4/2003 | Ferreira et al. |
| 2003/0074075 A1 | 4/2003 | Thomas, Jr. et al. |
| 2003/0100950 A1 | 5/2003 | Moret |
| 2003/0135279 A1 | 7/2003 | Michelson |
| 2003/0149438 A1 | 8/2003 | Nichols et al. |
| 2003/0187436 A1 | 10/2003 | Bolger et al. |
| 2003/0195514 A1 | 10/2003 | Trieu et al. |
| 2003/0195626 A1 | 10/2003 | Huppert |
| 2004/0010312 A1 | 1/2004 | Enayati |
| 2004/0030387 A1 | 2/2004 | Landry et al. |
| 2004/0093083 A1 | 5/2004 | Branch et al. |
| 2004/0127990 A1 | 7/2004 | Bartish, Jr. et al. |
| 2004/0199254 A1 | 10/2004 | Louis et al. |
| 2004/0210219 A1 | 10/2004 | Bray |
| 2004/0210227 A1 | 10/2004 | Trail et al. |
| 2004/0210313 A1 | 10/2004 | Michelson |
| 2004/0254643 A1 | 12/2004 | Jackson |
| 2005/0015149 A1 | 1/2005 | Michelson |
| 2005/0027360 A1 | 2/2005 | Webb et al. |
| 2005/0038512 A1 | 2/2005 | Michelson |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0096745 A1 | 5/2005 | Andre et al. |
| 2005/0119747 A1 | 6/2005 | Monterumici et al. |
| 2005/0143733 A1 | 6/2005 | Petit |
| 2005/0143825 A1 | 6/2005 | Enayati |
| 2005/0177236 A1 | 8/2005 | Mathieu et al. |
| 2005/0288788 A1 | 12/2005 | Dougherty-Shah |
| 2006/0058878 A1 | 3/2006 | Michelson |
| 2006/0085076 A1 | 4/2006 | Krishna et al. |
| 2006/0089717 A1 | 4/2006 | Krishna et al. |
| 2006/0095136 A1 | 5/2006 | McLuen |
| 2006/0121084 A1 | 6/2006 | Borden et al. |
| 2006/0122703 A1 | 6/2006 | Aebi et al. |
| 2006/0129244 A1 | 6/2006 | Ensign |
| 2006/0136063 A1* | 6/2006 | Zeegers ............ A61B 17/0642 623/17.14 |
| 2006/0206208 A1 | 9/2006 | Michelson |
| 2006/0235426 A1 | 10/2006 | Lim et al. |
| 2006/0241761 A1 | 10/2006 | Gately |
| 2006/0241764 A1 | 10/2006 | Michelson |
| 2006/0253201 A1 | 11/2006 | McLuen |
| 2007/0016297 A1 | 1/2007 | Johnson |
| 2007/0032871 A1 | 2/2007 | Michelson |
| 2007/0073404 A1 | 3/2007 | Rashbaum et al. |
| 2007/0093850 A1 | 4/2007 | Harris et al. |
| 2007/0142843 A1 | 6/2007 | Dye |
| 2007/0162128 A1 | 7/2007 | DeRidder et al. |

(56) References Cited

U.S. PATENT DOCUMENTS

| | | |
|---|---|---|
| 2007/0179623 A1 | 8/2007 | Trieu et al. |
| 2007/0233253 A1 | 10/2007 | Bray et al. |
| 2007/0250167 A1 | 10/2007 | Bray et al. |
| 2007/0260249 A1 | 11/2007 | Boyajian et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0027547 A1 | 1/2008 | Yu et al. |
| 2008/0027550 A1 | 1/2008 | Link et al. |
| 2008/0033562 A1 | 2/2008 | Krishna et al. |
| 2008/0125865 A1 | 5/2008 | Abdelgany |
| 2008/0161933 A1 | 7/2008 | Grotz et al. |
| 2008/0195211 A1 | 8/2008 | Lin et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0054988 A1 | 2/2009 | Hess |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1* | 4/2009 | Allain .................. A61B 17/0642 623/17.16 |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0222100 A1 | 9/2009 | Cipoletti et al. |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1* | 7/2010 | Kirwan .................. A61F 2/4455 623/17.11 |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1* | 9/2011 | Donner .................. A61B 17/70 623/17.16 |
| 2011/0264227 A1 | 10/2011 | Boyajian et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0078371 A1 | 3/2012 | Gamache et al. |
| 2012/0078373 A1* | 3/2012 | Gamache ............ A61B 17/8625 623/17.16 |
| 2012/0116466 A1* | 5/2012 | Dinville .................. A61F 2/447 606/86 A |
| 2012/0232599 A1* | 9/2012 | Schoenly ............ A61B 17/8635 606/315 |
| 2013/0053891 A1* | 2/2013 | Hawkins ............ A61B 17/0401 606/264 |
| 2013/0110242 A1* | 5/2013 | Kirwan .................. A61F 2/4465 623/17.16 |
| 2013/0123926 A1 | 5/2013 | Bae et al. |
| 2013/0150968 A1* | 6/2013 | Dinville .................. A61F 2/447 623/17.16 |
| 2013/0166029 A1* | 6/2013 | Dinville .................. A61F 2/447 623/17.16 |
| 2013/0226300 A1* | 8/2013 | Chataigner ............ A61F 2/442 623/17.16 |
| 2014/0052260 A1* | 2/2014 | McKenny ................ A61F 2/442 623/17.16 |
| 2014/0100662 A1* | 4/2014 | Patterson ............ A61F 2/4455 623/17.16 |
| 2014/0114413 A1* | 4/2014 | Allain .................. A61B 17/0642 623/17.16 |
| 2014/0180417 A1* | 6/2014 | Bergey .................. A61F 2/4455 623/17.16 |
| 2014/0336771 A1 | 11/2014 | Zambiasi et al. |
| 2015/0045893 A1* | 2/2015 | Dinville .................... A61F 2/44 623/17.16 |
| 2015/0051702 A1* | 2/2015 | Chataigner ............ A61F 2/442 623/17.16 |
| 2015/0127107 A1 | 5/2015 | Kim et al. |
| 2015/0196343 A1 | 7/2015 | Donald et al. |
| 2015/0209089 A1* | 7/2015 | Chataigner ........ A61B 17/7064 623/17.16 |
| 2015/0250605 A1* | 9/2015 | Chataigner ............ A61F 2/442 623/17.16 |
| 2015/0257896 A1* | 9/2015 | Dinville .................. A61F 2/447 623/17.16 |

(56) References Cited

U.S. PATENT DOCUMENTS

| | | | | |
|---|---|---|---|---|
| 2015/0305887 | A1* | 10/2015 | McAtamney | A61F 2/4455 623/17.16 |
| 2015/0320568 | A1* | 11/2015 | Ameil | A61F 2/447 623/17.13 |
| 2016/0008033 | A1* | 1/2016 | Hawkins | A61B 17/0401 606/265 |
| 2016/0051380 | A1* | 2/2016 | Dinville | A61F 2/447 606/99 |
| 2016/0058563 | A1* | 3/2016 | Zappacosta | A61B 17/0642 623/17.16 |
| 2016/0058564 | A1* | 3/2016 | Zappacosta | A61F 2/4455 623/17.16 |
| 2016/0058565 | A1* | 3/2016 | Zappacosta | A61F 2/4455 623/17.16 |
| 2016/0100953 | A1* | 4/2016 | Dinville | A61F 2/44 623/17.16 |
| 2016/0338849 | A1* | 11/2016 | Ashleigh | A61F 2/4455 |
| 2016/0338850 | A1* | 11/2016 | Ashleigh | A61F 2/4455 |

FOREIGN PATENT DOCUMENTS

| | | | | |
|---|---|---|---|---|
| WO | WO2008149223 | | 12/2008 | |
| WO | WO2010121028 | | 10/2010 | |
| WO | WO 2011/080535 | A1 * | 7/2011 | A61F 2/447 |
| WO | WO2013062716 | | 5/2013 | |
| WO | WO2013124453 | | 8/2013 | |

OTHER PUBLICATIONS

Interverbral nucleus prosthesis and surgical procedure for implanting the same, Gau, Michel, U.S. Appl. No. 10/060,862, filed Jan. 30, 2002.
Intersomatic cage with unified grafts, Huppert, Jean, U.S. Appl. No. 10/276,712, filed Mar. 26, 2003.
Spinal Osteosynthesis Device and Preperation Method, Beaurain, Jacques et al., U.S. Appl. No. 10/473,999, filed Apr. 12, 2004.
Intervertebral Disc Prosthesis and Fitting Tools, Beaurain, Jacques et al., U.S. Appl. No. 10/476,565, filed Jun. 8, 2004.
Vertebral Cage Device With Modular Fixation, Louis, Christian et al., U.S. Appl. No. 10/483,563, filed May 21, 2004.
Progressive approach osteosynthesis device and preassembly method, Delecrin, Joel et al., U.S. Appl. No. 10/492,753, filed Aug. 9, 2004.
Plate for osteosynthesis device and method of preassembling such device, Delecrin, Joel et al., U.S. Appl. No. 10/492,827, filed Jul. 15, 2004.
Osseous anchoring device for a prosthesis, Huppert, Jean et al., U.S. Appl. No. 10/494,418, filed Jul. 22, 2004.
Implant for Osseous Anchoring with Polyaxial Head, Beaurain, Jacques et al., U.S. Appl. No. 10/498,234, filed Dec. 7, 2004.
Intervertebral Disc Prosthesis, Beaurain, Jacques et al., U.S. Appl. No. 10/533,846, filed Nov. 11, 2005.
Osseous anchoring implant with a polyaxial head and method for installing the implant, Renaud, Christian et al., U.S. Appl. No. 10/570,080, filed Jun. 9, 2006.
Device and method for sectioning a vertebral lamina, Mangione, Paolo, U.S. Appl. No. 10/575,065, filed May 30, 2006.
Intervertebral Disc Prosthesis, Hovorka, Istvan et al., U.S. Appl. No. 11/051,710, filed Feb. 4, 2005.
Intervertebral Disc Prosthesis, Zeegers, M. Willem, U.S. Appl. No. 11/098,266, filed Apr. 4, 2005.
Intervertebral Disc Prosthesis, Zeegers, Willem, U.S. Appl. No. 11/109,276, filed Apr. 18, 2005.
Instrumentation and Methods for Inserting an Intervertebral Disc Prosthesis, Dinville, Herve, U.S. Appl. No. 11/180,868, filed Jul. 13, 2005.
Intervertebral Disc Prosthesis, Rashbaum, Ralph et al., U.S. Appl. No. 11/341,007, filed Jan. 27, 2006.
Intervertebral Disc Prosthesis and Instrumentation for Insertioin of the Prosthesis Between the Vertebrae, Rashbaum, Ralph et al., U.S. Appl. No. 11/362,253, filed Feb. 24, 2006.
Transforaminal intersomatic cage for a intervertebral fusion graft and an instrument for implanting the cage, Davis, Reginald James et al., U.S. Appl. No. 11/378,165, filed Mar. 17, 2006.
Intervertebral nucleus prosthesis and surgical procedure for implanting the same, Gau, Michel, U.S. Appl. No. 11/390,711, filed Mar. 27, 2006.
Intervertebral disc prosthesis insertion assemblies, Jodaitis, Alexandre et al., U.S. Appl. No. 11/676,237, filed Feb. 16, 2007.
Intersomatic cage with grafts, Huppert, Jean, U.S. Appl. No. 11/767,386, filed Jun. 22, 2007.
Nucleus Prostheses, Vila, Thierry et al., U.S. Appl. No. 11/874,144, filed Oct. 17, 2007.
Vertebral Support Device, Cho, Paul et al., U.S. Appl. No. 11/958,285, filed Dec. 17, 2007.
Intervertebral disc prosthesis, surgical methods, and fitting tools, Beaurain, Jacques et al., U.S. Appl. No. 12/025,677, filed Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Cho, Paul, U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, Willem, U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumental and Methods for Inserting an Intervertebral Disc Prosthesis, Dinville, Herve, U.S. Appl. No. 12/435,955, filed May 5, 2009.
Interveterbral disc prosthesis insertion assemblies, Jodaitis, Alexandre et al., U.S. Appl. No. 12/527,373, dated Mar. 19, 2010.
Interveteberal implant having extendable bone fixation members, Brett, Darrell C., U.S. Appl. No. 12/884,664, filed Sep. 17, 2010.
Intervertebral Disc Prosthesis, Rashbaum, Ralph et al., U.S. Appl. No. 12/955,898, filed Nov. 29, 2010.
Instrumental and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Hervéet al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., U.S. Appl. No. 13/454,927, filed Apr. 24, 2012.
Anchoring Device and System for an Intervertebral Implant, Intervertebral Implant and Implantation Instrument, Dinville, Hervé et al., U.S. Appl. No. 13/520,041, filed Nov. 26, 2012.
Anchoring Device and System for an Intervertebral Implant, Intervertebral Implant and Implantation Instrument, Dinville, Hervé et al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, Willem, U.S. Appl. No. 13/603,043, filed Sep. 4, 2012.
Intervertebral Disc Prosthesis, Beaurain, Jacques et al., U.S. Appl. No. 13/616,448, filed Sep. 14, 2012.

(56) References Cited

OTHER PUBLICATIONS

Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant intervertebral implant, intervertebral implant and implantation instrument, Chataigner, Hervé et al., U.S. Appl. No. 13/774,547, filed Feb. 22, 2013.
Transforaminal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Interesting Disc Prosthesis, Dinville, Herve, U.S. Appl. No. 13/892,933, filed May 13, 2013.
Intervertebral Disc Prosthesis Insertion Assemblies, Jodaitis, Alexandre et al., U.S. Appl. No. 13/919,704, filed Jun. 17, 2013.
Intervertebral implant having extendable bone fixation members, Brett, Darrell C., U.S. Appl. No. 14/064,434, filed Oct. 28, 2013.
Interspinous Implant and Instrument for Implanting an Interspinous Implant, Dinville, Hervé et al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prosthesis, Vila, Thierry et al., U.S. Appl. No. 14/159,161, filed Jan. 20, 2014.
Interveterbral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al., U.S. Appl. No. 14/246,442, filed Apr. 7, 2014.
Interspinous Implant and Instrument for Implanting an Interspinous Implant, Dinville, Hervé et al., U.S. Appl. No. 14/252,754, filed Apr. 14, 2014.
Anchoring device for a spinal implant, spinal implant and implantation instrumentation, Chataigner, Hervé et al., U.S. Appl. No. 14/252,852, filed Apr. 15, 2014.
Intervertebral Disc Prosthesis, Beaurain, Jacques et al., U.S. Appl. No. 14/306,785, filed Jun. 17, 2014.
Intervertebral Disc Prosthesis and Instrumental for Insertion of the Prosthesis Between the Vertebae, Steib, Jean-Paul, U.S. Appl. No. 14/325,317, filed Jul. 7, 2014.
Anchoring device and system for an intervertebral implant, intervertebral implant and implantation instrument, Chataigner, Hervé et al., U.S. Appl. No. 14/380,714, filed Aug. 23, 2014.
Cage Having Spike, Kim, Seo-Kon et al., U.S. Appl. No. 14/460,536, filed Aug. 15, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis, Hovorka, Istvan et al., U.S. Appl. No. 14/513,818, filed Oct. 14, 2014.
Plate for osteosynthesis device and preassembly method, Delecrin, Joel et al., U.S. Appl. No. 14/584,674, filed Dec. 29, 2014.
Intervertebral Implant Having Extendable Bone Fixation Members, Brett, Darrell C., U.S. Appl. No. 14/594,770, filed Jan. 12, 2015.
Vertebral implant, device for vertebral attachment of the implant and instrumentation for implantation thereof, Ameil, Marc et al., U.S. Appl. No. 14/638,746, filed Mar. 4, 2015.
Intervertebral Disc Prosthesis, Zeegers, Willem, U.S. Appl. No. 14/642,696, filed Mar. 9, 2015.
Vertebral Support Device, Cho, Paul et al., U.S. Appl. No. 14/642,752, filed Mar. 10, 2015.
Intervertebral Disc Prosthesis, Rashbaum, Ralph et al., U.S. Appl. No. 14/659,587, filed Mar. 16, 2015.
Anchoring device and system for an intervertebral implant, intervertebral implant and implantation instrument, Chataigner, Hervé et al., U.S. Appl. No. 14/721,818, filed May 26, 2015.
Intervertebral Disc Prosthesis, Zeegers, Willem, U.S. Appl. No. 14/726,557, filed May 31, 2015.
Anchoring Device and System for an Intervertebral Implant, Intervertebral Implant, Intervertebral Implant and Implantation Instrument, Dinville, Hervé et al., U.S. Appl. No. 14/726,558, filed May 31, 2015.
Vertebral Cage Device With Modular Fixation, Louis, Christian et al., U.S. Appl. No. 14/798,900, filed Jul. 14, 2015.
Bone Implants, Lavigne, Christophe et al., U.S. Appl. No. 14/815,900, filed Jul. 31, 2015.
Devices, Methods, and Systems to Implant and Secure a Fusion Cage or Intervertebral Prosthesis for Spinal Treatment, Stewart, Will et al., U.S. Appl. No. 14/827,297, filed Aug. 15, 2015.
Vertebral implant, vertebral fastening device of the implant and implant instrumentation, Dinville, Herve et al., U.S. Appl. No. 14/891,322, filed Nov. 13, 2015.
Instruments and Methods for Removing Fixation Devices from Intervertebral Implants, Dinville, Herve et al., U.S. Appl. No. 14/931,007, filed Nov. 3, 2015.
Instrumentation and Methods for Inserting an Intervertebral Disc Prosthesis, Dinville, Herve, U.S. Appl. No. 15/012,815, filed Feb. 1, 2016.
Intervertebral Disc Prosthesis, Beaurain, Jacques et al., U.S. Appl. No. 15/049,934, filed Feb. 22, 2016.
Intervertebral Disc Prosthesis and Instrumentation for Insertion of the Prosthesis Between the Vertebrae, Steib, Jean-Paul, U.S. Appl. No. 15/049,995, filed Feb. 22, 2016.
Anchoring device for a spinal implant, spinal implant and implantation instrumentation, Chataigner, Hervé et al., U.S. Appl. No. 15/115,659, dated Jul. 29, 2016.
Interspinous Implant and Instrument for Implanting an Interspinous Implant, Dinville, Hervé et al., U.S. Appl. No. 15/145,413, filed May 3, 2016.
Implant for Osseous Anchoring with Polyaxial Head, Beaurain, Jacques et al., U.S. Appl. No. 15/145,431, filed May 3, 2016.
Intervertebral disc prosthesis, surgical methods, and fitting tools, Beaurain, Jacques et al., U.S. Appl. No. 15/150,316, filed May 9, 2016.
Interspinous Implant and Instrument for Implanting an Interspinous Implant, Dinville, Hervé et al., U.S. Appl. No. 15/225,612, filed Aug. 1, 2016.
Intervertebral Disc Prosthesis, Zeegers, M. Willem, U.S. Appl. No. 15/269,923, filed Sep. 19, 2016.
Intervertebral Implant Having Extendable Bone Fixation Members, Brett, Darrell C., U.S. Appl. No. 15/289,861, filed Oct. 10, 2016.
Vertebral implant, device for vertebral attachment of the implant and instrumentation for implantation thereof, Ameil, Marc et al., U.S. Appl. No. 15/309,197, filed Nov. 6, 2016.
Intervertebral Disc Prosthesis Insertion Assemblies, Jodaitis, Alexandre et al., U.S. Appl. No. 15/340,565, filed Nov. 1, 2016.
Nucleus Prosthesis, Vila, Thierry et al., U.S. Appl. No. 15/391,305, filed Dec. 27, 2016.
Plate for osteosynthesis device and preassembly method, Delecrin, Joel et al., U.S. Appl. No. 15/414,523, filed Jan. 24, 2017.
Implant for Osseous Anchoring with Polyaxial Head, Beaurain, Jacques et al., U.S. Appl. No. 15/426,938, filed Feb. 7, 2017.
Intervertebral Disc Prosthesis, Zeegers, Willem, U.S. Appl. No. 15/432,795, filed Feb. 14, 2017.
System of spinal arthodesis implants, Mercier, Alexis et al., U.S. Appl. No. 15/442,591, filed Feb. 24, 2017.
Intervertebral Disc Prosthesis, Rashbaum, Ralph et al., U.S. Appl. No. 15/464,639, filed Mar. 21, 2017.
Transforaminal intersomatic cage for an intervertebral fusion graft and an instrument for implanting the cage, Davis, Reginald James et al., U.S. Appl. No. 15/465,143, filed Mar. 21, 2017.
Bone Implants, Lavigne, Christophe et al., U.S. Appl. No. 15/501,166.
Bone anchoring system, associated implant and instrumentation, Lequette, Samuel et al., U.S. Appl. No. 15/582,568, filed Apr. 28, 2017.

(56) References Cited

OTHER PUBLICATIONS

Intervertebral Fusion Cage with Retractable-Extrudable Pins, Brett, Darrell C., U.S. Appl. No. 61/243,297, filed Sep. 17, 2009.
Intervertebral Fusion Cage with Retractable-Extrudable Pins, Brett, Darrell C., U.S. Appl. No. 61/260,364, filed Nov. 11, 2009.
National Institute of Industrial Property (France); Search Report in Fench Pub. No. FR3016793, App. No. FR1450749 (with translated abstract); dated Sep. 11, 2014; National Institute of Industrial Property (France); France; all pages.
World Intellectual Property Organization; International Search Report and Written Opinion of the International Searching Authority for International App. No. WO2015114122, PCT Pub'n No. PCT/EP2015/052019; dated May 13, 2015; WIPO; Geneva, Switzerland; all pages.
World Intellectual Property Organization; International Preliminary Report on Patentability for International App. No. WO2015114122, PCT Pub'n No. PCT/EP2015/052019; dated Aug. 2, 2016; WIPO; Geneva, Switzerland; all pages.

* cited by examiner

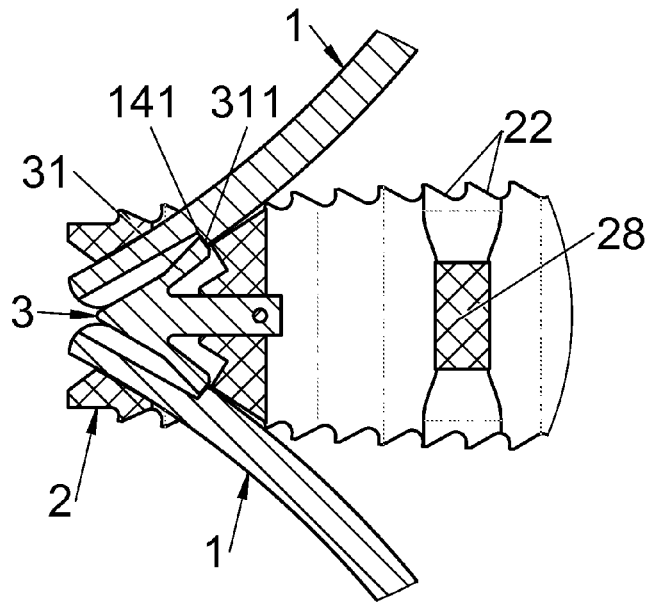
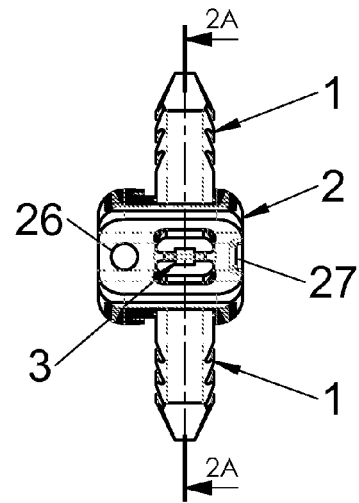
Figure 2A    Figure 2B
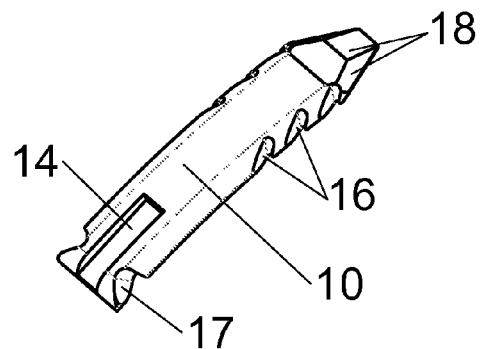
Figure 2C
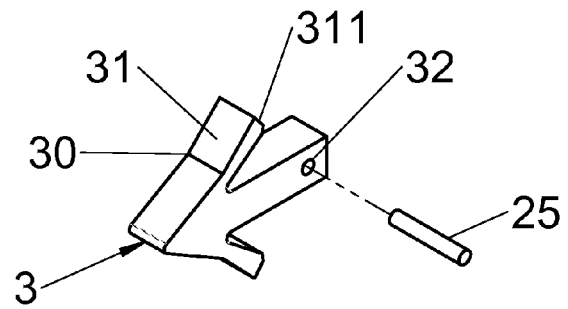
Figure 2D

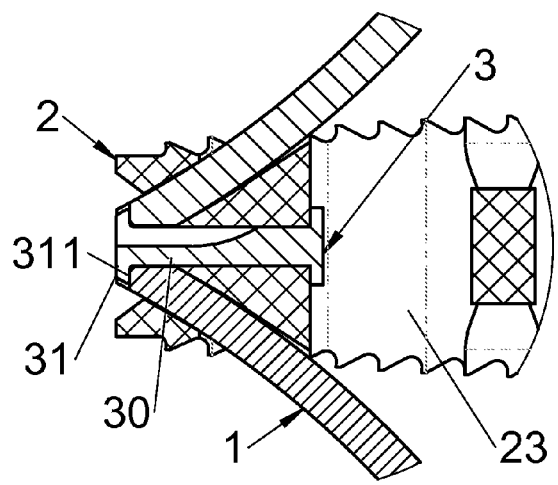
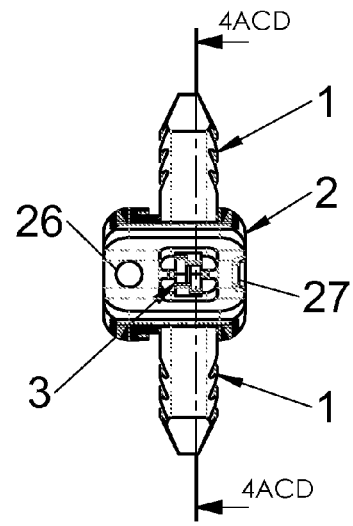
Figure 4A                Figure 4B
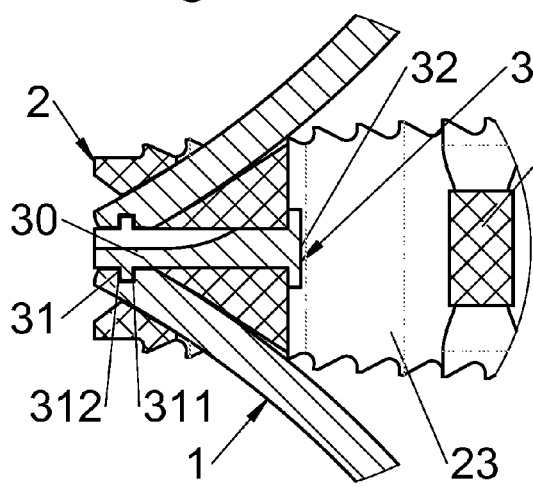
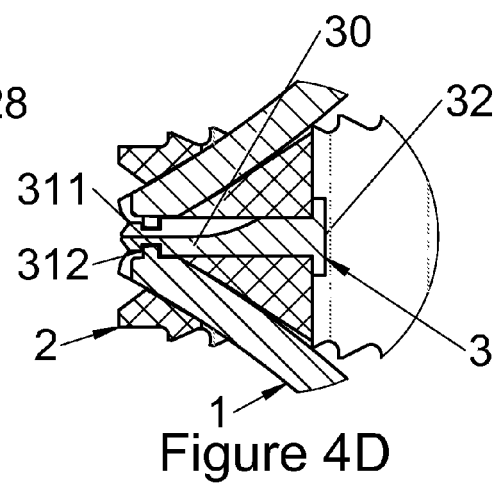
Figure 4C                Figure 4D
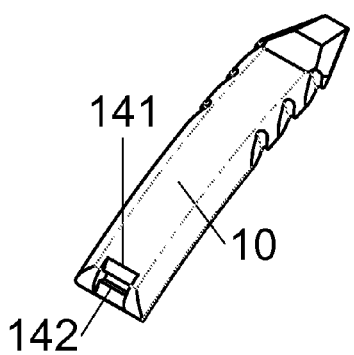 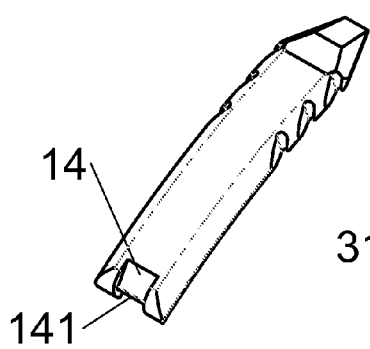 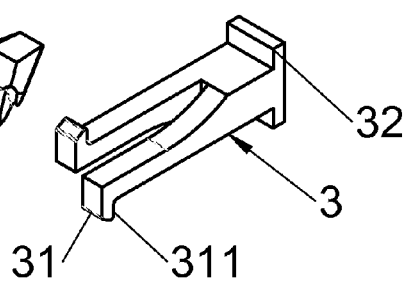
Figure 4E                Figure 4F                Figure 4G

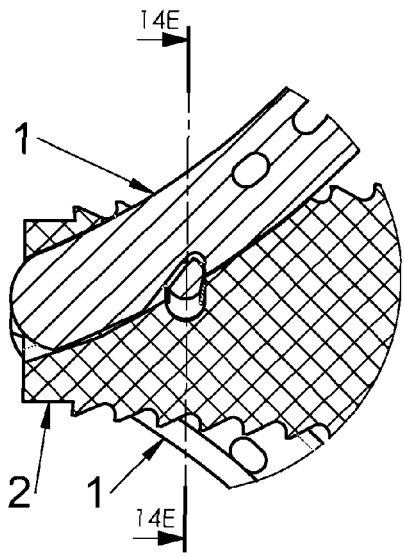
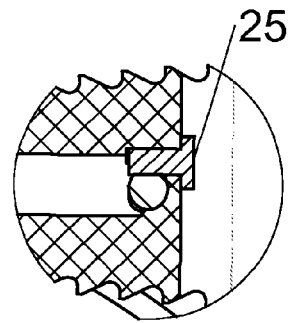
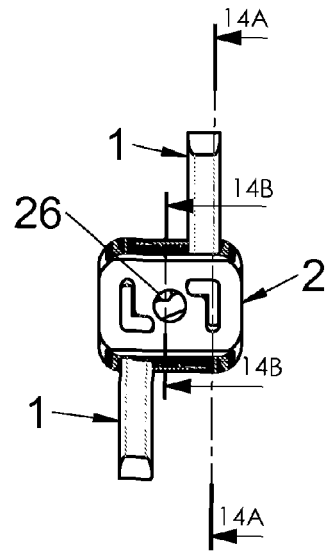
Figure 14A  Figure 14B  Figure 14C
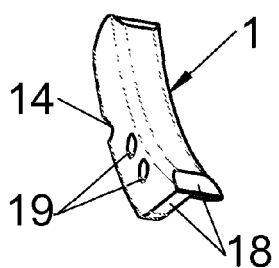
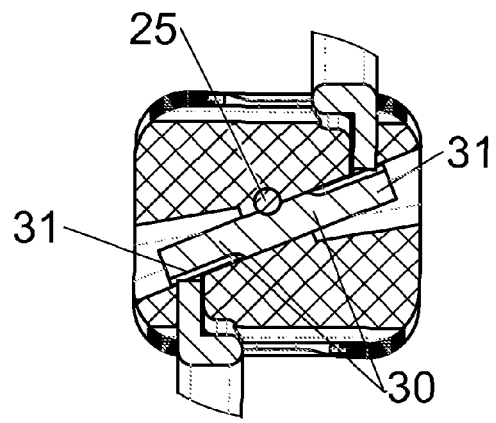
Figure 14D
Figure 14E
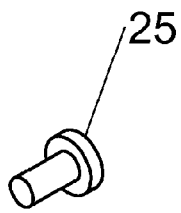
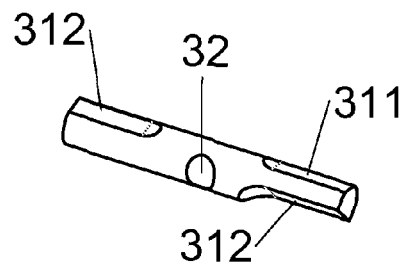
Figure 14F  Figure 14G

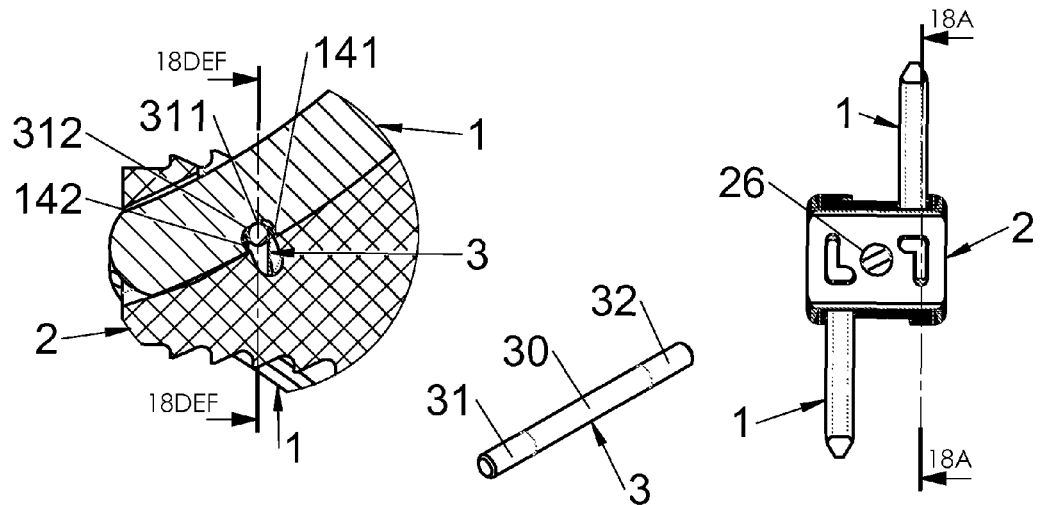
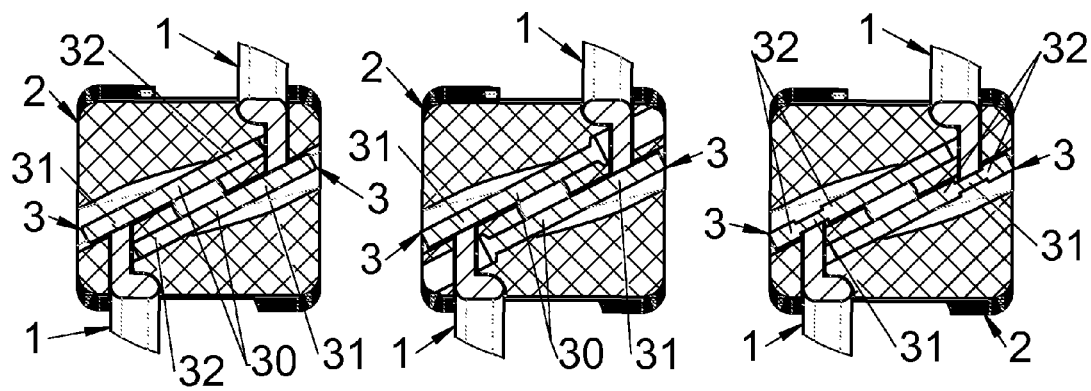
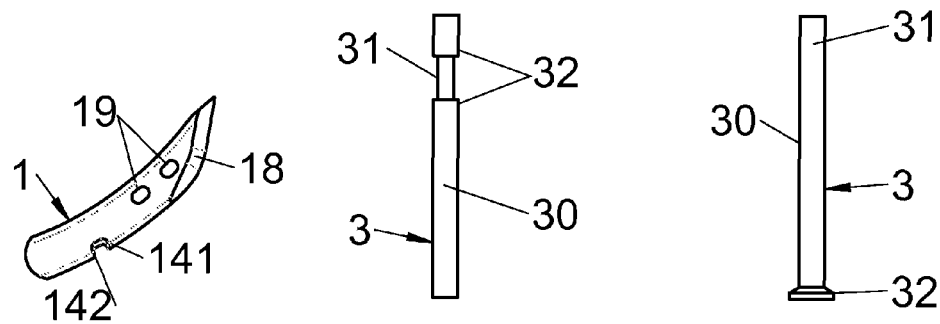
Figure 18A    Figure 18B    Figure 18C
Figure 18D    Figure 18E    Figure 18F
Figure 18G    Figure 18H    Figure 18I

ANCHORING DEVICE FOR A SPINAL IMPLANT, SPINAL IMPLANT AND IMPLANTATION INSTRUMENTATION

CROSS-REFERENCE TO RELATED APPLICATIONS

This application claims priority under 35 U.S.C. § 119 to French patent application number FR1450749 filed in France on Jan. 30, 2014, which is incorporated herein by reference.

BACKGROUND

This disclosure relates to orthopedic implants, in including rachidian (spinal) implants, such as intersomatic cages for example. Intersomatic cages may be implanted between two adjacent vertebrae for placement and growth of bone tissue grafts (or substitute) in the discal space and for obtaining arthrodesis (merging of two vertebrae). For example, after putting the cage into place, the intervertebral space is filled with autologous cancellous bone or suitable bone substitutes which may also (or as an alternative) be placed in a cavity of the cage before its positioning in the space. This disclosure relates to intervertebral implants such as intersomatic cages but also relates to other types of implants such as for example intervertebral disc prostheses or arthrodesis plates. Further, among other subject matters this disclosure relates to bone anchoring devices (anchors) for fixing implants in the vertebrae and implanting implants in the discal space with instrumentation for implanting and attaching implants to the vertebrae through anchors.

A problem in this field sometimes relates to the stability of the rachidian implants in the discal space once they have been implanted. This stability may aide intervertebral disc prostheses to preserve a certain degree of mobility to the vertebrae between which they are implanted, but also may aide other types of implants, for example when arthrodesis is desired, for example by using intersomatic cages and/or other implants allowing arthrodesis (which may for example be achieved by means of auxiliary stabilizing structures such as osteosynthesis bars. Indeed, for example, there can exist a risk that the implant moves in the intervertebral space under the effect of the forces experienced during movement of the patient, even when the implant is provided with catches or teeth on its vertebral contact surfaces. It is therefore often desirable to attach the rachidian implant to the adjacent vertebrae between which it is implanted. In the case of arthrodesis, provision is also often made for osteosynthesis bars immobilizing the vertebrae, for example with lordosis, in order to avoid the possibility that the cage moves out of the intervertebral space. In the prior art, solutions are known which provide the rachidian implant with a bone anchoring device which allows the implant to be firmly fixed in the vertebrae between which the implant is intended to be implanted.

Another problem in the field sometimes relates to invasivity and access to the intervertebral spaces (discal spaces) which is often delicate because of congestion, notably because of the presence of blood vessels and nerves in the vicinity of the intervertebral space, as well as the proximity of the spinal cord. The bone anchoring devices which have to penetrate sufficiently deep into the vertebrae in order to ensure proper attachment, therefore may benefit from a small size while allowing the implant to be attached without jeopardizing the blood vessels and the surrounding nerve tissues (for example by not requiring more room in the vicinity of the intervertebral space than required for the implantation of the actual rachidian implant). For example, certain implants (notably intersomatic cages) are equipped for being implanted through a posterior route (from the rear of the patient) or a transforaminal route (through the foramen). The posterior route generally requires partial resection of the articular joints and passes between the dura mater and the articular joints (generally two cages positioned substantially parallel to the sagittal plane are provided). This route therefore often follows a direction very close to the spinal cord and uses cages of reduced dimensions. The transforaminal route follows an oblique route with regard to the sagittal plane and requires cages of reduced dimensions but of sufficient length so as to be positioned obliquely or perpendicular to the sagittal plane. Generally, small access routes are sought for limiting the invasivity of the surgical implantation operation. Further, with this view of limiting invasivity, it is optionally sought to avoid having to lay additional equipment (either posterior or anterior), such as osteosynthesis bars (with pedicle screws generally) or osteosynthesis plates. The use of anchoring means for attaching the cages might give the possibility of addressing this problem if these anchoring means are reliable. The cages are generally placed between the vertebrae at an anterior position on the vertebral plates, so as to impose a lordosis. The osteosynthesis bars may be used for imposing lordosis which prevents the cage from moving backwards but anchoring means therefore may be preferred over them if the obtained attachment and stability of the implant are reliable. Such anchoring means therefore preferably limit invasivity as well, in addition to being reliable and stable.

Another problem that may exist for the bone anchoring means relates to ablation. Indeed, it is generally desired to be able to remove the bone anchoring means (and the implant in general). Therefore the bone anchoring means preferably may be retained in the implant in a stable way but they may also be removed as easily as possible. Further, easy ablation should also preferably be feasible with limited invasivity.

In the prior art, notably from the published patent applications WO 2008/149223 and WO2011/080535 filed by the applicant of the present application, to which the reader may refer for examining various problems addressed and the advantages provided by this type of solution, an anchoring device is known, suitable for being firmly implanted and sufficiently deep in the vertebral plate for ensuring good support of the implants applied against these vertebrae, but along an approach axis for insertion, substantially (i.e. generally) in the plane of the intervertebral space. This type of solution typically includes at least one anchor formed by a plate, which is often curved and generally stiff, laid out for penetrating into a plate of a vertebra through an implant and provided with at least one abutment for retaining an implant against this vertebra. This type of anchoring devices or anchor, including a plate intended to be planted into the bone may sometimes pose a risk of the vertebra being split by the plate, during its impaction in the vertebra or under the effect of the forces exerted on the implant and/or on the anchor once it is planted into the vertebra. Also, this type of anchor may sometimes have the risk of causing a too large notch during its impaction in the vertebra, which may induce the possibility of undesirable play of the anchor which risks weakening the (fragile) attachment of the implant and/or making it not very reliable. Application WO2011/080535 is directed to this type of problem, among others. It will be noted that by the term of impaction is meant here the fact of planting the anchoring device into the vertebrae. It will be noted that the present application discloses an impactor which is an impaction device since it is laid out for allowing an anchoring device to be planted in a vertebra. On the other hand, another potential problem of this type of anchor including a plate relates to stiffness. Under certain circumstances, it is important that the anchor be sufficiently stiff so as not to deform and/or not have too much play under the effect of the forces which are exerted thereon, in order to avoid it gradually moving out of the vertebra in which it is anchored and to limit the risk of mobility of the cage in the intervertebral space. The stiffness of this type of anchor is therefore often an important feature for allowing efficient attachment, which in some circumstances may be more efficient than staples or other fine and/or relatively flexible or even fragile devices.

Another problem may relate to the risks of making the implant fragile by the layout of attachment means against the vertebrae. This problem may relate to the size of the anchor relative to the implant, for example the size of the passage of the implant intended to receive this anchor. Indeed, the passing of the anchor through the implant and the maintaining of the stability of this kind of anchor in the implant (possibly subject to a desired play, for example a minimum play) is also an aspect which may facilitate more reliable attachment under certain circumstances. Application WO2011/080535, among other subject matter, also addresses this type of stability problem. These anchoring devices may provide a good anchoring solution with limited invasivity, but they may in some circumstances still require too large a size for adapting to the dimensional constraints of certain implants, such as for example the posterior or transforaminal approach cages, and may therefore be improved for further limiting invasivity. Further, the removal of this type of bone anchoring means may be a problem, for example if it is intended that removal should be easy while limiting invasivity. Also, application WO2013/124453, filed by the applicant of the present application, among other subjects addresses these issues of weakening of the implants by the anchors and of easy removal of the anchors. However, it is still useful to propose other types of solutions, for example addressing these problems in ways that may be more efficient under some circumstances. Further, depending on the relevant type of implant, it may be useful that the generally stiff anchor be retained by a structure which is also firm, in order to minimize damaging the implant under the action of the forces exerted on the anchor and the implant. For example, in the case of an implant of a more flexible or less robust material than that of the anchors, there may exist a risk of weakening the implant or of retaining the anchor in the implant.

In this context, it is interesting to propose solutions that may mitigate one or more of the drawbacks (and/or other ones) of the prior art.

SUMMARY

Certain embodiments incorporating various technical features described in the present application therefore seek to mitigate at least one of the drawbacks (and/or other ones), of the prior art by proposing anchoring devices for rachidian implants which are (more) compact (less cumbersome) and/or for which removal possibility is improved and/or which provides better reliability (increased stability of the anchor and of the implant and/or reduced risk of weakening the implant). On the other hand, certain embodiments also may seek to mitigate various problems by proposing an easily implantable anchoring device, notably through an approach route along an axis substantially perpendicular to the axis of the rachis, and which may be stiff and allow reliable attachment with a low risk of damaging the vertebrae, for example through the posterior and/or transforaminal implantation routes.

Various embodiments of bone anchoring devices for a spinal implant may be laid out so as to be inserted through a passage crossing through at least one portion of the implant, for example from an outer surface to a vertebral contact surface, and such a device may include a body comprising at least one stiff plate elongated along a longitudinal axis extending between an anterior end and a posterior end, the plate being configured so that its anterior end may penetrate into at least one vertebral surface while its posterior end remains in the passage of the implant, while retaining said implant against said vertebral surface. In some embodiments, the body includes at least one abutment oriented not parallel to the longitudinal axis and complementary to at least one abutment of at least one locking means of the device relative to the implant, said locking means, equipping the implant, being provided with at least one flexible portion allowing said abutment of the locking means to be pushed back for inserting the anchoring device into the passage, on the one hand, and mutual engagement of both abutments when they are found facing each other, by the elastic return of the flexible portion on the other hand.

According to another feature of some embodiments, an anchoring device may include at least one hooking-up means configured for hooking up the end of a tool allowing withdrawal of the anchoring device.

According to another feature of some embodiments, a hooking-up means is located near the posterior end of the device.

According to another feature of some embodiments, the anchoring device may include at least one means for accessing the locking means in order to disengage the respective abutments of the anchoring device and of the locking means.

According to another feature of some embodiments, an abutment of the device comprises at least one abutment surface oriented substantially facing the posterior end of the anchoring device in order to cooperate with at least one complementary abutment surface with opposite orientation, on the abutment of the locking means and thereby opposing the withdrawal of the device out of said passage.

According to another feature of some embodiments, an abutment surface of the abutment of the device is oriented non-perpendicularly to the axis of the anchoring device for insertion into the implant, so as to allow the abutment of the locking means to be pushed back and thereby unlock the anchoring device by traction exerted on a hooking-up means.

According to another feature of some embodiments, an abutment of the device comprises at least one abutment surface oriented facing the anterior end of the anchoring device for cooperating with at least one complementary abutment surface, with opposite orientation, on the abutment of the locking means and thereby opposing excessive advance of the device in said passage.

According to another feature of some embodiments, an abutment of the device is a female abutment cooperating with a male abutment of the locking means.

According to another feature of some embodiments, an abutment of the device is a male abutment cooperating with a female abutment of the locking means.

According to another feature of some embodiments, an abutment of the device is a recess in a surface of the anchoring device, intended to cooperate with a protrusion forming the abutment of the locking means.

According to another feature of some embodiments, an abutment of the device forms a protrusion jutting out from a surface of the anchoring device and intended to cooperate with a recess in a surface of the locking means.

According to another feature of some embodiments, a stiff plate is curved and complementary to the shape of the passage of the implant so as to cross the implant without any deformation and to be inserted therein along an axis non-perpendicular to the vertebral surface into which should penetrate the anterior end.

According to another feature of some embodiments, a body describes at least one circular or elliptical arc having dimensions and at least one radius of curvature achieved in such a way that the anchoring device is implantable in a vertebral plate along an approach axis forming with the vertical axis of the rachis an angle of approximately 90°, while having its longitudinal axis substantially in the plane of the intervertebral space.

According to another feature of some embodiments, an abutment of the device is formed with a surface of the posterior end of the plate which is made for sufficiently penetrating into the implant.

According to another feature of some embodiments, a body includes a second plate elongated along said longitudinal axis of the first plate and extending between the anterior end and the posterior end, the second plate being secured to the first plate and substantially perpendicular to the first plate, giving the device a L-shaped section mating the internal section of the passage in the implant.

According to another feature of some embodiments, a body includes, at least at its anterior end, at least one chamfer or bevel facilitating penetration of the device into said vertebral surface.

According to another feature of some embodiments, an anterior end includes at least one notch facilitating the penetration of the device into said vertebral surface.

According to another feature of some embodiments, a body is provided with catches oriented so as to oppose the withdrawal of the device once it is implanted in a vertebra.

According to another feature of some embodiments, a body is provided, at the portion intended to penetrate into the vertebral surface, with at least one hole allowing bone growth through the anchoring device.

Another purpose of some embodiments incorporating various technical features disclosed in the present application is to mitigate at least one of the disadvantages of the prior art by proposing spinal implants adapted to be secured by anchoring devices according to various embodiments of this disclosure, and that are (more) compact (little cumbersome) and/or with the possibility of removal is improved and/or which offers better reliability (increased stability and anchor the implant and/or reduced risk of weakening the implant). Furthermore, some embodiments are also intended to address various problems by providing an implantable spinal implant easily, for example by way of approach along an axis substantially perpendicular to the axis of the spine, and which may be attached reliably with a low risk of damage to the vertebrae, especially the posterior tract implantation and/or transforaminal.

This purpose may be furthered with a spinal implant embodiment including at least one outer surface and at least one vertebral contact surface through which the implant is intended to be placed in contact with at least one vertebral surface, said spinal implant being configured so as to receive at least one anchoring device, by means of at least one passage crossing at least one portion of the implant along a so-called insertion axis, from said outer surface to said vertebral contact surface, the implant including at least one means for locking the device relative to the implant, said locking means being provided with at least one flexible portion and with at least one abutment oriented non-parallel to the insertion axis of the passage and mating said abutment of the device for cooperating with it and thereby locking the device relative to the implant, the flexibility of said flexible portion allowing said abutment of the locking means to be pushed back for inserting the anchoring device into the passage on the one hand, and, mutual engagement of both abutments when they are found facing each other, by the elastic return of the flexible portion.

According to another feature of some embodiments, the spinal implant may include at least one means for accessing the locking means for disengaging the respective abutments of the anchoring device and of the locking means.

According to another feature of some embodiments, the spinal implant may include at least one means for accessing, from the outside of the implant, at least one hooking-up means of the anchoring device configured for hooking up the end of a tool allowing withdrawal of the anchoring device.

According to another feature of some embodiments, an abutment of the locking means comprises at least one abutment surface oriented substantially facing the outlet of the passage, towards the vertebral contact surface for cooperating with at least one complementary abutment surface, with opposite orientation, on the abutment of the anchoring device and thereby opposing its withdrawal out of said passage.

According to another feature of some embodiments, an abutment surface of the abutment of the locking means is oriented non-perpendicularly to the axis of the passage of the anchoring device in the implant, in order to allow the abutment of the locking means to be pushed back and thereby unlock the anchoring device by traction exerted on a hooking-up means of the anchoring device.

According to another feature of some embodiments, an abutment of the locking means comprises at least one abutment surface oriented facing the inlet of the passage, towards the outer surface, for cooperating with at least one complementary abutment surface, with opposite orientation, on the abutment of the anchoring device and opposing excessive advance of the device in said passage.

According to another feature of some embodiments, an abutment of the locking means is a male abutment cooperating with a female abutment of the anchoring device.

According to another feature of some embodiments, an abutment of the locking means is a female abutment cooperating with a male abutment of the device.

According to another feature of some embodiments, an abutment of the locking means forms a protrusion intended to cooperate with the abutment of the device formed by a recess in a surface of the anchoring device.

According to another feature of some embodiments, an abutment of the locking means is a recess in a surface of the locking means intended to cooperate with the abutment formed by a protrusion jutting out from a surface of the anchoring device.

According to another feature of some embodiments, a passage is rectilinear or curved and complementary to the shape of the curved anchoring device so as to allow the passing of the anchoring device through the implant without any deformation, by insertion along an axis non-perpendicular to the vertebral surface into which should penetrate the anterior end.

According to another feature of some embodiments, a passage in the implant has an L-shaped internal section, mating the shape of the anchoring device, the body of which includes a second plate elongated along said longitudinal axis of the first plate and extending between the anterior end and the posterior end, the second plate being secured to the first plate and substantially perpendicular to the first plate.

According to another feature of some embodiments, a locking means is retained in a housing of the implant and oriented along a direction non-parallel to the insertion axis of the anchoring device.

According to another feature of some embodiments, a locking means is retained in the implant by retention means preventing the movement of the abutment in the direction of the insertion and/or the withdrawal of the anchoring device.

According to another feature of some embodiments, retention means are configured so that the locking means is removable.

According to another feature of some embodiments, retention means are formed with catches on at least one surface of the locking means in order to be anchored into the walls of a housing of the implant into which is inserted the locking means.

According to another feature of some embodiments, retention means are formed with at least one shoulder of the locking means intended to abut against the anchoring device on either side of its abutment, so that the anchoring device prevents the movement of the locking means in the spinal implant.

According to another feature of some embodiments, retention means are formed with a recess in a locking means intended to receive a pin or a staple inserted through the spinal implant in order to cooperate with this recess.

According to another feature of some embodiments, retaining means are formed with a housing in the locking means intended to receive a stick inserted into this housing through a conduit of the spinal implant.

According to another feature of some embodiments, a locking means is formed by an insert of elongated shape along a longitudinal axis non-parallel to the insertion axis.

According to another feature of some embodiments, a locking means is formed by an insert with the shape of a split ring inserted into a complementary housing of the spinal implant near said passage.

According to another feature of some embodiments, a locking means is formed with a cylindrical insert screwed into a housing of the spinal implant and its abutment is formed with at least one flexible tab opening into the passage in order to cooperate with the abutment of the anchoring device.

According to another feature of some embodiments, a spinal implant may be formed with at least one intersomatic cage comprising a body forming a means for maintaining the height of the intervertebral space, said at least one passage crossing said body from a peripheral wall to a vertebral contact surface of the cage.

According to another feature of some embodiments, a spinal implant may be formed with at least one intervertebral disc prosthesis comprising at least two plates jointed together by at least one curved surface, said at least one passage crossing at least one of the two plates, from a peripheral edge of the plate or from an internal face of the prosthesis, towards a vertebral contact surface of the prosthesis.

According to another feature of some embodiments, a spinal implant may be formed with at least one osteosynthesis plate crossed by the passage from an outer face to a vertebral contact face of the osteosynthesis plate.

According to another feature of some embodiments, a locking means is directly machined in the thickness of said plate or of said plate.

According to another feature of some embodiments, the spinal implant may include at least one hooking-up means for its grasping by a surgical instrument.

Another purpose of some embodiments incorporating various technical features described in this application is to mitigate at least one of the disadvantages of the prior art by providing a surgical instrumentation for implantation and fixation of spinal implants (vertebral) including interbody cages, for example along an axis of approach substantially in the plane of the intervertebral space, for limiting the invasiveness.

This purpose is furthered, for example, with a surgical instrumentation, for implanting a spinal implant and for attaching this implant in at least one vertebra with at least one anchoring device, the instrumentation comprising:

an implant-holder of elongated shape along a longitudinal axis extending between a first end, said for grasping the implant, and a second end said to be pusher, the grasping end including a head provided at its end with at least one means for grasping the implant, the head being crossed by a longitudinal passage opening on the implant and capable of receiving said anchoring device, at least one impactor of elongated shape along a longitudinal axis extending between both ends of the impactor, one of the ends comprising at least one branch capable of penetrating into the implant-holder for pushing the posterior end of said anchoring device, while the other end of the impactor comprises a so-called impaction surface, laid out for receiving a thrust and impact for having the anterior end of said anchoring device penetrate into a vertebra through the passage of the implant, at least one guiding surface of the anchoring device for guiding the sliding of the latter in the implant-holder right through the implant, the instrumentation including at least one means for accessing the complementary abutments (14, 31) of the anchoring device (1) and of the locking means (3) for pushing back the locking means (3) upon inserting said anchoring device (1) into the passage of the implant.

According to another feature of some embodiments, the surgical instrumentation may include at least one retention means capable of cooperating with said abutment of the anchoring device for retaining the latter in the implant-holder before actuating the impactor.

According to another feature of some embodiments, the surgical instrumentation may include at least one loader capable of sliding in the head of the implant-holder and provided with said guiding surface and said retention means.

According to another feature of some embodiments, the surgical instrumentation may include two loaders, each of them being provided with a guiding surface and a retention means on the one hand and capable of sliding in the head of the implant-holder on the other hand.

According to another feature of some embodiments, an impactor includes two branches capable of pushing in the same time in the head of the implant-holder, two loaders on which are loaded both anchoring devices.

According to another feature of some embodiments, means for grasping an implant are configured for cooperating with at least one hooking-up means of said implant.

According to another feature of some embodiments, the surgical instrumentation may include a tool for withdrawing the anchoring device comprising a hooking-up means for an end of the withdrawal tool which is configured for hooking up the anchoring device, so that traction on the tool allows the latter to be withdrawn from its passage in the implant.

According to another feature of some embodiments, the tool is configured for accessing the hooking-up means of the anchoring device via a means for accessing an implant.

Another purpose of some embodiments incorporating various technical features described in this application is to mitigate at least one of the disadvantages of the prior art by providing a system of rachidian (spinal) surgery for implantation and fixation of rachidian (spinal) implants.

This purpose is furthered with a rachidian surgery system that includes at least one anchoring device and at least one spinal implant, at least one locking means allowing said anchoring device to be locked relative to the spinal implant for ensuring stabilization of the latter in a vertebra.

According to another feature of some embodiments, the rachidian surgery system may include at least one instrument from implantation instrumentation.

BRIEF DESCRIPTION OF THE SEVERAL VIEWS OF THE DRAWING

Various particularities of various embodiments of the present disclosure will become more clearly apparent upon reading the description hereafter, made with reference to the appended drawings, wherein:

FIGS. 2A and 2B respectively illustrate a partial sectional view along the plane 2A-2A of FIG. 2B and a rear view of an implant provided with attachment means according to an embodiment of this disclosure, FIG. 2C illustrates a perspective view of an attachment device according to an embodiment of this disclosure and FIG. 2D illustrates a perspective view of a locking device according to an embodiment of this disclosure;

FIG. 4B illustrates a rear view of an implant provided with attachment devices according to an embodiment of this disclosure, FIGS. 4A, 4C and 4D illustrate partial sectional views, along the sectional plane 4ACD-4ACD of FIG. 4B, of three alternatives of this embodiment of this disclosure, FIGS. 4E and 4F illustrate perspective views of an attachment device, of the alternatives of FIG. 4C and of FIG. 4A, respectively and FIG. 4G shows a perspective view of a locking device according to an embodiment of this disclosure;

FIG. 14C illustrates a rear view of an implant provided with attachment devices according to an embodiment of this disclosure, FIGS. 14A, 14B and 14E illustrate partial sectional views, along the sectional plane 14A-14A of FIG. 14C, along the sectional plane 14B-14B of FIG. 14C and along the sectional plane 14E-14E of FIG. 14A respectively of this embodiment of this disclosure, FIGS. 14D, 14G and 14F illustrate perspective views, of an attachment device, of a locking device and of a means for retaining the locking device respectively according to this embodiment;

FIGS. 18A and 18C respectively illustrate a sectional view along the sectional plane 18A-18A of FIG. 18C and a rear view of an implant provided with attachment devices according to an embodiment of this disclosure, FIGS. 18D, 18E and 18F illustrate partial sectional views along the sectional plane 18DEF-18DEF of FIG. 18A, of three alternatives of this embodiment of this disclosure, FIG. 18G illustrates a profile view of a locking device according to this embodiment and FIGS. 18B, 18H and 18I illustrate views of a locking device, a perspective view according to the alternative of FIG. 18D, a profile view according to the alternative of FIG. 18F and a profile view according to the alternative of FIG. 18E, respectively;

FIGS. 22B, 22C and 20D illustrate this same implant during ablation of one of the attachment devices by a removal tool;

DETAILED DESCRIPTION OF VARIOUS EMBODIMENTS

Figure 1A:
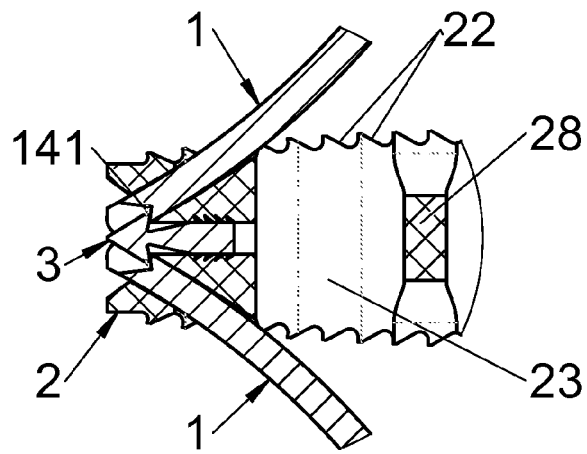
FIGS. 1A and 1B respectively illustrate a partial sectional view along the plane 1A-1A of FIG. 1B and a rear view of an implant provided with attachment devices according to an embodiment of this disclosure.
Figure 1B:
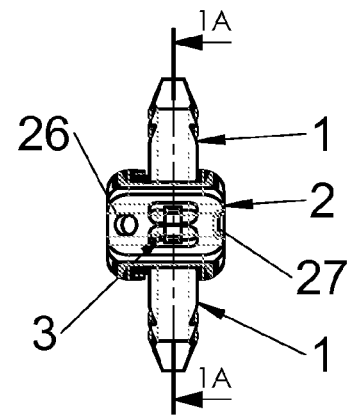
Figure 1C:
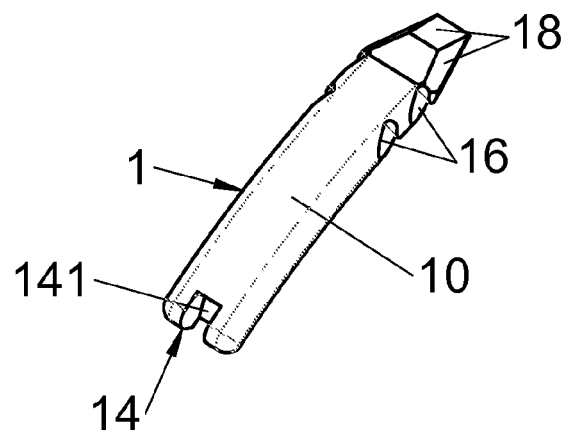
FIG. 1C illustrates a perspective view of an attachment device according to an embodiment of this disclosure and FIG. 1D illustrates a perspective view of a locking device according to an embodiment of this disclosure.

Various embodiments of this disclosure will now be described with reference to the figures of the present application, which among other subject matter are mostly directed to 3 groups of objects and various combinations thereof:
- anchoring devices (1) (or "attachment devices" or further "anchors"), and/or anchoring systems including several anchoring devices (1) which may be identical or different, or even complementary to each other;
- intervertebral implants (2) laid out for receiving one or several of such devices (1) or anchoring systems, including but not limited thereto, intersomatic cages configured for an implantation through a posterior or transforaminal route;
- instrumentation (3, 4, 5) for implanting these implants (2) between the vertebrae and attaching them with such devices (1) or anchoring systems.

Each of these groups of objects may include various possible embodiments relating to a given object. Each of the objects include various elements (generally making up the object) having at least one technical feature. An object (of a given group) may be concerned by at least one technical feature may be associated with at least one other object (of the same or of another group), for example with respect to at least one complementary technical feature, so that the object groups share a common concept. The present disclosure may therefore also relate to an assembly comprising at least 2 of these objects, as well as each object individually. The various elements (for example, a plate, an abutment, a slot, a chamfer or bevel, etc.) as well as their technical features (for example a curvature, an orientation, a length, a width, a height, etc.) are described in greater detail hereafter in the present application. At least one technical feature (or combination of features) for example corresponding to an element of a given object generally address at least one technical problem, for example from among those mentioned in the preamble of the present application. The present application therefore describes various embodiments or configurations for each object or group of objects, for example by specifying at least one technical feature of at least one element. It will be understood upon reading the present application that each of the technical features of each element, described in at least one embodiment or one configuration, may be isolated from the other features of the relevant object (or of the relevant and/or associated objects) by said embodiment or said configuration (and therefore relating to the same element or a different element) and/or may be combined with any other technical feature described herein, in diverse embodiments or configurations, unless the other way round is explicitly mentioned, or that these features are incompatible with each other and/or that their combination does not work, for example because the structural adaptations which may be required by such isolation or combination of features, may be directly derived from the appreciation of functional considerations provided in the present application. Also, although certain technical features are discussed herein with reference to the anchoring device, they may be incorporated in various embodiments or configurations of the anchoring systems. Generally, the specific technical feature(s) relating to a given element should not be considered as exclusive from those relating to another element, nor other technical features relating to the same, except when it clearly appears that the combination is impossible or non-functional. Although the present application details various embodiments or configurations of this disclosure (including preferred embodiments), its spirit and its scope should not be limited to the given examples.

Various embodiments of anchoring devices (1) according to the present disclosure may be used with intervertebral implants (2), which may be for example, such as intersomatic cages (cages for replacing an intervertebral disc in order to achieve arthrodesis), corporectomy cages (cages for replacing a vertebral segment for achieving arthrodesis) or intervertebral disc prostheses (a prosthesis for replacing an intervertebral disc for preserving a certain motional degree of freedom) or even osteosynthesis plates (plates attached on the vertebrae for achieving arthrodesis). Other uses of the anchors (1) may of course be envisioned if the features of the anchor are compliant with functional definitions provided in the present application. The intervertebral implants are generally intended to be implanted between two adjacent vertebrae of the spinal cord (rachis) or to provide a junction between two vertebrae, on their periphery in the case of osteosynthesis plates (which may be used alone or associated with an intersomatic cage for example). The anchoring device (1) is intended to be anchored in one of the vertebrae so as to attach the implant on/against this vertebra. Various embodiments of anchoring devices (1) according to this disclosure include at least one stiff plate, preferably curved (but not necessarily), laid out in order to penetrate into a vertebra through an implant for retaining this implant against this vertebra. The technical features of "curvature" and of "stiffness" concerning the "plate" element of the "anchor" object are described in more detail hereafter. The device (1) for anchoring an intervertebral implant (2) in the vertebrae is sometimes designated in the present application under the term of "anchor" (1) with reference to its anchoring function, without inducing any limitation. Various embodiments of anchors have been described in the published applications WO 2008/149223, WO2011/080535 and WO2013124453 filed by the applicant of the present application, but the present application provides various embodiments which may improve the solutions provided by these applications and which may be more easily applied to any implant, for example a spinal implant (the term spinal being used here is identical with rachidian or vertebral) but possibly with other applications. Thus, the present disclosure provides improvements of various structures and methods which may be used in diverse applications for reducing the invasivity of the operations required for implanting the implant and the anchor and for improving the reliability of the proposed solutions.

In various embodiments, the anchor (1) includes a body comprising at least one plate (10) preferably a stiff plate, elongated along a longitudinal axis. This longitudinal axis of the anchor (1) extends between a first end, designated here as an "anterior end", intended to penetrate into a vertebra and a second end, designated here as a "posterior end". It will be noted that the designations of the "posterior" and "anterior" ends of the anchor (1), of the implant (2) and of the instrumentation (4, 5, 8) are used in the present application with reference to the direction along which the anchor (1) is inserted. Thus, for the anchor (1), the first end, a so-called anterior end, is the one intended to be inserted first and intended to penetrate into a vertebra for attaching an implant. As regards the implant, its wall or its end designated as posterior is the one including an aperture of a passage for inserting the anchor, whether this wall is actually posterior to the implant or not during its deployment. In the case of intersomatic cages (2) or disc prostheses or plates described in the present application, this posterior end may actually be positioned towards the rear of the patient or not, notably for cages which are generally intended for implantation through a posterior or transforaminal route. As regards the instrumentation, the so-called anterior end is the one intended to be in abutment on (or at least the closest to) the implant during implantation.

Certain embodiments of implants (2), including certain embodiments detailed in the present application and relating to an intersomatic cage (2), are laid out for insertion into the discal space through a transforaminal route and the posterior end will therefore be positioned on a lateral and rear side of the vertebrae while the anterior end will be positioned in proximity to the opposite front and lateral side. Nevertheless, the terms of "anterior" and "posterior" are actually used here since they are easier to understand from a point of view of the implantation and may practically and commonly be used with the anchor (1), with the implant (2) and with the instrumentation (4, 5, 8), regardless of the selected implantation route. Therefore, the terms of "anterior" and "posterior" are not intended to simply refer to the patient or to one of his/her anatomic features, but may in some circumstances instead refer to the direction of insertion of the anchor into the implant (regardless of whether this implant is itself implanted along an antero-posterior axis or not). On the other hand, the dimensions of the elements along an orientation parallel to the axis of the rachis (once implanted therein) are generally designated here with the terms of "height" and "thickness", and the terms of "upper" and "lower" (or above and below) are generally also defined according to this orientation (a vertical orientation when the patient is standing), without any limiting implication for this disclosure. Also, the terms of "vertical" and "horizontal" are used in a non-limiting way with reference to the axis of the rachis by considering that the patient is standing. Generally, depending on context the dimensions along a plane perpendicular to the axis of the rachis (a transverse plane) with the width being generally in the medio-lateral direction while the length will be in the antero-posterior direction, will be designated by the terms of "width" and "length", without this conventional definition having any limiting implication for this disclosure. It will also be noted that reference is made here to a longitudinal axis between two ends and that this longitudinal axis possibly corresponds to an antero-posterior axis of the anchor (1), but this axis is in fact generally oblique since the anchor is often inserted from the periphery of the rachis into a vertebral structure (most often a vertebral body and generally in a vertebral plate). Further, this axis of the anchor may even follow a curved path in many embodiments and depending on context it is may be designated as being antero-posterior relative to the end of the anchor rather than with reference to the rachis. Also, the axis of the passage generally is designated by using the same references while it is oblique and while it may be curvilinear or rectilinear. It will also be noted that this definition generally also extends to the implant (2) and to the instrumentation (4, 5, 8), with reference to the direction of insertion of the anchor (1). It will also be noted that the term "substantially" is regularly used in the present description, notably relating to a feature such as an orientation or a direction, so as to indicate that the relevant feature may in fact be slightly different and not be exactly as designated (for example, the expression "substantially perpendicular" should be interpreted as being "at least approximately perpendicular" since it may be possible to select an orientation which is not exactly perpendicular in order to be able nevertheless to substantially fulfill the same function). Further, the terms such as the term of "substantially" used in the present application may also be interpreted as defining that the technical feature may "in general" ("generally") and often "preferably" be as indicated, but that other embodiments or configurations may be within the scope of the present disclosure.

Certain embodiments of the present disclosure relate to one or several bone anchoring (or attachment or anchor) devices (1) for an implant (2) (typically a spinal implant) laid out for being inserted through a passage crossing at least one portion of the implant (2), from an outer surface (e.g. peripheral, anterior, posterior, lateral, upper or lower surface) to a bone contact (typically vertebral contact) surface of the implant. The anchoring device (1) generally includes a body comprising at least one substantially stiff plate (10) elongated along a longitudinal axis extending between an anterior end and a posterior end, the plate (10) being configured so that its anterior end penetrates into at least one vertebral surface while its posterior end remains in the passage of the implant (2), while retaining said implant (2) against said vertebral surface. Generally, an anchor according to various embodiments is laid out so that it may replace the attachment means conventionally used in the prior art, such as screws or staples. Typically, these anchors are generally formed with at least one element with the shape of a plate (for example a T-shaped, V-shaped or L-shaped plate or two of them, or three U-shaped plates or even four of them, for example forming a tube with a square or rectangular section, etc.) and often do not require additional structures penetrating into the vertebrae. Indeed, the plate shape may provide an effective two-dimensional surface for opposing movements perpendicular to this surface and by having at least two plates (providing a three-dimensional structure), it is possible to even better oppose movements in several directions. Thus, the plate(s) of the anchor may have their posterior end substantially inside the implant once they are completely inserted into the implant and they fix the latter to a bone structure. The term of "substantially" is used here in order to emphasize the fact that the anchor may ("slightly") jut out of the implant, in a way which is not significant relative to the dimensions of the anchor and/or of the implants and/or which does not have a (too significant) risk for the surrounding physiological structures of the patient.

Abutments of the locking device and abutment of the anchoring device:

The anchoring device (1) according to various embodiments of this disclosure typically includes at least one abutment (14) (sometimes limited to a single surface) being complementary to an abutment (31) (or also a surface) of a locking means (or device) (3) laid out for locking the anchor (1) relative to the implant (or vice versa). The abutment (14) of the anchor preferably comprises at least one abutment surface (141, 142) oriented non-parallel to the longitudinal axis (of the anchor), in order to effectively oppose movements of the anchor along this longitudinal axis. This (or these) surface(s) (141, 142) is (or are) complementary to at least one abutment surface (311, 312) of the locking means (3) of the device (1) relative to the implant (2). This locking means (3) is located on or in the actual implant. Indeed, in order to address one or more problems of the prior art, the present disclosure provides new layouts of the anchors, implants and instrumentations, for example by providing a locking means (or device) (3) which equips the actual implant ("equips" meaning here both that the locking means may be distinct from the implant or integrated therein, or even in one piece with the latter, or provided secured to the latter, although it is generally preferred that it should be distinct and housed inside the implant). This locking means (3) thus may provide certain advantages depending on the particular embodiment (most of them are detailed hereafter), and often may address at least one part of one or more of the problems mentioned in the present application. This locking means (3) preferably comprises a body retained in the implant and provided with at least one flexible portion (30) and with at least one abutment (31) cooperating with said abutment (14) of the device (1), generally by contact of their mating or complementary abutment surfaces (141, 142, 311, 312) for locking the device (1) relative to the implant (2). In various embodiments, one benefits from this flexibility which allows that the locking means facilitates the passing of the anchor before its abutment engages with the complementary abutment of the anchor. For example, the insertion of the anchoring device (1) in the passage (in which the locking means juts out at least slightly) gives the possibility of pushing back said abutment (31) of the locking means (3) and also allows mutual engagement of both abutments (14, 31) of the anchor and of the locking means (3), when they are found facing each other, by the elastic return of the flexible portion (30). In another example, as detailed further on, it is possible to push the locking means with means other than the actual body of the anchor, such as for example by means of a tool, and when the action exerted on the locking means is released, the latter locks the anchor brought into its final position in the implant.

Also, the spinal implant (2) according to various embodiments of this disclosure includes at least one vertebral contact surface through which the implant (2) is intended to be placed in contact with at least one vertebral surface and at least one outer surface (for example a peripheral, lateral surface or even one inside the discal space, the term of outer being used in reference to the fact that the anchor penetrates into the vertebra from the outside of the implant by entering through this surface and passing through the inside of the implant). This spinal implant (2) may be configured so as to receive at least one anchoring device (1) according to various embodiments of this disclosure or within the scope of the claims, by means of at least one passage crossing at least one portion of the implant (2) along a so-called insertion axis, from said outer surface to said vertebral contact surface. Further, as detailed above, the implant (2) preferably includes at least one locking means (3) of the device (1) relative to the implant (2). This locking means (3) comprises a body retained in the implant and provided with at least one flexible portion (30) and with at least one abutment (31) or surface for stopping the anchor (1) in the implant (i.e. opposing the movement of the anchor in at least one direction substantially parallel to its longitudinal axis or substantially tangential to its curvature). This abutment (31) of the locking means (3) preferably comprises at least one abutment surface (311, 312) oriented non-parallel with the insertion axis of the passage (or with the longitudinal axis of the anchor, generally collinear with the insertion axis, at least approximately). The abutment (31) of the locking means (3) typically cooperates with the abutment (14) of the attachment (or anchoring) device (1) by means of the contact of their complementary abutment surfaces (141, 142, 311, 312) for locking the device (1) relative to the implant (2). As explained above, the flexibility of said flexible portion (30) allows the locking means to be pushed back so that it does not jut out in the passage of the implant upon inserting the anchor. For example, the insertion of the anchoring device (1) into the passage pushes back said abutment (31) of the locking means (3), preferably into a housing provided in the implant. On the other hand, this flexibility typically allows mutual engagement of both abutments (14, 31) when they are found facing each other, by the elastic return of the flexible portion (30) to its initial position, in which at least one portion of the locking means juts out in the passage of the implant intended to receive the anchor.

It will be noted that the term of flexible is used here for designating the fact that the locking means passes from a rest configuration to a flexed or twisted configuration while returning to the rest position or to a position close to the rest position. The present application details how this flexibility (or rather elasticity as detailed hereafter) may be obtained in various embodiments and it will be understood that this relative term finds its definition in the fact that a bolt (locking means or device (3)) capable of undergoing flexure or torsion and of returning to its initial position (e.g. rest position) or at the very least approximately to its initial position (if it deforms plastically, it will have been provided that this is negligible for the locking function) is generally used. Further, it is generally selected in a stiff and sturdy material capable of bearing strong stresses which may be exerted thereon when it locks the anchor (1). Thus, a locking means in metal preferably biocompatible such as titanium for example is preferred and generally an alloy is used. In order to provide the desired flexibility, one therefore acts on the elasticity of a portion of the lock, i.e. it is equipped so that its elastic limit will not (or slightly) be exceeded in order to avoid irreversible deformation (accompanied by a failure for a fragile material or by plastic deformation for a ductile material). It is therefore understood that the term of flexibility generally is used here in the sense of elasticity by preferably providing that the latter remains with values less than the elastic limit of the bolt, for example by resorting beforehand to buckling, creep, compression, torsion, flexure, shearing measurements, etc. Further, this relative flexibility is generally allowed by the sufficiently fine dimensions of the flexible portion and by the fact that the bolt is in fact retained by or secured to (or held fixed or in one piece) the implant on a portion and that the portion(s) forming the abutment(s) have a possibility of displacement in the implants, due to the fact that beyond the portion retained by or secured to the implant, the other so-called free portions, of the locking means (comprising the flexible portion and the abutment) have at least one degree of freedom (non-parallel to the axis of the anchor and of its passage in the implant), by the fact that the implant includes a housing, the size of which at these free portions is greater than the size of these free portions. This layout is advantageous in many embodiments and the bolt is generally dimensioned according to its material for allowing flexure/torsion with return since the bolt is thereby secured in the implant. Further, in various embodiments, the free portions in the implant (2), only have a single degree of freedom not parallel to the axis of the anchor (1), which gives the possibility that the bolt (3) once engaged with the anchor (1), cannot move in the direction of the withdrawal or advance of the anchor, thereby securing the locking of the latter.

This type of layout of the anchor and of the implant comprising a locking means may provide certain advantages. Indeed, by the fact that the implant comprises a locking means, various embodiments of this disclosure give the possibility of optimizing the invasivity and/or reliability of the system, since the anchor may be of more reduced size than in the absence of a locking means provided in (or on) the implant. Conversely, the abutments used, and especially the elastic mechanism (flexibility) of mutual engagement may be of larger dimensions, without undue congestion and/or invasivity of the anchor. Thus, the system may be more reliable since the anchor may be effectively locked with abutments of satisfactory dimensions, which typically may be greater than those known from the prior art. Indeed, it is often advantageous to provide an efficient locking mechanism since the anchors according to various embodiments of the present disclosure sometimes are generally only retained by this mechanism, unlike other anchoring devices known from the prior art. That can enhance reliability and provide additional advantages, like the cost and the simplicity of application for example. Thus, in the present disclosure, provision is generally made for a locking means with suitable dimensions and layout for being subject to significant stresses, for example as detailed in the present application.

Moreover, this type of layout of the locking means may provide the additional advantage of allowing that the abutments be provided in a solid material, even if the implant is in a more flexible material. Indeed, for example in the case of intersomatic cages, it is frequent that the material be relatively soft, for example PEEK (acronym of polyetheretherketone). On the other hand, the bone anchoring devices should generally be of a solid material, notably when they are intended to be directly planted into the bone without making a housing beforehand for receiving them. Thus, the use of a device in a stiff material which will bear impaction in the bone and which will provide good stability, such as for example titanium, is preferred. Thus, an anchor in a solid and often stiff material has a risk of damaging the more flexible material of the implant if abutments of the anchor have to be leaning (i.e. in abutment) against structures or surfaces of the implant. Although such structures may be used in various embodiments of this disclosure, in some other embodiments of the present disclosure, this risk is mitigated by allowing the anchor to abut on the locking means. It is then preferably provided that this locking device should also be itself of a solid material, i.e. a material which has a low risk of being damaged by the pressure of the anchor on it. For example a locking means may be selected in the same material as that of the anchor (for example titanium). In addition to avoiding damaging of the implant (which, according to the extent, may jeopardize the whole of the system), this advantage typically is accompanied by increased reliability of the holding of the anchor in the implant.

Figure 3A:
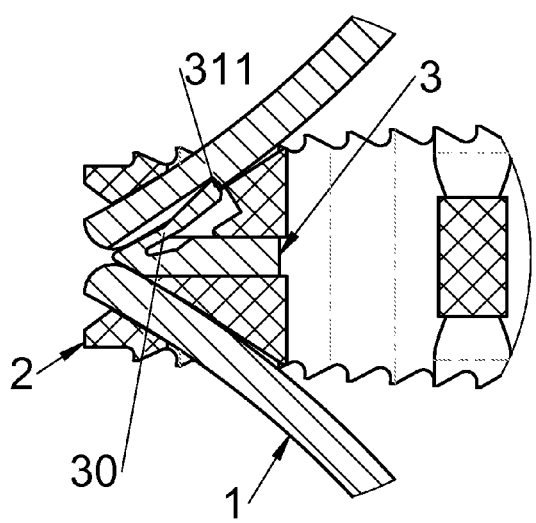
FIGS. 3A and 3C illustrate partial sectional views along the sectional plane 3AC-3AC of FIG. 3B, of two alternatives of this embodiment of this disclosure.
Figure 3B:
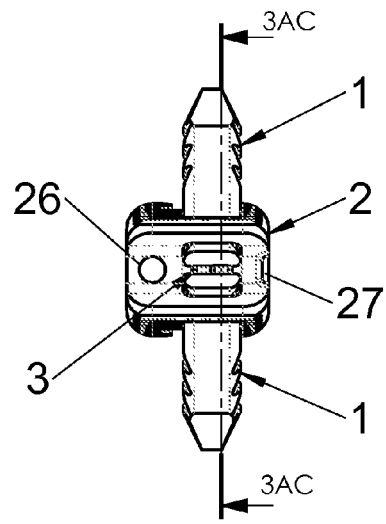
FIG. 3B illustrates a rear view of an implant provided with attachment devices according to an embodiment of this disclosure.
Figure 3C:
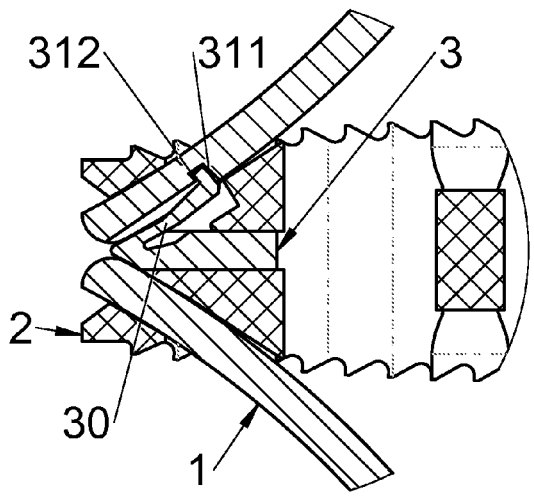

Further, this type of layout gives the possibility that a single and same locking means provide two different types of abutment. Indeed, it is possible to provide a single abutment surface for opposing the movement of the anchor in a single direction (the direction of the penetration into the implant and the vertebra or the direction for withdrawing the anchor out of the implant or the vertebra) or two opposite surfaces for opposing the movement of the anchor in both directions (penetration and withdrawal). Thus, in certain embodiments, said abutment surface (141) present on the abutment (14) of the device is oriented facing the posterior end of the anchoring device (1) so that the abutment (31) of the locking means (3) gives the possibility of opposing the withdrawal of the device out of said passage. Alternatively, said abutment surface (142) present on the abutment (14) of the device is oriented facing the anterior end of the anchoring device (1) so that the abutment (31) of the locking means (3) gives the possibility of opposing an excessive advance of the device (1) in said passage. Advantageously, both of these non-exclusive alternatives may be combined so that the abutment includes both an abutment surface (141) oriented facing the posterior end of the anchoring device (1) and an abutment surface (142) present on the abutment (14) of the device is oriented facing the anterior end of the anchoring device (1). Thus, the locking means (3), with its abutment (31) including surfaces (311, 312) mating these surfaces (141, 142) of the anchor, gives the possibility of opposing both involuntary withdrawal and excessive advance of the anchor. Thus, it is possible to provide that the respective abutments (14, 31) of the anchor (1) and of the locking means (3) oppose the advance and/or withdrawal of the anchor. Indeed, in a complementary manner to the layouts of the anchor described above, said abutment surface (311) present on the abutment (31) of the locking means (3) may be oriented facing the outlet of the passage to the vertebral contact surface in order to cooperate with the abutment surface (141) present on the abutment (14) of the anchoring device (1) and thus oppose its withdrawal out of said passage. The abutment (31) of the locking means (3) may alternatively or additionally have an abutment surface (311) oriented facing the inlet of the passage to the outer surface in order to cooperate with said abutment surface (142) present on the abutment (14) of the anchoring device (1) and for opposing excessive advance of the device (1) in said passage. For example in FIGS. 1A, 2A, 3A and 4A, the abutments only oppose the withdrawal of the anchor. On the other hand, in FIGS. 3C, 4C and 4D for example, the abutments include two substantially opposite surfaces for opposing the withdrawal but also limiting the advance of the anchor. Thus, it is possible to omit means limiting the displacement of the anchor in the implant, even if the provision of such means (generally on the surgical instrumentation) is generally preferred.

Figure 6A:
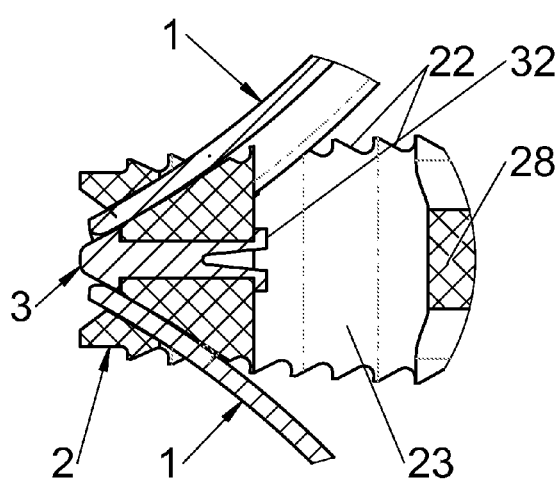
FIGS. 6A and 6C illustrate partial sectional views, along the sectional plane 6AC-6AC of FIG. 6B, of this embodiment of this disclosure respectively according to another alternative and the alternative of FIG. 6B, FIGS. 6D and 6E illustrate profile views of the locking devices according to the alternatives of FIG. 6C and of FIG. 6A respectively.
Figure 6B:
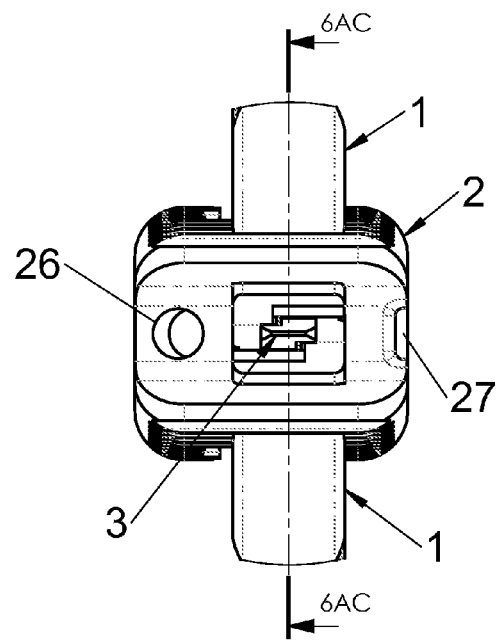
FIG. 6B illustrates a partial rear view of an implant provided with attachment devices according to an embodiment of this disclosure.
Figure 6C:
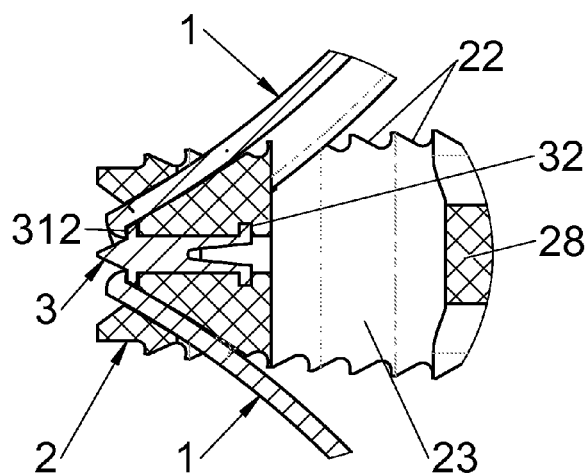
Figure 6D:
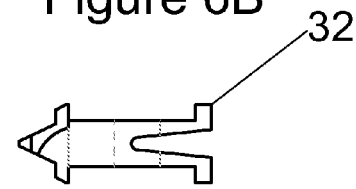
FIGS. 6F and 6G illustrate perspective views of an attachment device and of a locking device respectively according to the alternative embodiment of FIG. 6A.
Figure 6E:
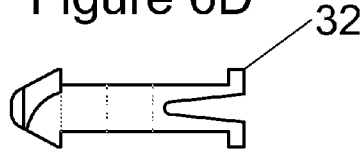
Figure 11A:
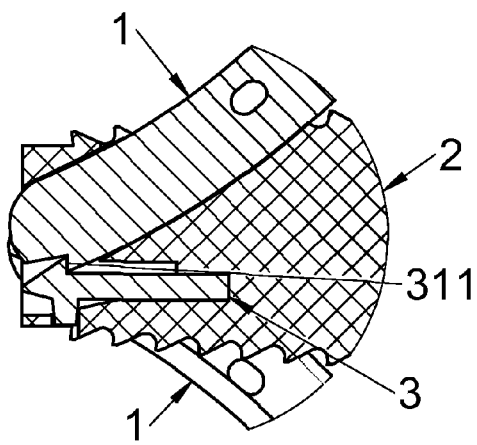
FIGS. 11A and 11C illustrate partial sectional views along the sectional plane 11AC-11AC of FIG. 11B, of two alternatives of this embodiment of this disclosure, FIGS. 11D and 11E respectively illustrate a profile view and a perspective view of an attachment device according to the alternative embodiment of FIG. 11A, and FIGS. 11F and 11G respectively illustrate a profile view and a perspective view of a locking device according to the alternative embodiment, respectively of FIG. 11C and of FIG. 11A.
Figure 11B:
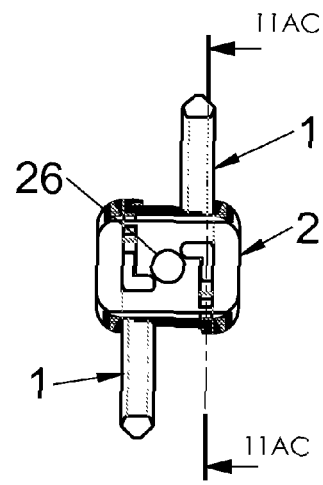
FIG. 11B illustrates a rear view of an implant provided with attachment devices according to embodiment of this disclosure.
Figure 11C:
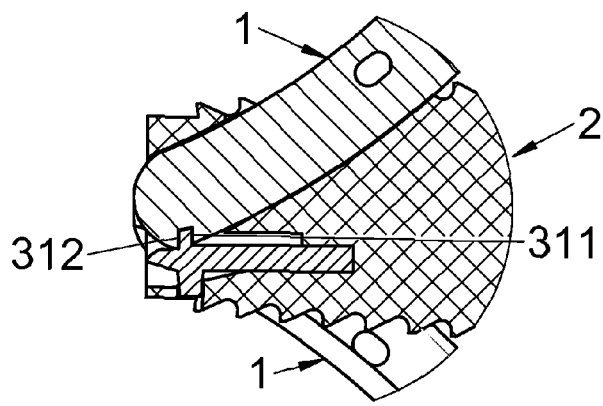
Figure 11D:
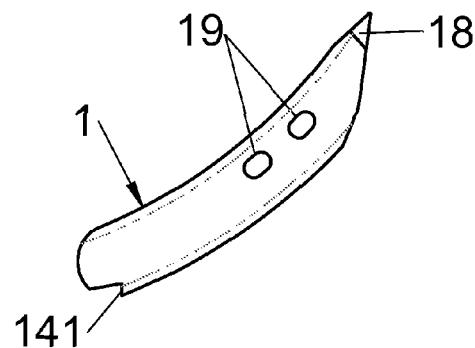
Figure 11E:
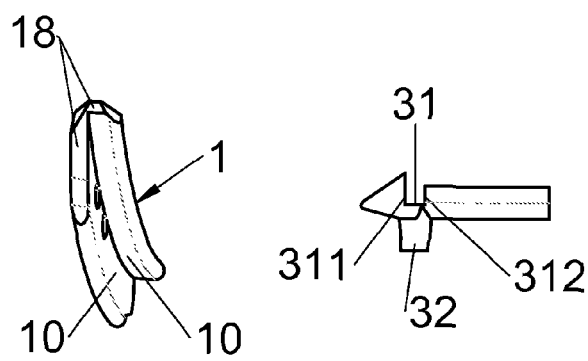
Figure 11F:
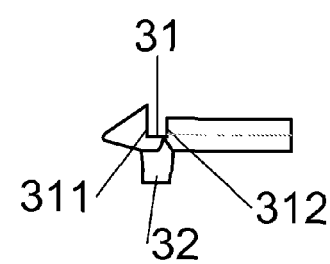

In certain embodiments, said abutment (14) of the device (1) is a female abutment cooperating with a male abutment (31) of the locking means (3). For example, said abutment (14) of the device is a recess, a notch, an irregularity or any other shape dug in a surface of the anchoring device (1), intended to cooperate with a protrusion forming the abutment (31) of the locking means (3). For example, FIGS. 1A, 1C, 2A, 2C, 3A, 3C, 3D, 3E, 4C and 4E illustrate in an illustrative and non-limiting way, various alternatives of such a female abutment of the anchor. Alternatively, in certain embodiments, said abutment (14) of the device (1) is a male abutment cooperating with a female abutment (31) of the locking means (3). For example, said abutment (14) of the device (1) forms a protrusion jutting out from a surface of the anchoring device (1) and intended to cooperate with a recess in a surface of the locking means (3). The shape of such a male means, for example forming a protrusion on a surface of the anchor, may vary, as well as the position of this male means on the anchor, may also vary according to various embodiments. FIG. 4D shows an example of such a male means of the anchor engaging into a female means of the locking device (or means) (3). This example is of course non-limiting and one skilled in the art may provide various shapes and layouts of such a male means. On the other hand, in certain embodiments, the abutment (14) of the device is formed by a surface of the posterior end of the plate (10) which is made so as to sufficiently penetrate into the implant (2). For example, one then has an end of the plate, which may be considered as a male or female means, and a shoulder on the locking means, which may be considered as a female or male means. For example, in FIGS. 4A, 4F and 6A, it is on the surface of the posterior end of the anchor that the abutment of the anchor is formed. Indeed, the locking means, such as for example visible in FIGS. 4G and 6G, includes an abutment surface (311) which is intended to be put into contact with this posterior end in order to oppose the withdrawal of the anchor (1). It is understood that in such embodiments, only the withdrawal of the anchor (1) is prevented, but the advance (penetration) of the anchor is not limited by the abutment of the locking means (3). In a complementary way to the alternatives of the anchor above, the abutment (31) of the locking means (3) may be a female abutment cooperating with a male abutment (14) of the device (1). For example, said abutment (31) of the locking means (3) is formed by a recess or housing in a surface of the locking means (3), intended to cooperate with the abutment (14) formed by a protrusion jutting out from a surface of the anchoring device (1). FIG. 4D shows an example of a housing in a tab of the locking device, intended to receive a lug of the anchor. Also, FIG. 11F shows another example of a housing in the locking means, intended to receive a protrusion of the anchor (not shown). In the same way as for the examples provided above for the anchors, these examples for the locking means are purely illustrative and are not limiting. On the other hand, as mentioned above, the abutment (31) of the locking means (3) may be a male abutment cooperating with a female abutment (14) of the anchoring device (1). For example, said abutment (31) of the locking means (3) forms a protrusion intended to cooperate with the abutment (14) of the device formed by a recess in a surface of the anchoring device (1). FIGS. 11A and 11C show examples of such male abutment means (31) on the locking device (3). It will be further noted that such male abutments (31) may also be formed by the body of the locking means (3) itself, instead of being formed by a protrusion on one of its surfaces. Indeed, in certain embodiments, the locking means includes a body, a flexible portion of which allows a portion of the body to form the abutment. For example, in FIGS. 12G, 13D, 14G, 15F, 16F, 18B, 18H, 18I and 19F, the abutment (31) of the locking means is formed by a portion of the body of this locking means and does not require that a structure be made at its surface. This type of layout may be advantageous since it provides a solid abutment which may better withstand the forces exerted thereon than would a small protruding element from a surface.

It will be noted that various embodiments of the complementary abutments of the anchor and of the locking device selectively give preference to retaining the anchor in the implant (by at least one abutment opposing the withdrawal of the anchor) or to retaining the implant against the bone in which the anchor is intended to penetrate. Indeed, an abutment opposing the advance of the anchor beyond a certain distance in the implant has the additional effect of flattening the implant against the bone. The implant is then firmly fixed against the bone (for example, the vertebra). On the other hand, an abutment opposing the withdrawal of the anchor (a so-called withdrawal abutment) prevents it from leaving the bone, but may have the effect of pulling on the implant if it is caused to be subject to the forces tending to have it move out of the bone. Nevertheless, various embodiments provide that the orientation of the anchor in the passage and the orientation of the withdrawal abutment surfaces are such that movements in the direction of the withdrawal of the anchor do not or slightly induce movement of the implant. For example, the oblique and/or curvilinear path of the anchor in the implant prevents the anchor from moving the implant and on the contrary allows it to be still better firmly maintained against the bone. On the other hand, it is generally preferred to have at least one withdrawal abutment in order to avoid the possibility of the anchor leaving the bone and the implant as long as this has not been decided. Indeed, it is not absolutely necessary to have an advance abutment (penetration) since the implant is often maintained by the anchor so as to be sufficiently stable, by the oblique orientation of the latter (relative to the axis of the rachis), or even by its curvature in certain embodiments. Also, rather than an advance abutment, it is possible to provide thickening of the plate of the anchor in proximity to its posterior end so that the thickness is substantially equal or slightly greater than the width of the passage, so as to thereby obtain blocking of the advance of the anchor in the implant and to ensure that the implant is properly maintained against the bone, without requiring an abutment not parallel to the longitudinal axis of the anchor. Nevertheless, it is sometimes possible to provide at last one advance abutment, limiting the displacement of the anchor in the implant and allowing the implant to be firmly maintained against the bone, without providing any withdrawal abutment, for example when the orientation of the anchor in the implant and relative to the bone is such that the risk of spontaneous withdrawal is very limited. However, it is generally preferred to have both types of abutments for firmly maintaining the implant and for mitigating anchor movement out by itself under the action of the forces exerted thereon. Various embodiments of the present disclosure, as explained above with reference to the abutment surface (141, 142) of the anchor, therefore include abutment surfaces (311, 312) of the locking means which are complementary to the abutment surfaces (141, 142) of the anchor (1). These embodiments therefore give the possibility of dual locking (advance and withdrawal) of the anchor, which is advantageously obtained with a single locking means (3).

Attachment/Anchoring Device or Anchor:

As explained above, the attachment device (1) typically includes at least one relatively stiff plate (10) allowing firm attachment of the implant to the bone structure with which it should be in contact (generally the vertebral body in the present application). In various embodiments, this plate is curved and complementary to the shape of the passage of the implant (2) so as to cross the implant without any deformation and to be inserted therein along an axis not perpendicular to the vertebral surface into which the anterior end should penetrate. The term "stiff" is therefore used here for specifying that the anchor should preferably pass through the implant without having to be subject to elastic deformation or any deformation. Further, by this, it is understood that it typically may provide sufficient stiffness and robustness for withstanding the stresses which will be exerted thereon, without deforming or at the very least without deforming in a too substantial way. The passage in the implant may then, for receiving this curved anchor, be preferably curved, but it may be rectilinear provided that its dimensions are adapted to those of the anchor and to the radii of curvature of the latter. One alternative, generally preferred, consists in a passage comprising two rectilinear portions with different orientation so that the walls of the passage are substantially tangent to the radius (radii) of curvature of the anchor. This layout may be advantageous for maintaining the anchor (more than a single rectilinear portion) and for ease of manufacturing (costs). In certain of these embodiments, the body of the anchor (1) describes at least one circular or elliptical arc having dimensions and at least one radius of curvature, produced so that the anchoring device (1) is implantable in a vertebral plate along an approach axis forming with the vertical axis of the rachis an angle of approximately 90°, exhibiting its longitudinal axis substantially in the plane of the intervertebral space. In a complementary way to the curved anchor, said passage is rectilinear or curved and complementary to the shape of the curved anchoring device (1) so as to allow the passage of the anchoring device (1) through the implant without any deformation, by insertion along an axis not perpendicular to the vertebral surface into which the anterior end should penetrate. This type of curved anchor may give the possibility of limiting congestion and invasivity by limiting the required room around the implantation site.

Figure 17A:
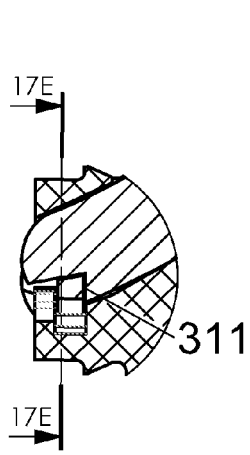
FIGS. 17A, 17B and 17E illustrate partial sectional views along the sectional plane 17AD-17AD of FIG. 17C, along the sectional plane 17B-17B of FIG. 17C and along the sectional planes 17E-17E of FIG. 17A respectively of this embodiment of this disclosure.
Figure 17B:
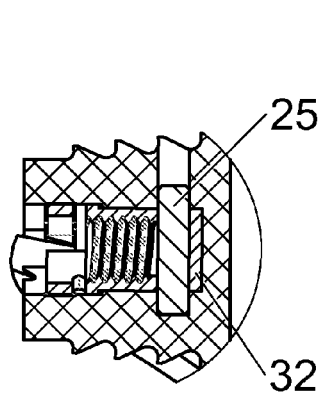
Figure 17C:
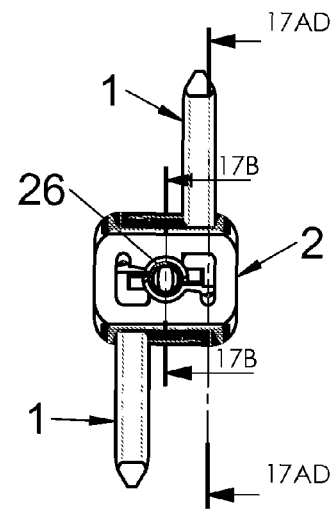
FIG. 17C illustrates a rear view of an implant provided with attachment devices according to an embodiment of this disclosure.
Figure 17D:
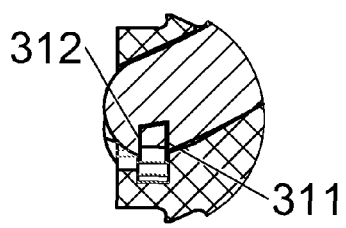
FIG. 17D illustrates a partial sectional view, along the sectional plane 17AD-17AD of FIG. 17C, of an alternative embodiment.
Figure 17E:
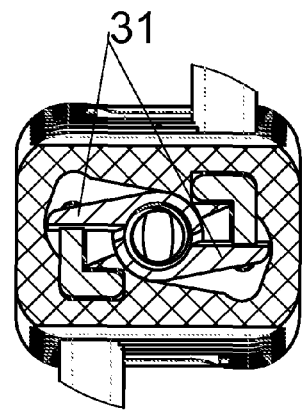
Figure 17F:
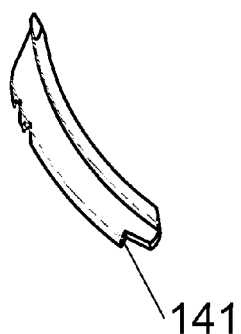
FIGS. 17F and 17G illustrate perspective views, of an attachment device and of a locking device respectively according to the embodiment of FIG. 17C.

In certain typically advantageous embodiments, the anchoring device includes at least two plates (10), for which the longitudinal axes are parallel to each other, but for which the transverse axes are not parallel with each other. Preferably, their transverse axes are perpendicular to each other, giving an L-section to the anchoring device (1), but they may also have an angle different from 90°, for example by giving the device a V-section. Also, it may be contemplated that this is in fact a single and same plate which is curved in this transverse dimension, so that the device has a C-section. This type of layout generally is advantageous since the stiff plates used in various embodiments of the present disclosure are more stable than other less robust attachment means such as nails or staples, but by having an anchor, for which the width (the dimension transverse to its longitudinal axis) has two edges of different orientations (by the fact that it includes two non-parallel plates or a curved plate), it is possible to oppose movements of the anchor in the bone along at least two different directions. Thus, the anchor is clearly stabilized in the bone and may mitigate cutting or snipping the vertebrae by lateral movements. This possibility of providing a second surface opposing the movements along a second direction, is therefore designated here by the term of "two plates" and of "L-section", whether this in fact is a single curved plate or else two plates (with non-parallel but variable orientations, for example as an L or a V). Thus, certain embodiments of this disclosure relate to an anchoring device (1), the body of which includes a second plate (11) elongated along said longitudinal axis of the first plate (10) and extending between the anterior end and the posterior end, the second plate (11) being secured to the first plate (10) and not parallel to the first plate (10), giving the device a section with the shape of an L, V or C, complementary to the internal section of the passage of the implant (2). This advantageous type of layout may be contemplated regardless of the type of abutments used, i.e. either comprising abutments (14, 31) or not, as described in the present application, in cooperation with a locking device (or means) (3). Illustrative and non-limiting examples of such anchors are illustrated in FIGS. 5B, 5C, 6A, 6B, 6C, 6F, 8A, 8B, 8C, 9B, 9C, 9D, 10B, 10D, 10E, 11B, 11D, 12B, 12D, 13B, 14C, 15B, 15D, 15E, 16B, 17C, 17E, 17F, 18C, 18D, 18E, 18F, 19B, 19D, 19E, 20A, 20B, 20C, 20D, 20E, 20F, 21A, 21B, 21C, 21D, 21E, 21F, 22A, 22B, 22C and 22D. Such anchors may have the advantage of being able to reduce congestion in the implant. Indeed, the L, V or C-sections may be useful for surrounding the hooking-up means (26) of the implant, intended to receive a surgical tool such as an implant-holder. Indeed, it is seen in these figures that the implant is thus provided with two anchors, the non-planar sections of which are positioned around the hooking-up means formed by a housing accessible from the outside of the implant. Further, this type of anchors may have the advantage of ensuring stable attachment while limiting the size of the actual anchors. Indeed, both plates of the anchor (1) may have quite small dimensions one like the other, since they cooperate with each other for opposing movements of the anchor and of the implant in two directions (and they do not have to be as wide as in the case of a single plate, even provided with a rib). The passage in the implant (2) has an internal section with a shape mating that of the device. A passage may therefore be provided with inner walls fit the shape of an L, a V or a C, so that it is complementary to the shape of the anchoring device (1), the body of which includes a second plate (11) extended along said longitudinal axis of the first plate (10) and extending between the anterior end and the posterior end, the second plate (11) being secured to the first plate (10) and substantially perpendicular to the first plate (10). This type of L or V or C layout of the anchor (1) also may provide the additional advantage that it is easier to provide at least two anchors for a same implant and notably an anchor for each of the adjacent vertebrae between which the implant is intended to be implanted, without the paths of the anchors crossing each other in the implant, even in the case of curved anchors for which the radius of curvature may be large. Indeed, with not very extended plates (with a small width), it is easier to plan their paths through an implant, even when the size of the implant is small, i.e., congestion is significant. It will be noted that both plates may have the same extent (width) or may be different, such as for example as visible in FIGS. 16B, 17C, 18B and 19B wherein the plate which is oriented vertically is wider than the other one. In these examples of the figures, the anchors are curved and one of the plates (the widest) is curved in the direction of its width, while the other one (the less wide) is curved in the direction of its thickness. Generally the abutment (14) of the anchor is provided on the widest plate, notably when this abutment (14) is a female abutment. However, provision may be made for the same type of dual plate layout as in the case of straight anchors. Also, both plates may have identical length or have different lengths. For example, as visible in the example of FIG. 17F, the plate intended to be oriented vertically (the one curved in the direction of its width) is shorter in order to facilitate penetration into the bone, but it is possible to provide the inverse configuration or even an intermediate configuration in which the portion which forms the junction (the angle) between both plates is the longest. Indeed, it is generally desired to optimize the penetration into the bone and the use of sharpened profiles or bevels is frequent.

Figure 5A:
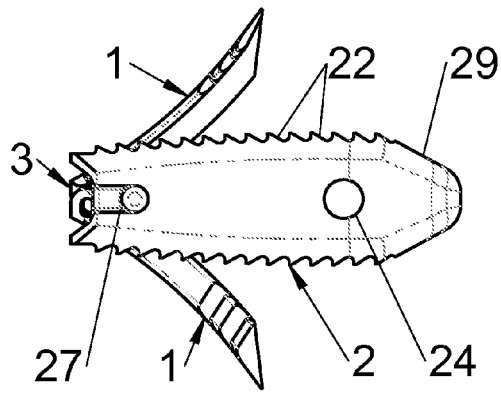
FIGS. 5A, 5B and 5D respectively illustrate a profile view, a partial rear view and a sectional view along the sectional plane 5D-5D of FIG. 5B, of an implant provided with attachment devices according to an embodiment of this disclosure.
Figure 5B:
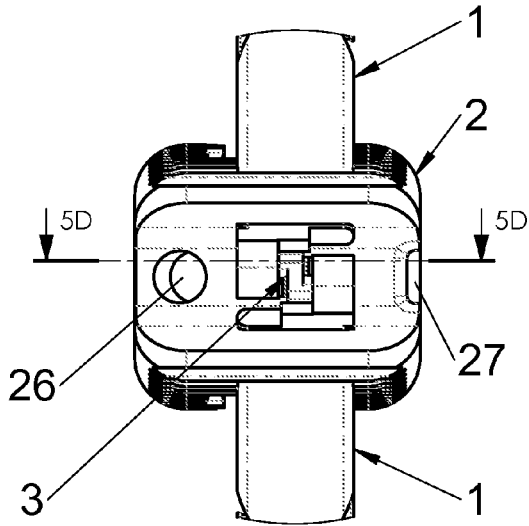
Figure 5C:
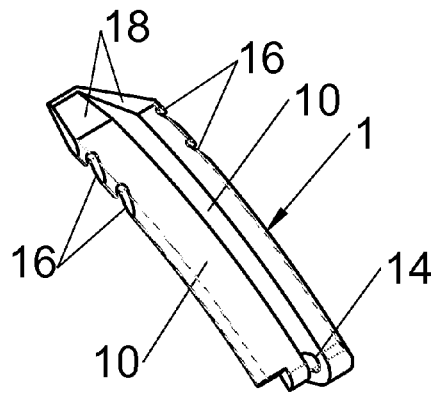
FIGS. 5C and 5E illustrate perspective views of an attachment device and of a locking device, respectively, according to this embodiment of this disclosure.
Figure 6F:
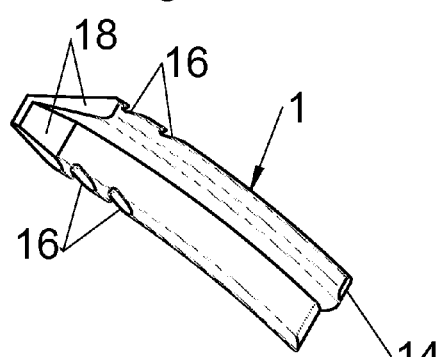
Figure 6G:
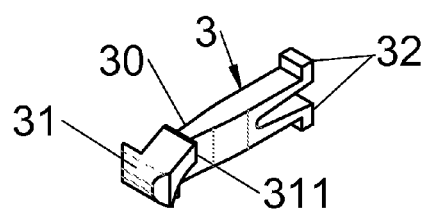
Figure 7A:
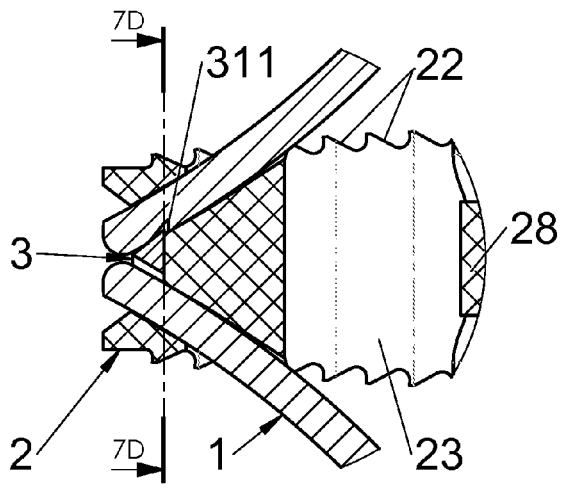
FIGS. 7A and 7C illustrate partial sectional views, along the sectional plane 7AC-7AC of FIG. 7B, of two alternatives of this embodiment of this disclosure.
Figure 7B:
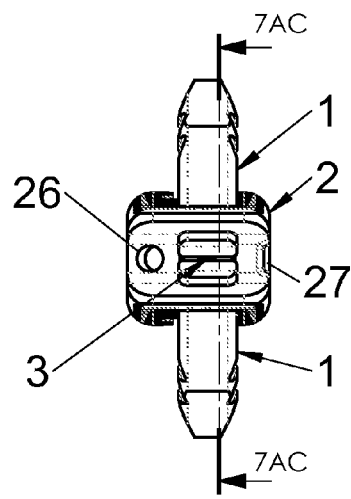
FIG. 7B illustrates a rear view of an implant provided with attachment devices according to an embodiment of this disclosure.
Figure 7C:
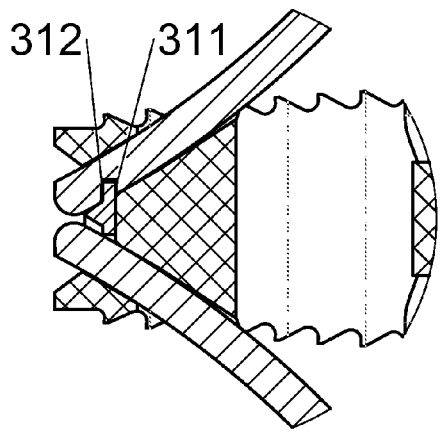
Figure 7D:
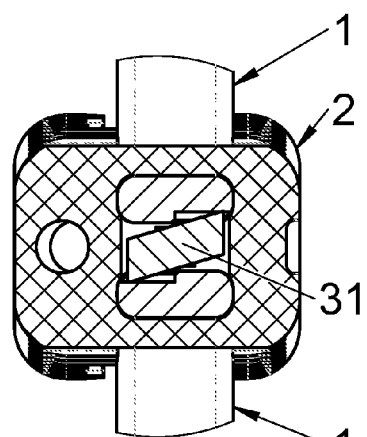
FIG. 7D illustrates a partial sectional view, along the sectional plane 7D-7D of FIG. 7A, of the alternative embodiment of FIG. 7A, FIGS. 7E and 7F illustrate perspective views of an attachment device, of the alternatives of FIG. 7C and FIG. 7A respectively
Figure 7E:
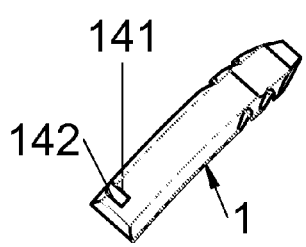
FIG. 7G illustrates a perspective view of a locking device according to the alternative embodiment of FIG. 7A.
Figure 7F:
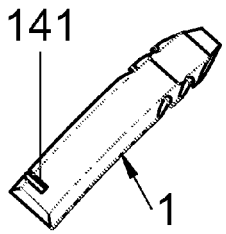
Figure 7G:
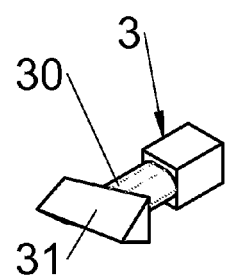
Figure 12A:
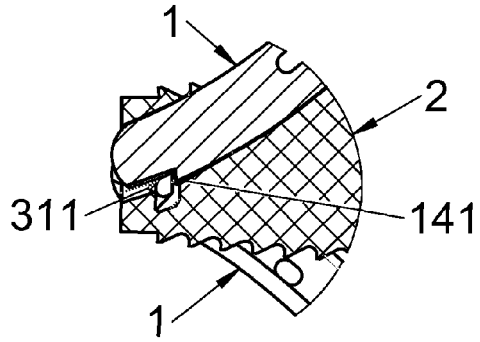
FIGS. 12A and 12C illustrate partial sectional views, along the sectional plane 12AC-12AC of FIG. 12B, of two alternatives of this embodiment of this disclosure.
Figure 12B:
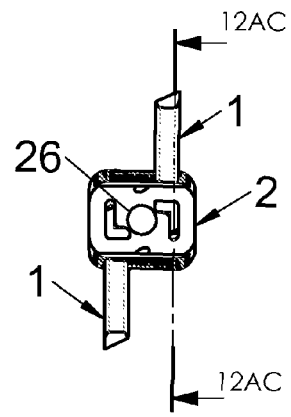
FIGS. 12B and 12E respectively illustrate a rear view and a top view, of an implant provided with attachment devices according to an embodiment of this disclosure.
Figure 13A:
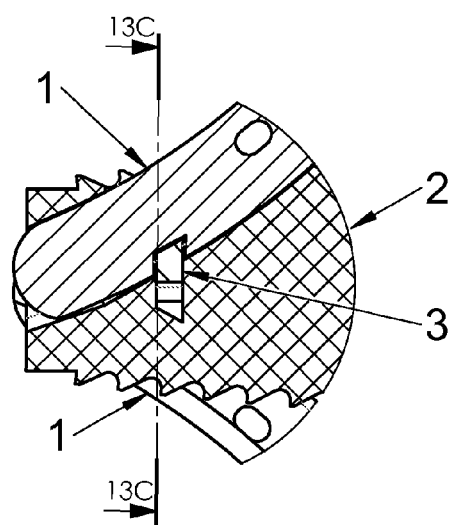
FIGS. 13A and 13C illustrate partial sectional views along the sectional plane 13A-13A of FIG. 13B and along the sectional plane 13C-13C of FIG. 13A respectively of this embodiment of this disclosure, and FIGS. 13D and 13E respectively illustrate a perspective view of a locking device according to this embodiment and a front view of a locking device according to an alternative of this embodiment.
Figure 13B:
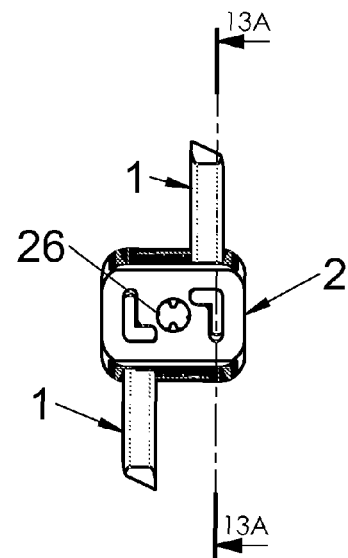
FIG. 13B illustrates a rear view of an implant provided with attachment devices according to an embodiment of this disclosure.
Figure 13C:
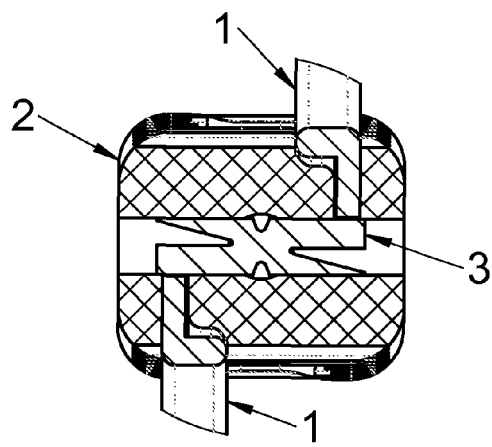

In certain embodiments, the body of the anchor (1) includes, at least at its anterior end, at least one chamfer or bevel (18) facilitating the penetration of the device (1) into the bone (for example the vertebral surface). In the illustrative and non-limiting examples of FIGS. 1C, 2C, 3D and 3E, the anterior end of the anchor includes several chamfers, for example at least one chamfer on at least one of its two upper and lower faces and at least one chamfer on its side edges. Thus, the end is sharpened so as to penetrate more easily into the bone. It is also possible to provide a spiked end, but as the impact experienced upon the anchoring into the bone is significant, it is preferable to avoid having a too fine structure at the anterior end. In the illustrative and non-limiting examples of FIGS. 12B, 13B and 14C, the anterior end of the anchor only includes at least one chamfer on at least one of its two upper and lower faces, but is not sharpened on its side edges. In the examples of FIGS. 12B and 13B, the chamfer is oblique so that the end of the anchor forms an oblique end, while, in the example of FIG. 14C, the chamfer is perpendicular to the longitudinal axis, so as to form a sharpened straight end. In the examples of FIGS. 7E and 7F, the anterior end is not sharpened on its side edges but only at least on one of its two upper and lower faces. In the examples of FIGS. 5C and 6F, the features of which will be detailed later on relative to the layout of the anchor in the form of two perpendicular plates forming between them an L section, the end is sharpened for only one of the two plates, while the other one is left flat, while in the examples of FIGS. 9C, 9D, 10E and 10F, the ends of the two L plates are sharpened. It will be noted that a chamfer of the anchor may have a variable extent from the anterior end to the posterior end. The whole of the above examples show, in a non-exhaustive way, the diversity of the shape possibilities of the anchor, notably as regards its sharpening.

Further, in certain embodiments, the anterior end includes at least one notch (not shown) facilitating penetration of the device (1) in said vertebral surface. Such a notch may also be sharpened in order to further facilitate penetration.

On the other hand, in certain embodiments, the body of the anchor (1) is provided with catches (16) oriented so as to oppose withdrawal of the anchor (1) once it is implanted in a vertebra. Also, such an effect may be obtained, in certain embodiments, by the fact that the body is provided, at the portion intended to penetrate into the vertebral surface, with at least one hole (19) allowing bone growth through the anchoring device (1). Illustrative and non-limiting examples of such bone growth holes (19) are notably illustrated in FIGS. 9C, 9D, 10E, 10F, 11B and 12F. However, the present disclosure also provides many embodiments in which it is preferred to anticipate the possibility of a withdrawal (this withdrawal is often designated by the term of "ablation") of the anchor if need be.

Physical Quantities (Illustrative and Non-Limiting):

In various embodiments, the plate of the curved anchor (1) describes, along the longitudinal axis, at least one circular arc and/or at least one elliptical arc, for which the dimensions and the radii of curvature are such that the anchoring device (1) is implantable in the vertebral plate of a vertebra by having its longitudinal axis substantially in the plane of the intervertebral space, i.e. along an approach axis substantially perpendicular to the axis of the rachis (i.e., said plane or said approach axis being substantially tangent to at least one portion of the anterior end when the anchor moves closer to the vertebrae). Various embodiments of the various objects of the present disclosure relate to the technical characteristic of the radius (or radii) of curvature of the anchoring device (1)). Various embodiments of the anchoring device (1) in fact have a different radius of curvature from one anchor to the other and/or several different radii of curvature on various portions of the body of a given anchor (1). Thus, for example the body of the anchor (1) may have the shape of a circular arc or an elliptical arc, but it may also describe a more complex curvature, such that if several circular arcs, having a same radius of curvature or different radii of curvature, were put end to end or if several elliptical arcs, having a same radius of curvature or different radii of curvature, were put end to end or any combination between circular or elliptical arcs or even a radius of curvature varying along the body. In the present description, the terms of "circular arc" or "radius of curvature" in fact correspond to the whole of these different possibilities. Thus, various embodiments of the present disclosure provide different alternatives as regards the radius of curvature and certain aspects relating to the anchoring device (1), as well as to implants (2) and instruments (4, 5, 8) which may be associated with it. Indeed, for example, depending on the use of the anchoring device (1) and notably on the localization in the rachis for which it is intended, a larger or lesser radius of curvature may be preferred. Depending on the radius of curvature of the anchoring device (1), the axes respectively passing through the penetration end and through the abutment end of the device (1) form an angle, typically comprised approximately between 90° and 180° although it may also be selected to be less than 90°. Preferably, this angle will be comprised between 110° and 160° which, under many circumstances will facilitate implantation of the device (better an angle outside these values). According to the attachment which one desires to obtain by means of the anchoring device (1), a more or less open angle will be selected. If it is for example desired to promote firm and robust attachment of the implant against the vertebral plates, an angle comprised between 120° and 180° may be preferred, while if it is rather desired to avoid displacement of the implant in the plane of the discal space, an angle comprised between 90° and 150° may be preferred. Although these variations of the angle are not illustrated in the figures, different angles for the anchoring device (1) thus give the possibility of covering the different desirable types of anchoring, in order to ensure attachment of the implants adapted according to the case. It is also possible to provide, in one of the preferred embodiments, a device (1) for which the angle is at an optimum value, for example close to 135°, for attaching the device both by firmly maintaining the implants against the vertebral plates and by avoiding their displacement in the plane of the discal space. Further, depending on various embodiments of the implant (2), it is possible to select different angles for the anchoring device (1), notably for allowing proper attachment in spite of a possible lordosis or kyphosis, or even scoliosis, regardless of whether it is natural, pathological or imposed by the implant. Thus, various embodiments of the anchoring device (1) and of the implant (2), thanks to its radius of curvature and to the orientation of the passage of the implant (2) into which it is intended to be inserted, may be implanted along an approach axis substantially in the plane of the intervertebral space, i.e. the plane in which the implant (2) is implanted, which facilitates the approach of the whole of the elements of the implant and of the device around the intervertebral space. In certain embodiments, the arc(s) described by the body of the anchor (1) has(have) dimensions and at least one radius of curvature made in such a way that the anchoring device (1) is implantable in a vertebral plate along an approach axis forming with the vertical axis of the rachis an angle comprising 40° and 140° and, preferably, an angle of approximately 90°. This angle may vary for a same anchoring device (1) depending on the congestion around the vertebrae and may also vary from one anchoring device (1) to the other depending on the radius of curvature of the device (1) used (and therefore on the angle formed between its anterior and posterior ends). Further, various embodiments provide an anchor (1) including at least one straight (not curved) plate (10). It will be noted that in the case of straight anchors (1) (comprising at least one straight plate), the approach axis preferably is not in the plane of the discal space but may be oblique. This type of oblique axis is generally not preferred because of the congestion in accessing the vertebrae but it sometimes remains possible and may be used under certain circumstances. The implants (2) used with such straight anchors (1) will preferably include at least one straight passage (rectilinear) and oriented to at least one vertebra, along an oblique path (non-perpendicular to the axis of the rachis) between the periphery of the rachis and the vertebrae. The instrumentation used with such implants (2) with a narrow passage and with such straight anchors (1) will preferably have a contact surface with the implant, at the anterior end, tilted relative to its longitudinal axis (antero-posterior axis according to the convention used in the present application) so as to allow an oblique approach axis relative to the vertebrae.

It is generally preferred that a substantial portion of the anchor remain in the implant so as to properly retain the latter and that a substantial portion penetrate into the vertebra so as to be properly anchored in the vertebra (and thus retain the implant). The anchor is therefore generally dimensioned depending on the type and on the size of the implants used, which is itself generally dimensioned according to the vertebral level (e.g., cervical, thoracic or lumbar level, or even sacral level) in which it is intended to be implanted. Further, possible curvatures and orientations of the anchor and of the implants (notably their vertebral contact surfaces) are also generally provided according to the vertebral level, but also depending on pathologies or various parameters selected by the surgeon, notably as detailed above. Therefore it is understood that the selection of the length of the anchor (1) will be influenced by the value of its curvature and by the size of the implant. These considerations are generally known to one skilled in the art, but it may be useful to specify a few significant orders of magnitude for some of the embodiments of the present disclosure, even if the claims are not limited to the provided examples. Thus, mention may be made as illustrative and non-limiting examples of sizes of vertebrae and average intervertebral spaces which allow setting of the context of the normal (healthy) physiological values, even if it is clear that these values are indicative and that morphologies of certain patients lead to dimensions different from the ones mentioned. Further, pathologies or affections of the rachis will affect these values and the implants precisely aim at "adaptations" to these pathologies in order to be integrated into the patient and optionally restore physiological values as much as possible. In order to define the dimensions of a vertebra, reference is made below to the "width" for designating its dimension along a mediolateral axis (i.e., along the intersection axis of the coronal and transverse planes) and to the "depth" for designating its dimension along an antero-posterior axis (i.e., along the interception axis of the sagittal and transverse planes). At the cervical level, a width of about 10 to 25 mm, with a depth of 10 to 25 mm is again found for a vertebral height of about 10 to 25 mm and an intervertebral height of about 4 to 10 mm (the height here being along the axis of the rachis as already explained). At the thoracic level, a width of about 20 to 40 mm with a depth of about 15 to 35 mm is indeed found for a vertebral height of about 15 to 40 mm and an intervertebral height of about 6 to 12 mm. Finally, at the lumbar level, a width of about 30 to 60 mm with a depth of about 24 to 45 mm is generally found for a vertebral height of about 30 to 60 mm and an intervertebral height of about to 6 to 18 mm. These values allow an estimation of the dimensions of the implants used, which do not exceed these values in width and in depth, and the height of which may be variable (and even irregular for imposing an angle to the rachis, such as for example a lordosis, a kyphosis or for making up for a scoliosis). Corporectomy cages will have a height corresponding to the size of the vertebral segment to be replaced (at least one portion of at least vertebral body, generally with at least one portion of at least one adjacent disc). Intervertebral implants (cages or prostheses) on the other hand will have heights roughly corresponding to intervertebral heights of the spinal levels detailed above (to within the "adaptations", as detailed above). On the other hand, the dimensions in width and in depth are also selected according to the implantation route. Moreover the dimensions of the implants are defined below by using the term of "length" for designating the dimension along a substantially horizontal axis (relative to the rachis) and oriented between the face where the implant is held by surgical instrumentation during the implantation and the face of the implant which is inserted first. Thus the term of "width" designates the dimension in the same plane, but perpendicular to the length. From the following, it is understood that these widths and lengths will in fact be found in various orientations relative to the rachis (notably relative to the sagittal axis of the patient) and therefore reference to the antero-posterior and mediolateral axes of the patient (substantially perpendicular to the sagittal axis) are useful in order to designate the orientations of the widths and lengths of the implants. Indeed, at least in the case of intersomatic cages, the route for approaching the vertebra depends on the choice of the surgeon, generally forced by the surrounding tissues (veins and nerves mainly since they are the most risky). For an anterior approach route (an access), the implant (cage or prosthesis) will generally occupy almost the totality of the intervertebral width and depth. For a transforaminal approach, a cage is inserted, intended to occupy the diagonal of the vertebral plate (an oblique axis relative to the antero-posterior and mediolateral axes) and significant lengths are generally provided (for example of the order of about 30 to 35 mm) greater than the antero-posterior dimension (length) of the vertebrae, but a small width (for example about 10 mm) because of the nearby passing of nerve roots. For a lateral approach, the implant (generally a cage) will have a length occupying almost the totality of the mediolateral dimension of the vertebrae but will have a width smaller than the antero-posterior dimensions of the vertebrae (about 15 to 20 mm for example). Finally, for a posterior approach, a cage will generally be selected with a width as thin as with the transforaminal approach (about 10 mm for example), but with a lesser length since it will have to correspond to about the size of the vertebrae along the antero-posterior axis.

In this context of vertebral, intervertebral and implant sizes, it is understood that the anchor has to be dimensioned relative to the implants depending on the vertebral stages (levels) and optionally depending on the selected approach route. Nevertheless, mention may be made of illustrative and non-limiting examples such as that of an anchor for which the plate has a length of 15 to 20 mm and a width of about 4 mm. If an anchor is provided with at least one other plate, the latter may have dimensions of the same order, for example comprised between 2 and 5 mm. The thickness of the plate(s) of such an anchor will be of the order of 1 mm generally. It will be noted that one refers here to the plate thickness and not to the anchor thickness since in this case of several L, V, T plates, etc., one will of course have a total height of the anchor much greater than the thickness of the plates. Nevertheless, as mentioned earlier, the L or V profiles typically are preferred since they allow limitation of the congestion and of the required room in the implant (thus less weakened if it is a small implant) while promoting reliable attachment. Generally such an anchor will be used for an implant having a width of the order of 5 to 15 mm and a length of the order of 25 to 35 mm. Indeed, it is generally desired that there be about at least half of the length of the anchor jutting out from the implant and thus penetrating into the vertebra (for example about 10 to 15 mm, depending on the vertebral level and therefore on the height of the vertebra). Generally, an anchor is preferably used for which the width is less than half, or even less than one third or even ⅕th of the width of the implant, but for which the length is greater than one third, or about half of the length of the implant and possibly reaching up to a substantially identical length if the orientation and/or the curvature of the anchor and the vertebral height allow it.

On the other hand, it is understood from these dimensional considerations of the anchor (1) and of the implant (2), but also from considerations of physical properties and elastic limit as further detailed, that the bolt (3) should also be dimensioned relative to the anchor (and by extension to the implant). Indeed this disclosure provides some embodiments that promote good reliability of the maintaining of the anchor in the implant and therefore a reliable attachment of the implant relative to the vertebrae. Therefore a bolt is preferably used, for which the dimensions of the abutment (31), and generally of the abutment (14) of the additional anchor (1), represent at least 5 to 10% of the size of the plate of the anchor (1) at the level of which the abutment (31) will retain the anchor. The abutment (31) of the bolt preferably represents about 25% of the width of the plate with which it engages mutually. For example, in the case of a female means on the anchor, the male means of the bolt will be comprised between 5% and 50% of the width of the plate, preferably 25%. Thus, in the examples of L-shaped anchors (1) with a plate of 4 mm, and a plate of 2.4 mm, the notch forming the abutment (14) of the anchor (1) may extend over about 1 mm in the width of the 4 mm plate and the additional abutment (31) of the bolt may substantially have the same dimensions, but it is generally provided that the notch should be a little wider than the bolt (for example 1.1 mm). Generally, the 1 mm dimension (+/−10%, therefore comprised between 0.9 and 1.1) is typically advantageous (for example a diameter of 1 mm for the transverse section of a bolt in the form of a cylindrical rod), since it generally provides (depending on the material) sufficient strength for meeting safety requirements of the authorities as regards rachidian implants. Indeed, with such a size, the bolt may retain the anchor in its passage even if strong stresses are exerted thereon, even in parallel with the axis of the passage and of the anchor. Generally, this satisfactory retention is reinforced in the case when the "free" portion of the bolt (3) where the abutment (31) is found, only has one degree of freedom in the implant. In such cases, the abutment withstands extreme forces and it is generally the material (of the bolt, or of the anchor in general) which will undergo matting or shearing if the anchor has to be expelled by the exerted force. In addition, the preferred dimensional range may be widened between 0.7 mm and more than 1.2 mm, since it has been observed that for a size of 0.8 mm, the stiffness was not optimum (making the movements of the bolt too easy), but the elastic limit was slightly higher than for 1 mm where it was slightly low since the bolt had been subject to slight plastic deformation. However, even with the slight deformation (about 10% i.e. only 0.1 mm for a movement with an amplitude of 1 mm during the passing of the anchor), the elastic return during mutual engagement of the anchor and of the bolt was still accomplished sufficiently. Thus, 1 mm remains preferred but it is possible to select lower values in certain cases. One therefore understands from the foregoing, notably in combination with the explanations on the materials and the layouts of the housings of the abutment (31) of the bolt (3) in the implant, the range of parameters which may be used for the stiffness, elasticity and generally the mechanical strength of the bolt (3). Finally, mention is made here to the example of the cylindrical rod as a bolt (3) housed in the implants (such as for example in FIG. 18C or 19D) but it is understood that this rod may not be cylindrical and that dimensions of the order of those provided for making the bolt (3) meeting mechanical requirements, may be selected. For example, an abutment with a rectangular section with the length of the rectangle oriented parallel to the direction of insertion of the anchor and the width oriented perpendicularly gives the possibility of combining the proper stiffness of the 1 mm dimension for the length with the proper elastic limit of the 0.8 mm dimension for the width. One skilled in the art will therefore appreciate the possible variations and will have understood that various embodiments of this disclosure are clearly distinguished from the known systems by the layout, but also by the dimensioning of the elements cooperating with each other.

Also, the length of the bolt, notably the length of the flexible portion giving elasticity to the bolt, may be significant. It of course depends on the other dimensions (diameter, or width or length etc.,) for obtaining sufficient displacement of the abutment and suitable elastic return to the respective dimensions of the abutment of the anchor and of the abutment of the bolt. Also, the fixed portion in the implant (with or without specific retaining means as those described later on) should give the possibility of ensuring proper retention of the anchor. Finally, the size of the abutment portion (31) of the bolt relative to the abutment of the anchor (14) has already been described above as regards the dimension in the insertion axis of the anchor and the dimension in the displacement axis of the bolt, but it is also possible to note that the latter dimension will also correspond at least to the same dimension found at the anchor. For example, for an anchor with a 1 mm thick plate and a notch forming the abutment (14) of the anchor, the abutment of the bolt may measure at least as much as the thickness of the plate (i.e. 1 mm) but larger dimensions are generally preferred, or even considerably larger (for example twice the dimensions, i.e. 2 mm) for ensuring proper mutual engagement in spite of the flexure or torsion of the bolt (3). Thus, as a non-limiting example, in the case of a rod of the type of those illustrated in FIGS. 18D and 19D (and as visible in FIG. 18B for example), it will be possible to select a length of the order of 2.5 mm in the implant for the fixed retaining portion (32), of the order of 4.5 mm for the flexible portion (30) and of the order of 2 mm for the abutment (31). It is understood, by reasonably generalizing this example, that the flexible portion is dimensioned so that proper displacement is possible without any risk of elastic deformation. This dimensioning of the flexible portion (here, for example, of 4.5 mm for a total length of 9 mm) may therefore be generalized as being of the order of 30 to 70% of the largest dimension of the bolt, for example perpendicularly or tangentially to the axis in which the displacement should take place (in flexure or torsion).

Figure 3D:
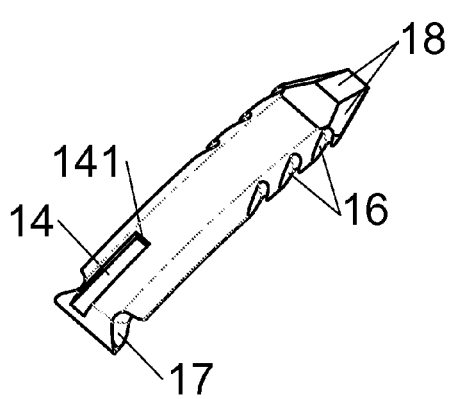
FIGS. 3D and 3E illustrate perspective views of an attachment device of the alternatives of FIG. 3A and FIG. 3C respectively and FIG. 3F illustrates a perspective view of a locking device according to the alternative embodiment of FIG. 3A.
Figure 3E:
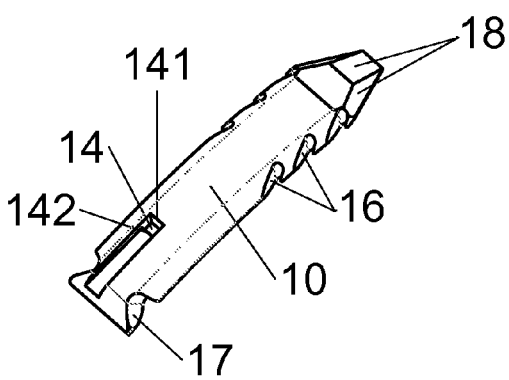

Ablation:

Various embodiments are laid out so as to allow ablation of the anchor (or even withdrawal of the implant). For example, various embodiments are provided so that the anchor (1) and/or the implant (2) and/or the locking means (3) include at least one means for accessing the locking means (3) in order to disengage the respective abutments (14, 31) of the anchoring device (1) and of the locking means (3). For example, FIGS. 2C, 3D and 3E represent anchors (1) for which the abutment (14) includes a groove on one face of the plate of the anchor. This groove extends as far as the posterior end, so that it is possible to introduce a tool for disengaging the abutment of the locking means. Thus, it is understood from these illustrative and non-limiting examples that it is possible to provide, in the actual anchoring device, a means for accessing the abutments for disengaging one from the other. The illustrative and non-limiting examples of FIGS. 1C, 4E, 4F, 5C, 6F, 7E and 7F represent anchors for which it is preferably the locking means (3) which allows unlocking of the anchor and having it leave the implant. Indeed, in certain embodiments, these access means are obtained by the fact that the locking means is accessible in the implant from the outside. The locking means is then directly accessible, for example because it is visible from the outside of the implant like for example in the embodiments of FIG. 1A, 4A, 4C, 4D, 5A, 5B, 6A, 6B, 6C or 17C. On the other hand, it is sometimes almost invisible from the outside such as for example in the embodiments of FIGS. 7A, 7B, 7C but it is possible to leave it accessible by providing the room for introducing a tool, for example a flat blade in the example of FIG. 7, for actuating the locking means so as to release the anchors, although this embodiment is rather intended not to facilitate ablation.

Figure 9A:
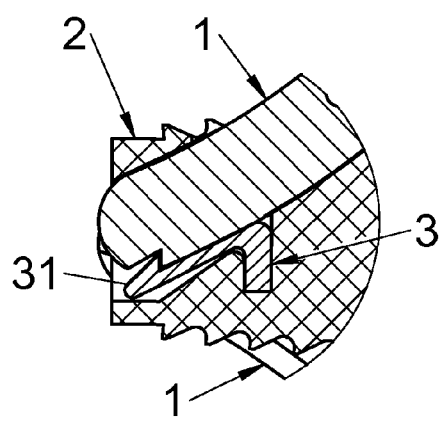
FIGS. 9A and 9B respectively illustrate a partial sectional view, along the sectional plane 9A-9A of FIG. 9B and a rear view of an implant provided with attachment devices according to an embodiment of this disclosure, FIGS. 9C and 9D respectively illustrate a perspective view and a profile view of an attachment device according to this embodiment and FIGS. 9E and 9F respectively illustrate a profile view and a perspective view of a locking device according to this embodiment.
Figure 9B:
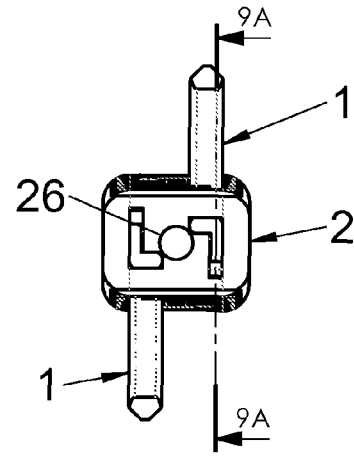
Figure 9C:
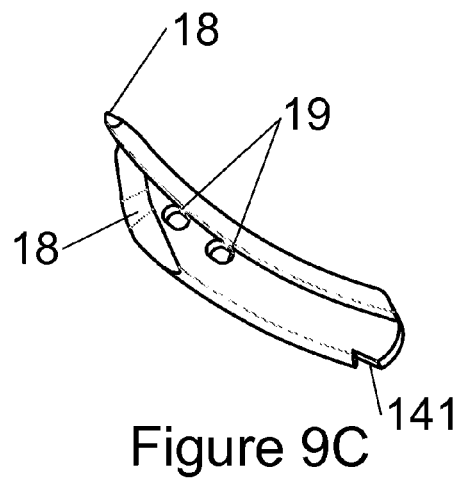
Figure 9D:
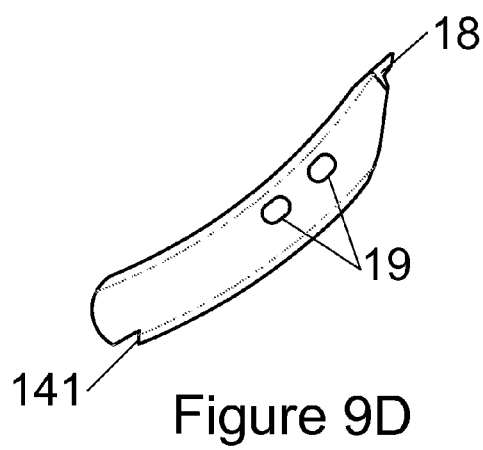
Figure 9E:
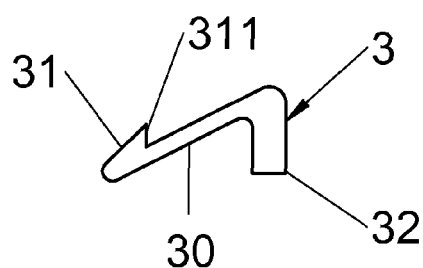
Figure 10A:
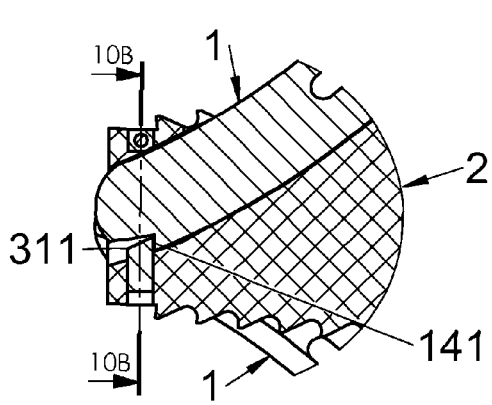
FIGS. 10A and 10C illustrate partial sectional views, along the sectional plane 10AC-10AC of FIG. 10B, of two alternatives of this embodiment of this disclosure.

In addition, it is possible to provide that the implant includes at least one access means, such as for example a recess or a channel opening onto the abutments of the anchor and of the locking means. For example, in FIG. 8B, the locking means is a split ring (of the "clamp clip" type) accessible via a conduit in the implant, via which it was introduced. In the example of FIG. 9A, the locking means, in the form of a hook, is housed in the implant and accessible from the outside even when the anchor is inserted into the implant. In the example of FIG. 10A, the locking means (3) is accessible from the outside of the implant by means of the shape of its abutment (31) and of that (14) of the anchor (1) which only includes a withdrawal abutment surface, while in the example of FIG. 10C, the double (withdrawal-advance) abutment (31) of the locking means is not directly accessible. Nevertheless, it is possible to provide an access channel in such embodiments, although this is not often preferred for reasons of solidity of the implant. Indeed, it is often preferable to avoid multiplication of the housings and channels in the implant for guaranteeing its solidity and various embodiments of this disclosure therefore benefit from other functional elements of the implant for providing this additional function for accessing the locking means (3). Thus, for example, in FIG. 8B, the housing of the split ring provides an access for placing the ring into the implant, but it also provides a hooking-up means (26) formed by a channel in the implant, allowing it to be grasped by an instrument such as an implant-holder (5) for example, as detailed later on.

Figure 21A:
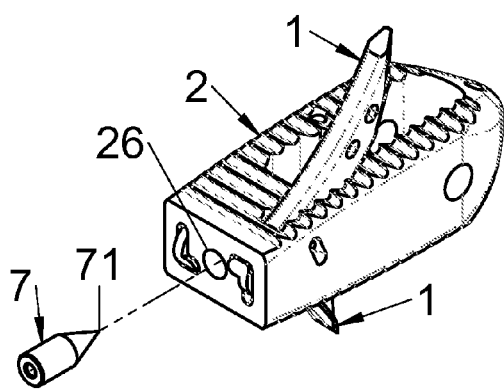
FIGS. 21A and 21B illustrate perspective views of an implant provided with attachment devices, before and during ablation of the attachment devices, respectively according to an embodiment of this disclosure, FIGS. 21C and 21D respectively illustrate a top view and a perspective view of this implant during ablation of the attachment devices
Figure 21B:
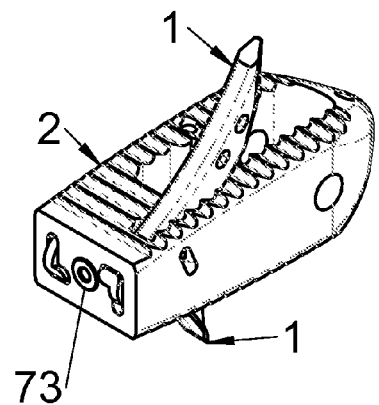
Figure 21C:
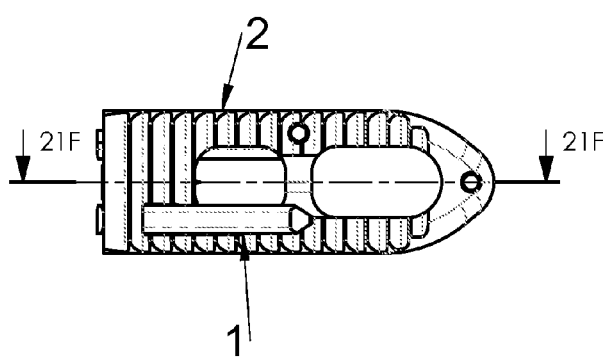
FIGS. 21E and 21F illustrate partial sectional views, along the sectional plane 21E-21E of FIG. 21D and the sectional plane 21F-21F of FIG. 21C, respectively.
Figure 21D:
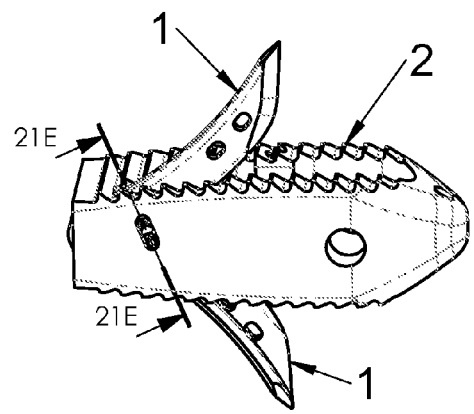
Figure 21E:
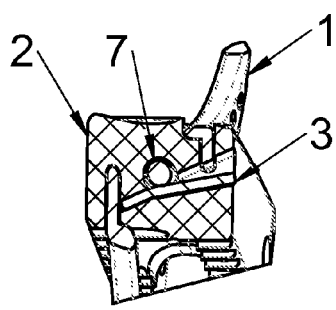
Figure 21F:
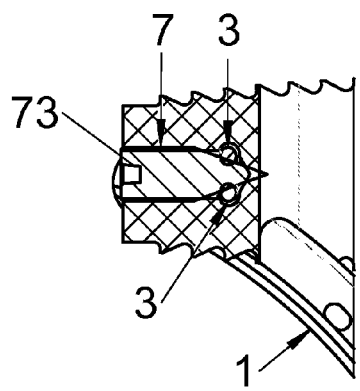

Also, in embodiments of the type of those of FIGS. 18 (A to I) and 19 (A to F), use may also made of this hooking-up means (26) formed by a channel, which allows insertion of the tool, such as for example illustrated in FIGS. 20 (A to F) and 21 (A to F). These figures illustrate various types of tool for ablation, such as for example a tool (6), one end of which (61) comprises a self-perforating screw thread (62) for FIGS. 20A and 20B or like a kind of self-perforating screw (7) (capable of boring the implant by its screwing) for FIGS. 20C and 20D, or else like a kind of screw (7) with a threading (72) mating a tapping thread in the hooking-up means (26), or further like a kind of spiked pin (7) without any threading such as for example in FIGS. 21A and 21B. In the case of a self-perforating screw thread (62, 72) like in FIGS. 20A and 20C for example, it may be arranged to screw in the tool (6) or the screw (7) which the implant has or not, into the posterior end of the implant with a hooking-up means (26) such as a hole. In the case of the threading mating a tapping thread of the hole (26) like in FIG. 20E for example, no boring is required and the screw (7) does not widen the hole. In these screw examples, of course a screw head is provided which may be manipulated by a tool (e.g., screwdriver with a flat-blade, or Phillips head, or other configuration, or a wrench for hexagon or other shaped socket bolts, for example). In the case of the pin of FIGS. 21A and 21B, no head allowing actuation rotation of the pin (7) is required, but it is still possible to provide a hole (73) for example tapped or with a flat section or a notch, in the posterior face of the pin (7) for facilitating its withdrawal from the implant. FIGS. 21E and 21F show in an illustrative and non-limiting way how the unlocking may occur in this type of embodiments, by means of the tip of the tool, the screw or the pin which opens on the locking means and pushes it back (in a space in the implant) for disengaging it from the abutment (14) of the anchor (1), by its flexibility. It will be noted that this type of mechanism may also be used for the implantation and not only for the ablation. Indeed, an implant held by its implant-holder may have its locking means pushed back during the insertion of the anchoring device and, when the implant is released, the additional abutments (14, 31) of the anchor (1) and of the locking means (3) may engage with each other.

Figure 22A:
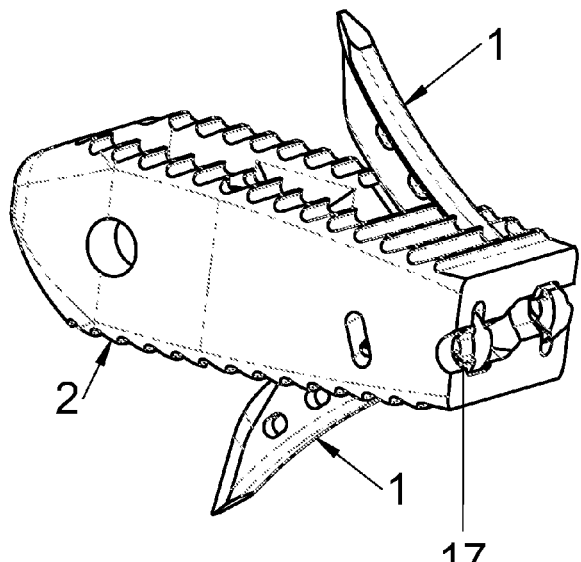
FIG. 22A illustrates a perspective view of an implant provided with attachment devices, before ablation of the attachment devices according to an embodiment.
Figure 22B:
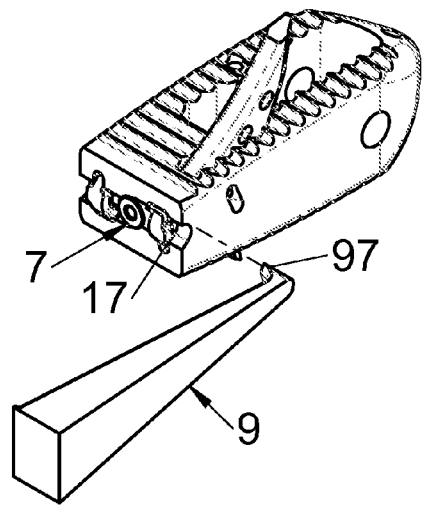
Figure 22C:
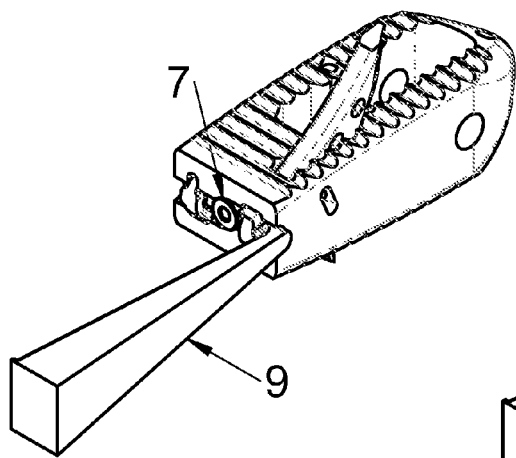
Figure 22D:
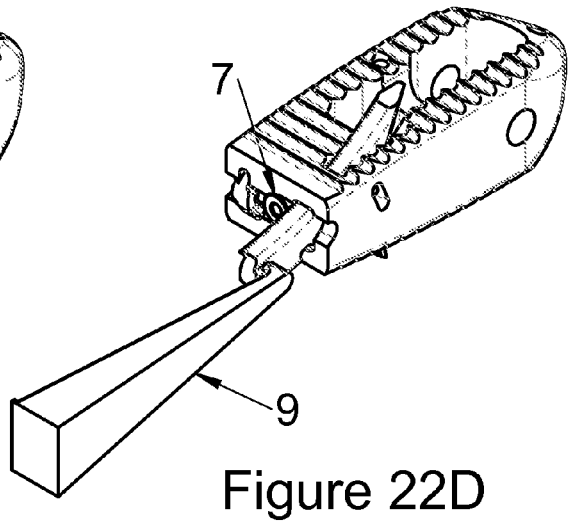
Figure 23A:
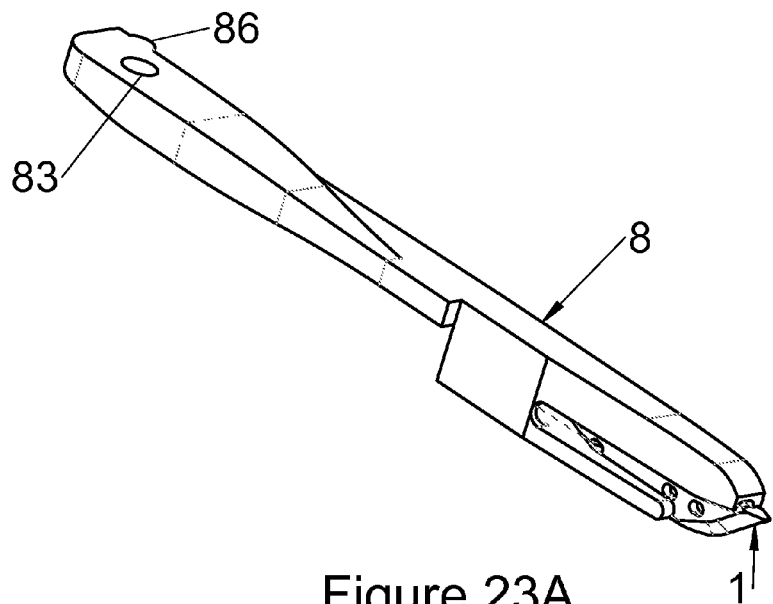
FIGS. 23A, 23B and 23C respectively illustrate a perspective view, a top view, and a sectional view along the sectional plane 23C-23C of FIG. 23B, of a loader bearing an attachment device according to certain embodiments
Figure 23B:
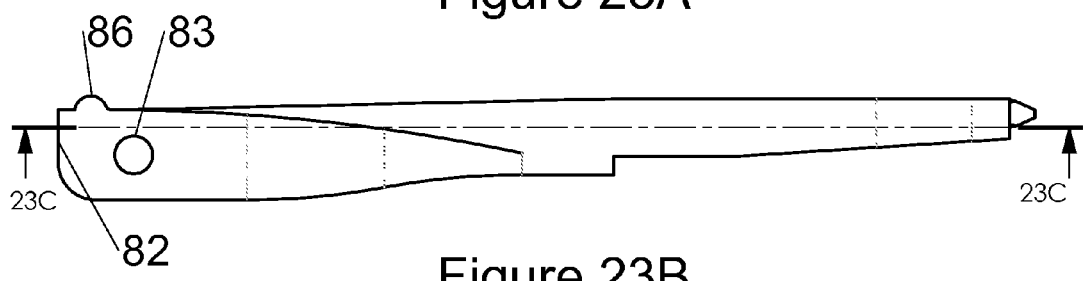
Figure 23C:
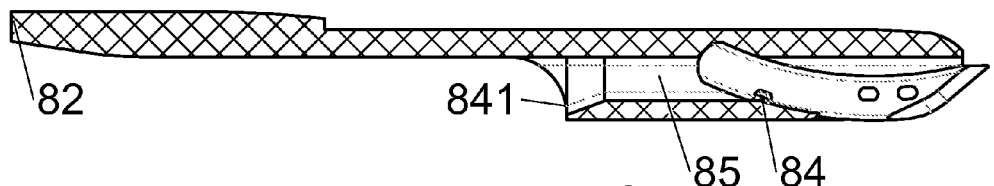
Figure 23D:
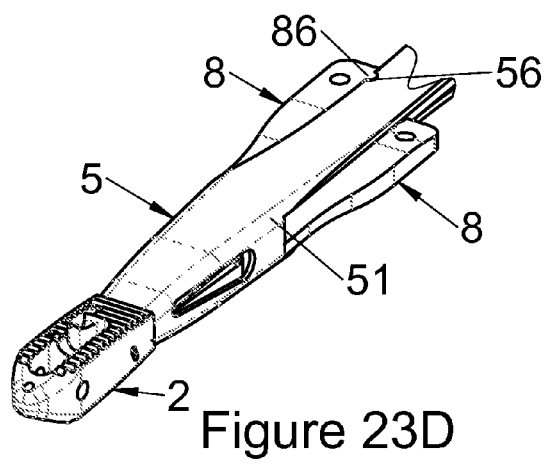
FIG. 23D illustrates a perspective view of a portion of an implant-holder containing two loaders.

In addition, in order to facilitate ablation, various embodiments provide that the anchor (1) includes at least one hooking-up means (17), configured for hooking-up the end of a tool allowing withdrawal of the anchoring device (1). Preferably said hooking-up means (17) is located near the posterior end of the device (1). In a complementary way, the implant includes in various embodiments, at least one means for accessing from the outside of the implant at least one hooking-up means (17) of the anchoring device (1), configured for hooking up the end of a tool allowing withdrawal of the anchoring device. Thus, as for examples illustrated in FIGS. 22A, 22B, 22C and 22D, the anchors may include a housing or a lug or any irregularity with a suitable shape in order to form a hooking-up means for the end of a tool (9). Such a tool (9) may for example be of the type of the one illustrated in FIGS. 22B, 22C and 22D, for example including a handle for it to be grasped manually and an end (97) with a shape mating the hooking-up means (17) of the anchor (1). For example, as illustrated in FIG. 22B, the end (97) forms a sort of hook engaging into a housing or picking up a lateral protrusion on the posterior end of the anchor, so as to be able to pull thereon. Of course, these examples of structures are not limiting and what is important here is actually the functional definition of a hooking-up with the tool, whether the functional means are male or female on either one of the tool and of the anchor, or whether they are simply formed with shoulders mating the anchor and the tool which are put into contact for pulling on the anchor. It will be noted that in the illustrative and non-limiting examples of FIGS. 22A, 22B, 22C and 22D, this withdrawal is achieved by having unlocked the anchor by means of a pin, but this type of withdrawal with a tool applies to any type of unlocking, notably those described above.

On the other hand, in certain embodiments of the present disclosure exhibiting enhanced reliability, possible ablation may be provided without resorting to direct actuation on the locking means (3). Indeed, in certain embodiments, at least one of the surfaces, from among the abutment surface (141) of the abutment (14) of the device (1) and the abutment surface (331) of the abutment (31) of the bolt (3), is oriented non-perpendicularly to the insertion axis of the anchoring device (1) in the implant (2), in order to give the possibility of pushing back the abutment (31) of the locking means (3) and thus unlocking the anchoring device (1) by traction produced on the anchor (1), for example via a hooking-up means (17), for example by means of a tool (9). Thus, with a slightly tilted abutment surface (for example, surface 141 and/or 311 depending on the case), fraction gives the possibility to the abutment surfaces (141, 311) of sliding on each other by pushing the bolt back into its housing in order to let the anchor (1) move out. Thus, for example, in the case of the notches, provision may be made for a V-notch, or even with a single inner wall tilted towards the outlet of the passage, the other wall being perpendicular to the axis of the passage or also tilted towards the outlet instead of being tilted towards the inlet of the passage like for a V-notch. This type of shape will even further facilitate ablation if means for accessing the bolt (3) have not been provided (or not been possible to provide). It will also be noted that in the case when the second wall is also tilted towards the outlet of the passage, an advantageous embodiment is obtained wherein the bolt may itself be slightly locked in the passage of the anchor in the implant, by means of this tilted wall.

Locking and Retaining Means:

The locking means, as explained above may be made in various materials, either identical or different from the implant, and it may have various shapes that still mitigate the anchor (1) from leaving the implant (2) and/or limit the advance of the anchor (1) in the implant (2) and the bone. The number of anchors (1) and of abutments of the locking means in the alternatives described in the present application should not be construed in a limiting way, but some useful embodiments have only one single locking means (3) for locking two anchors (2). Also, the positions of the locking means relative to the anchors are described with reference to the examples provided in the figures illustrating generally advantageous embodiments for the obtained gain of room, but it is clear that various elements cooperating with each other may be positioned differently from the position shown in these examples, for example because the implants provide sufficient room for varying the positions and orientations of the various elements. Also, the present application provides many embodiments for the shape of the locking means (3) and the provided illustrative examples, notably in the figures, are not limiting (which applies to the whole of the elements and features described in the present application). Finally, the present description frequently mentions that the locking means (3) is "formed with" but it should be clear that this term is not limiting since this is in fact at least one locking which is obtained with the described structures, while it is quite possible to provide combinations of the described functional and/or structural features, from an anchor to another or sometimes for a same locking means.

Figure 1D:
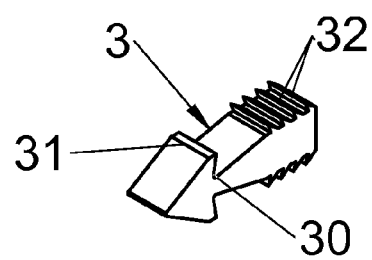
Figure 3F:
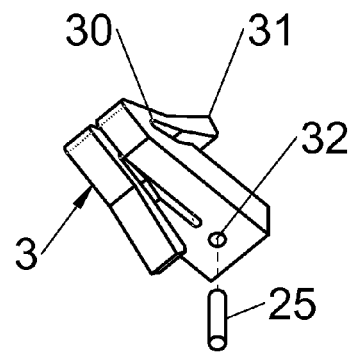
Figure 9F:
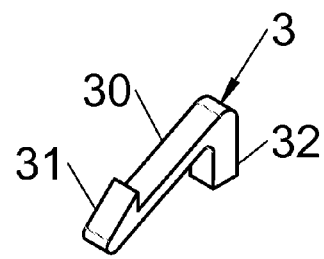
Figure 10B:
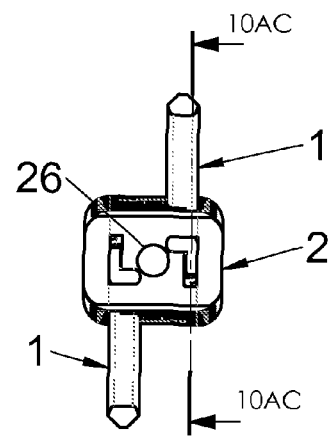
FIG. 10B illustrates a rear view of an implant provided with attachment devices according to an embodiment of this disclosure.
Figure 10C:
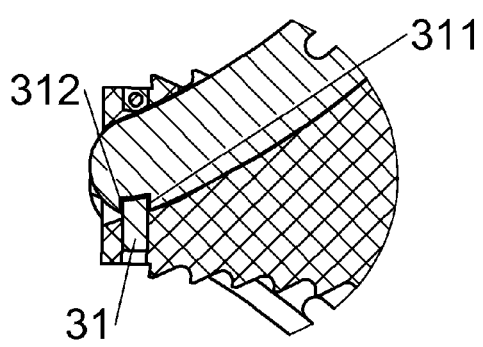
Figure 10D:
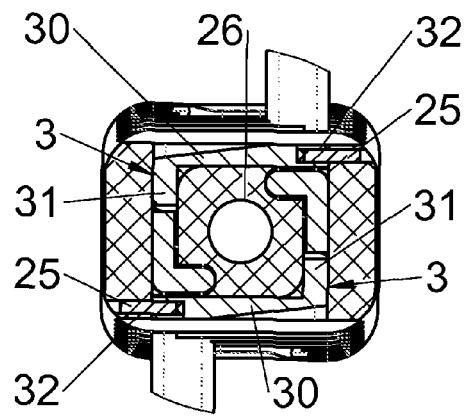
FIG. 10D illustrates a partial sectional view, along the sectional plane 10D-10D of FIG. 10A, of the alternative embodiment of FIG. 10A, FIGS. 10E and 10F respectively illustrate a profile view and a perspective view of an attachment device, of the alternative of FIG. 10A.
Figure 10E:
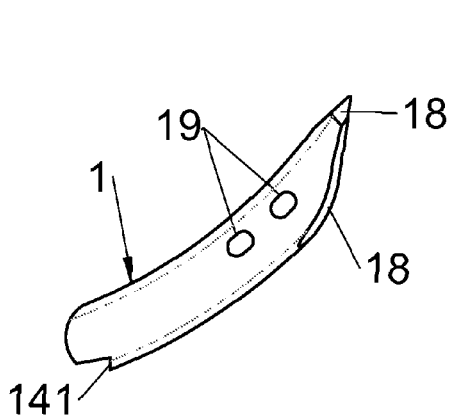
FIG. 10G illustrates a perspective view of a locking device according to the alternative embodiment of FIG. 10A.
Figure 10F:
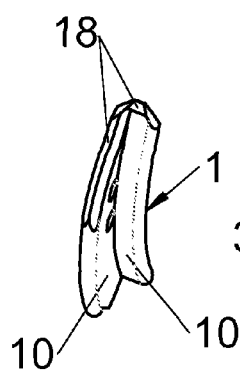
Figure 10G:
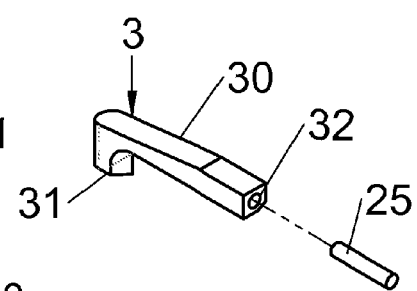
Figure 11G:
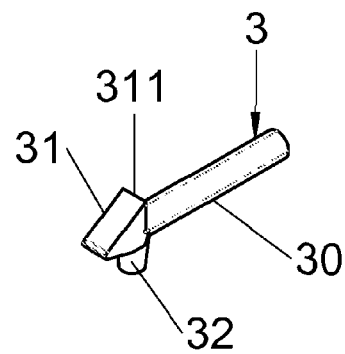

In certain embodiments, the locking means (3) substantially has the shape of a harpoon as illustrated in FIGS. 1D, 2D and 3F for example. In certain embodiments, such as for example in FIG. 1D, the locking means (3) has for example a parallelepipedal body (or cylindrical or of any other shape in other possible alternatives), extending with a thinned portion forming the flexible portion (30) at the end of which a head, for example with a triangular section, provides at least one protruding edge forming the abutment (31). In certain alternatives, such as for example in FIG. 2D, the body extends with a head provided with at least one flexible tab (30), the end of which forms the abutment (31). In certain alternatives, such as for example in FIG. 3F, the body separates into two branches each bearing a flexible tab (30) which each forms an abutment for an anchoring device. In these embodiments the head or the branches are preferably refined, for example with a triangular section, so as to facilitate the passing of the anchors (1) by pushing the head or the tabs by means of the flexibility of a portion (30) of the locking means (3). In certain embodiments, such as for example in FIG. 4G, the locking means (3) includes a body intended to be housed in the implant and extended with two branches extending towards the inlet of both passages each intended to receive an anchor (1). These branches end with abutments (31), for example in the form of small protruding blocks at the end of the branches in FIGS. 4A and 4G, or near the end of the branches in FIG. 4C. In the alternative of FIG. 4C, the abutments (31) of the locking means (3) are formed with housings receiving small blocks present on an edge of the anchors (therefore opposing both withdrawal and advance). Although other configurations may be useful, from the foregoing it is understood that it is possible to provide various layouts of the locking means (3) having a flexible portion (30) laid out for allowing flexure expressed by a substantially vertical movement of the abutment, thus pushed back (upwards or downwards) for letting through the anchors (1), and then returning to an initial position for locking the latter. In the example of FIG. 9F, the locking means (3) is formed with a rod oriented along the antero-posterior axis of the implant, but one end of which is curved in order to engage into a housing of the implant (2) along an axis not parallel to the antero-posterior axis, in order to thereby retain the locking means (3) while allowing flexure of the rod along a substantially vertical movement during the passing of the anchor (1). The other end of the rod includes the abutment (31) for example formed with a catch intended to cooperate with a mating notch of the anchor (1). In the example of FIG. 10B, the locking means (3) is formed with a rod oriented not parallel to the antero-posterior axis, and one end of which includes the flexible portion (for example by thinning of the rod) at the end of which is positioned a tab opening into the passage of an anchor, via a dimensioned conduit so that the flexible portion may flex and let through the anchor and then engage into a notch (FIG. 10C) or against a catch (FIG. 10A), for example on a lateral edge of the anchor. In the examples of FIGS. 11F and 11G, the locking means (3) is formed with a rod housed in a conduit of the implant and oriented along the antero-posterior axis of the implant, but an end of which includes a block (32) jutting out in a housing of the implant (2) along an axis not parallel to the antero-posterior axis, in order to thereby retain the locking means (3) while allowing flexure of the rod along a substantially vertical movement during the passing of the anchor (1). In this example, this same end of the rod includes the abutment (31), for example formed with a housing (FIG. 11F) or a catch (FIG. 11G) intended to cooperate with a complementary abutment (14) of the anchor (1), for example as illustrated in FIGS. 11A and 11C.

Figure 5D:
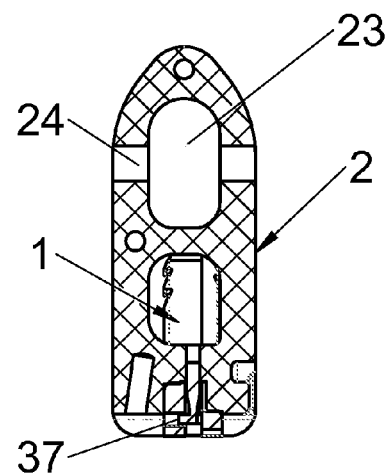
Figure 5E:
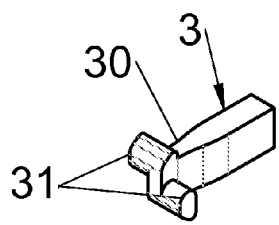

In certain embodiments, the flexible portion (30) is laid out so as to allow a substantially horizontal movement of the abutments which are therefore pushed sideways. For example, in FIGS. 5E and 6G, the locking means (3) includes a body which gets thinner (sideways/in the horizontal plane) near a head bearing on its natural edges, two abutments (31) each having a shape allowing the passing of an anchor and then its locking during elastic return. In the example of FIG. 5E, the abutment (31) of the locking means (3) are male means which penetrate into the female means (14) made in the anchors (1), while in the example of FIG. 6G, the abutments (31) of the locking means (3) are formed with shoulders made on the edges of the head and fitting the shape of the posterior end (14) of the anchors (1). In this example of FIG. 6G, the abutment surface (311) opposing the withdrawal has a concave shape in order to fit the convex shape of the rear of the anchor. Moreover it will be noted that it is generally preferred to have a shape of the rear of the anchors, as well as for the edges of the implants, giving the possibility of avoiding having protruding or cutting structures which may damage the surrounding tissues. In the example of FIGS. 6B, 6C and 6D, the locking means includes the same curved type of abutment surface (311) for the withdrawal, but it also includes an abutment surface (312) for limiting penetration of the anchor (1) into the implant (2). This advance abutment (312) is preferably formed with a more salient angle since it has to stop the anchor and it does not risk damaging surrounding tissues considering that it is intended to be in contact with the abutment (14) of the anchor (and even covered by the abutment in this particular example). Further, it will be noted that in this example, the end of the catches forming the abutment (31) has, between the abutment surfaces (311, 312), a beveled surface according to an angle preferably corresponding to the angle of insertion of the anchor, so that the latter may slide more easily along this beveled surface. Further, the end of the head of the locking means between both advance abutment surfaces (312) is laid out so that the advance abutment surfaces (142) of the anchors may freely pass up to the contact with two advance abutment surfaces (312) of the locking means (3). This head will therefore preferably have a spiked profile with surfaces substantially parallel to the insertion axis of the anchors (1), as illustrated in FIG. 6D for example.

Figure 13D:
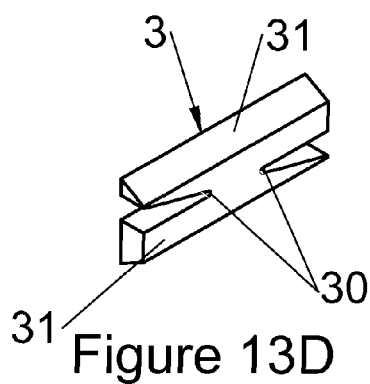
Figure 13E:
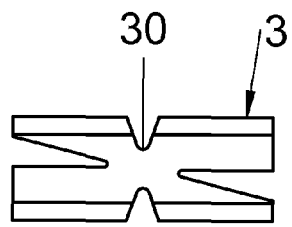
Figure 15A:
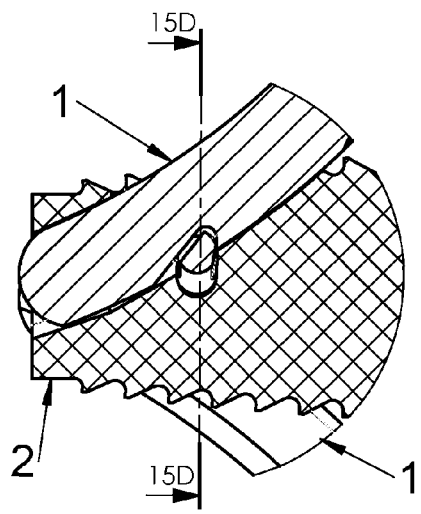
FIGS. 15A, 15C and 15D illustrate partial sectional views, along the sectional plane 15A-15A of FIG. 15B, along the sectional plane 15C-15C of FIG. 15B and along the sectional plane 15D-15D of FIG. 15A respectively of this embodiment of this disclosure.
Figure 15B:
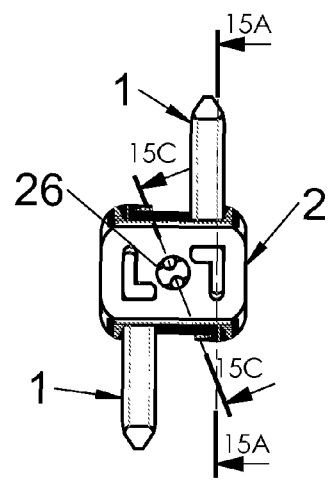
FIG. 15B illustrates a rear view of an implant provided with attachment devices according to an embodiment of this disclosure.
Figure 15C:
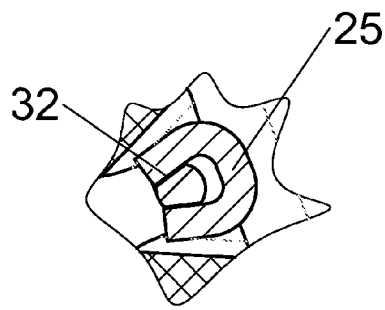
Figure 15D:
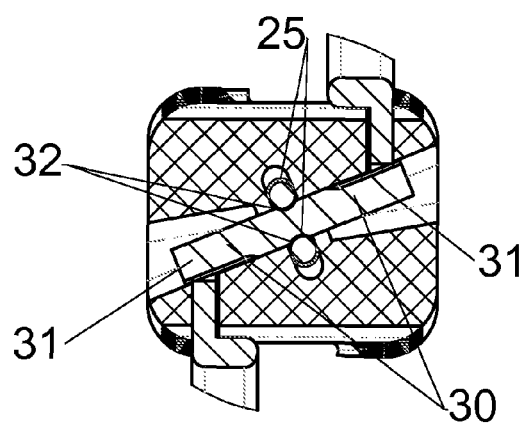
Figure 15E:
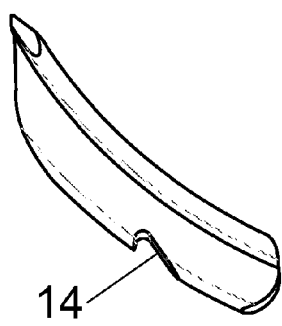
FIGS. 15E and 15F illustrate perspective views, of an attachment device and of a locking device respectively according to this embodiment.
Figure 15F:
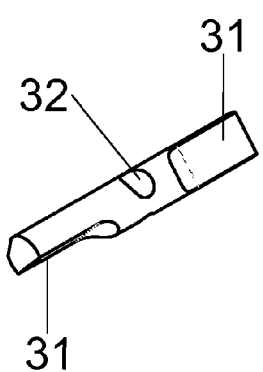
Figure 17G:
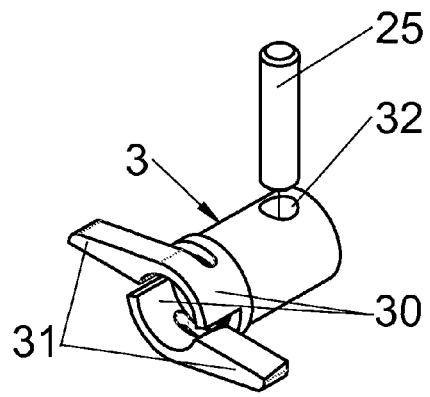
Figure 19A:
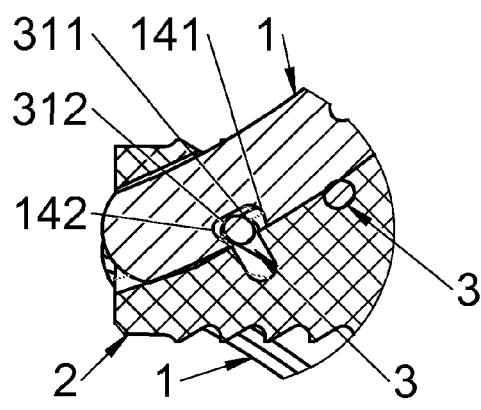
FIGS. 19A and 19D illustrate partial sectional views, along the sectional plane 19A-19A of FIG. 19B and along the sectional plane 19D-19D of FIG. 19C respectively of this embodiment of this disclosure, FIGS. 19E and 19F respectively illustrate a profile view of an attachment device and a perspective view of a locking device according to this embodiment.
Figure 19B:
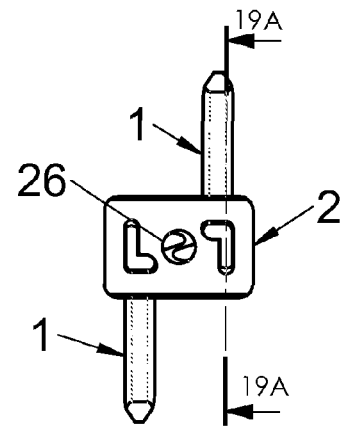
FIGS. 19B and 19C respectively illustrate a rear view and a top view of an implant provided with attachment devices according to an embodiment of this disclosure.
Figure 19C:
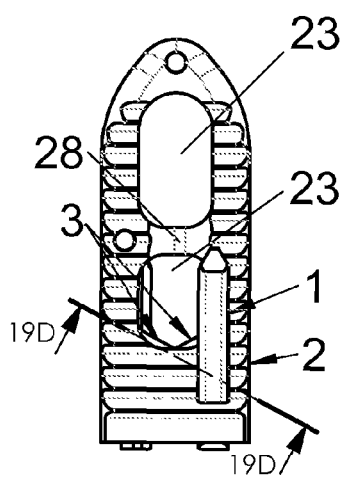
Figure 19D:
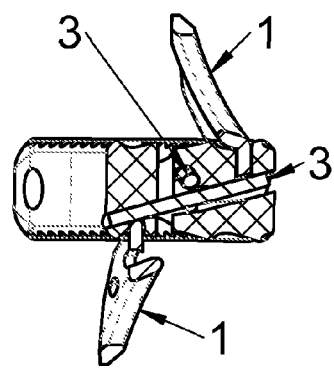
Figure 19E:
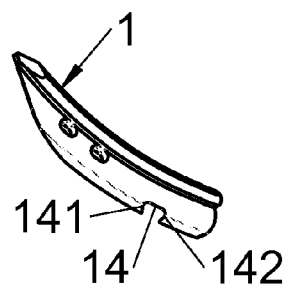
Figure 19F:
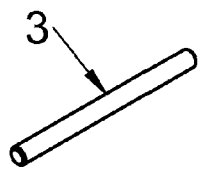
Figure 20A:
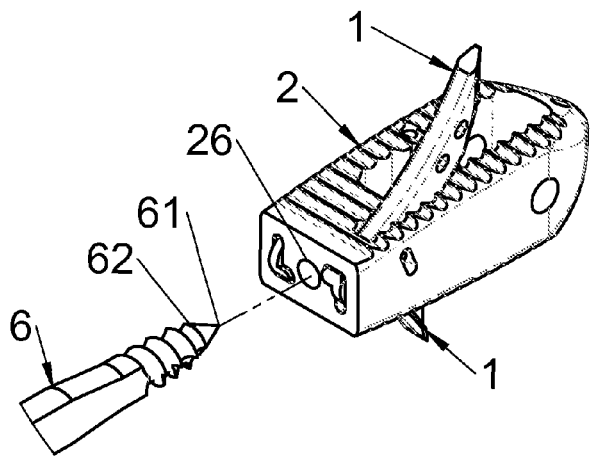
FIGS. 20A, 20C and 20E illustrate perspective views of an implant provided with attachment devices, before ablation of the attachment devices according to three embodiments.
Figure 20B:
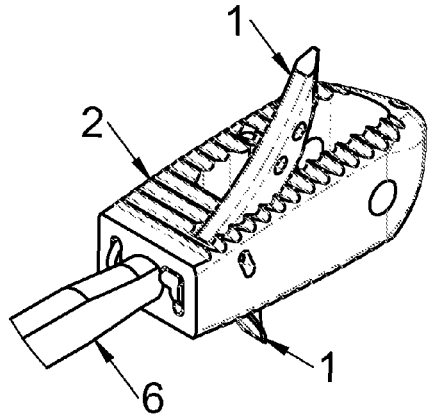
FIGS. 20B, 20D and 20F illustrate the implants, of FIGS. 20A, 20C and 20E, respectively, during ablation of the attachment devices.
Figure 20C:
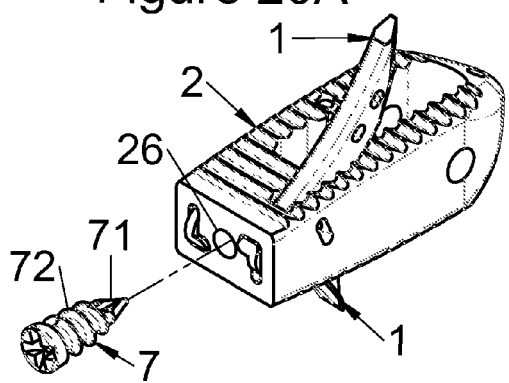
Figure 20D:
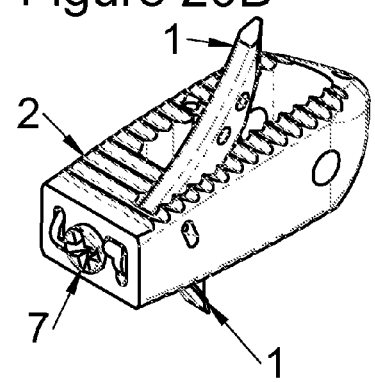
Figure 20E:
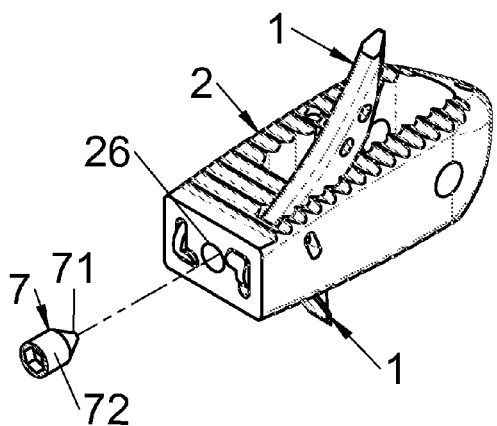
Figure 20F:
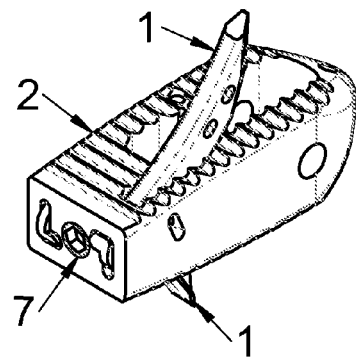

In certain embodiments, the flexible portion (30) is laid out so as to allow a rotational or torsional movement. For example, in the example of FIG. 7G, the locking means (3) includes a body extended with a finer and flexible neck (30), at the end of which is made a wider head than the body and obliquely oriented so that its torsion allows the passing of the anchors and then locks the latter by the elastic return of the flexible portion (30). The abutments (14) of the anchors may then be grooves near the lateral edge of one of the surfaces of the plate (in this case, the convex face in the illustrated example). In the example of FIG. 13D, the locking means (3) includes a parallelepipedal body with a substantially rectangular section for example, in which cutouts are made, preferably in the shortest edges of the rectangle and being closer to each other near the center of the locking means (3) thereby providing flexibility of the central portion (30) and thereby defining four branches including two which are intended to be subject to torsion, in order to let through an anchor and so that their edge engages into a notch of the anchor for locking the latter. In the example of FIG. 13E, the parallelepipedal body is equipped with four cutouts in order to improve the flexibility of the central portion (30). In the example of FIG. 17G, the locking means (3) is formed with an insert, preferably with a substantially cylindrical shape, preferably screwed in or introduced by sliding into a housing of the spinal implant (2). In this example, the abutment (31) is formed with at least one tab, for example flexible or made to be moveable by a cutout of a portion of the cylindrical circumference at its base. This tab opening into the passage is thus laid out so as to undergo torsion and engage by elastic return into the abutment (14) of the anchoring device (1) (then formed by a notch or catch in an edge of the anchor). In certain alternative embodiments, this cylindrical insert may be hollow and tapped so that it forms a means (16) for hooking up the implant with an instrument (an implant-holder (5) for example).

Figure 8A:
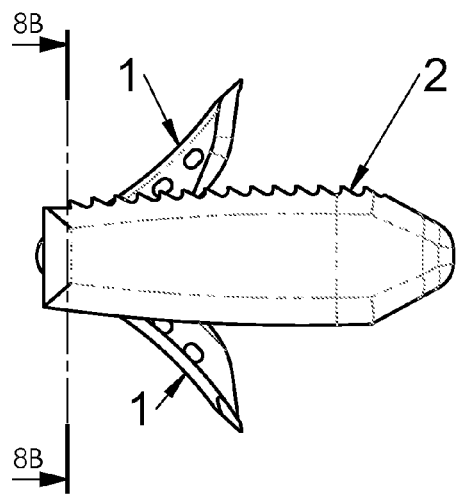
FIGS. 8A and 8B respectively illustrate a profile view and a partial sectional view, along the sectional plane 8B-8B of FIG. 8A, of an implant provided with attachment devices according to an embodiment of this disclosure.
Figure 8B:
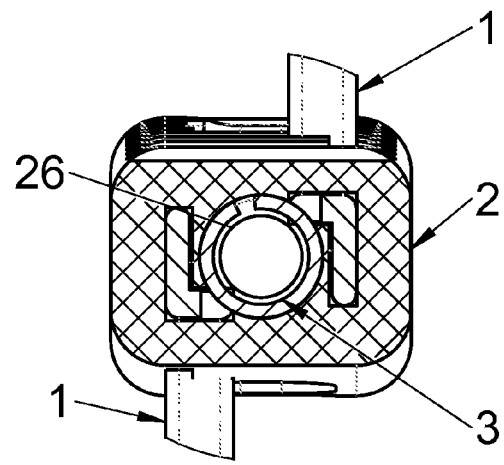
Figure 8C:
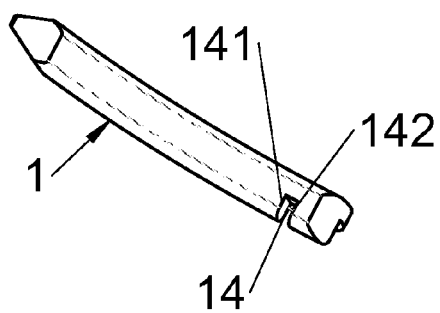
FIG. 8C illustrates a perspective view of an attachment device according to this embodiment and FIG. 8D illustrates a perspective view of a locking device according to this embodiment.
Figure 8D:
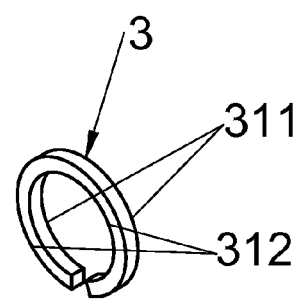

In certain embodiments, the flexible portion (30) is laid out so as to allow a compression movement. For example, as illustrated in FIG. 8D, the locking means (3) may be formed with a split ring shape inserted into a complementary housing of the spinal implant (2) near passages receiving the anchors. The edges of the ring slightly jut out in the passages and therefore form abutments (31) of the locking means (3). In a complementary way, the anchors have notches (14) on one of their lateral edges for receiving the edges of the ring. This simple embodiment has the advantage of locking in the withdrawal and advance direction, and allows locking of both anchors (1) with a single ring (3).

Figure 12C:
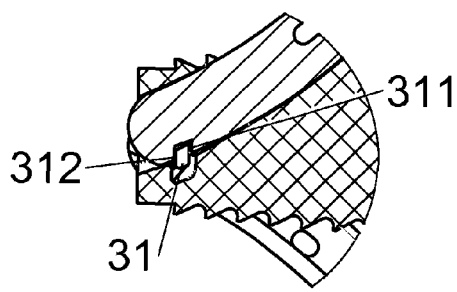
Figure 12D:
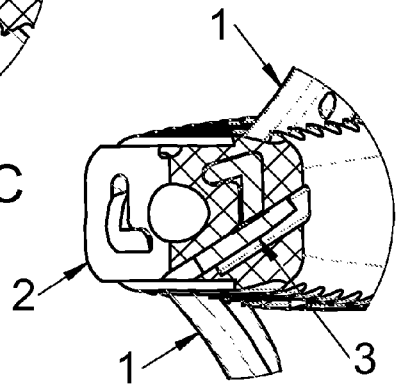
FIG. 12D illustrates a partial sectional view, along the sectional plane 12D-12D of FIG. 12E, of this embodiment, FIGS. 12F and 12G respectively illustrate a profile view of an attachment device and a perspective view of a locking device according to this embodiment.
Figure 12E:
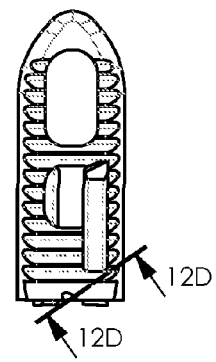
Figure 12F:
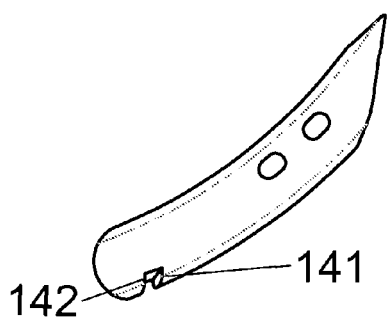
Figure 12G:
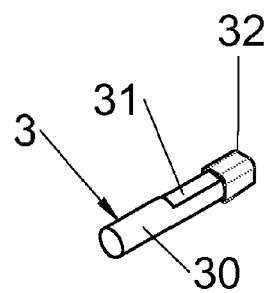

In certain useful embodiments, the locking means (3) is formed with an insert of elongated shape along a longitudinal axis not parallel to the insertion axis, like for example a rod or a stick. These embodiments generally have additionally the advantages of great simplicity and low cost for applying them, while providing an efficient solution for locking. In the example of FIG. 12G, the locking means (3) is formed with a rod oriented not parallel to the antero-posterior axis, and housed in a conduit of the implant so that a portion of the rod juts out inside the passage of the implant (2) intended to receive the anchor. As visible in FIGS. 12E and 12D, the orientation of the rod may be oblique relative to the antero-posterior axis of the implant, but also preferably oblique relative to the vertical and horizontal axes, so that the conduit and the rod do not weaken too much the implant and do not coincide with another element of the implant, such as for example a means (26) for hooking up the implant with an instrument (5). A rectilinear rod is therefore a very simple and inexpensive element as well as its layout in the implant which then includes a conduit mating the dimensions and shapes (for example cylindrical) of the rod at one of the ends of the latter. This conduit is on the other hand widened at the other end of the rod, so as to allow flexure of its flexible portion (30). Of note for this example, but being aware that this applies to many embodiments, the flexible portion (30) is defined by its flexural function but that it is not necessarily different from the other portions of the locking means (3), except sometimes for its dimensions, voluntarily thinned for facilitating flexure. Indeed, in the embodiments where the locking means (3) is formed with a rod, the flexible portion is in fact generally a portion from which flexure of the locking means (3) is allowed by the dimensions of the conduit in the implant while it may completely be identical with the other portions of the locking means (3). The rod of FIG. 12G introduced into its channel or conduit of the implant may flex in order to let through an anchor and may, by elastic return, be engaged with this anchor, for example on a catch of the anchor (FIG. 12A) or in a notch of the anchor (FIG. 12C). In certain alternative embodiments, the rod (3) includes at least one flat optimizing the contact between the locking means (3) and the anchor (regardless of whether the latter includes an abutment in the form of a catch or a notch).

In certain useful embodiments, the locking means (3) includes at least one bevel facilitating the passing of the anchor (1), so that the anchor (1) may slide along the locking means (3) while avoiding being damaged and/or damaging the locking means (3). Indeed, as it is provided that at least one portion of the locking means (3) may be pushed back into a housing of the implant to let through the anchor, it is sometimes useful that the surface on which the locking means may be pushed back, not be too prominent or sharp. In some embodiments at least one bevel or a convex portion on this surface is provided for facilitating the passing and avoiding damaging the anchor (1) and/or the locking means (3) since tiny debris may be produced and forgotten in the body of the patient. Thus, the harpoon shape described above for FIGS. 1D and 2D is not limiting but expresses the presence of such bevels. Also, in FIG. 4G, it is seen that the abutments bear, on the face which does not form an abutment, a bevel for facilitating the passing of the anchor (unlike FIG. 4C where both faces form an abutment). Also, in FIG. 6G, the lateral edges of the abutment are beveled for facilitating the passing of the anchors while pushing back the abutment (31) sideways. Thus, beveled or curved surfaces are useful and the embodiments wherein the abutments (31) of the locking means are convex, may be preferred, such as for example in FIGS. 18 and 19.

Figure 16A:
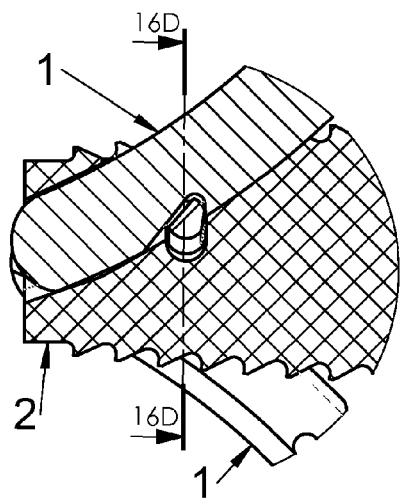
FIGS. 16A, 16C and 16D illustrate partial sectional views, along the sectional plane 16A-16A of FIG. 16B, along the sectional plane 16C-16C of FIG. 16B and along the sectional view 16D-16D of FIG. 16A, respectively, of this embodiment of this disclosure.
Figure 16B:
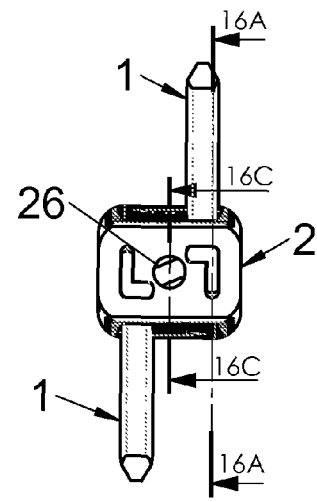
FIG. 16B illustrates a rear view of an implant provided with attachment devices according to an embodiment of this disclosure.
Figure 16C:
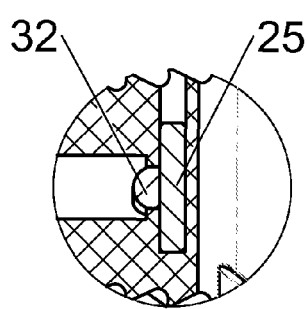
Figure 16D:
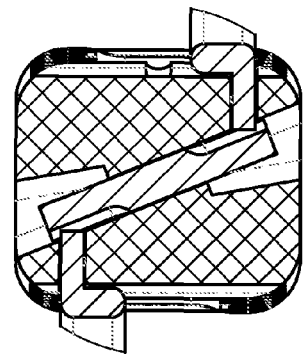
Figure 16E:
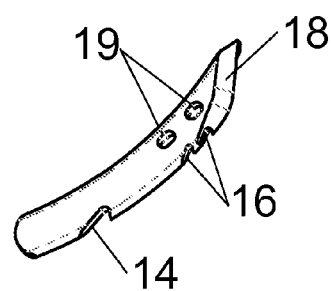
FIGS. 16E and 16F illustrate profile views, of an attachment device and of a locking device respectively according to this embodiment.
Figure 16F:
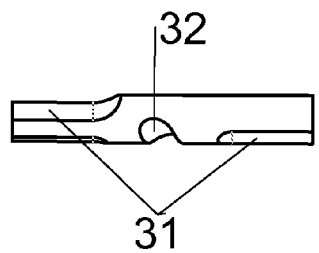

In certain embodiments, the locking means (3) and the implant (2) are laid out in order to avoid as much as possible any weakening of the implant by the presence of the locking means (3) and its conduit in the implant (2). Indeed, in certain embodiments described above, the locking means (3) is inserted into the implant near the posterior end of the implant and the amount of material which retains the locking means (3) is therefore limited (FIG. 12A for example shows a reasonable amount of material but which may be varied, such as for example in FIG. 14A, 15A, 16A or 18A). In order to mitigate breakage or instability, certain useful embodiments therefore provide positioning and/or orientation of the locking means which aim at preserving the integrity of the implant (2). Further in the example of FIG. 12B for example, the layout of the locking means (3) requires a means (3) for locking with an anchor (1) because of the position and of the orientation of the locking means (3). Certain embodiments therefore aim at improving this position and this orientation so that a single locking means (3) may lock two anchors in the same time. Thus, various embodiments of the present disclosure address these problems by providing a not very cumbersome solutions which are reliable and mitigate weakening of the implant, optionally by limiting the number of locking means (3) required for locking several anchors (1). In the example of FIGS. 14E and 14G, the locking means (3) is formed with an insert, for example with a substantially cylindrical shape, such as a rod for example, housed in a conduit of the implant which is for example oriented in a plane perpendicular to the antero-posterior axis of the implant, but oriented so that a same locking means (3) may lock two anchors simultaneously, which generally involves an oblique orientation relative to the horizontal plane, for example as visible in the example of FIG. 14E. FIG. 14A clearly shows that this type of locking means (3) is positioned in a conduit located at a distance from the posterior end by which it is possible to avoid weakening the implant. Thus, the rod forming the locking means (3) may be positioned obliquely in a conduit of the implant, the middle portion of which mates the rod but which flares in its lateral portions so that the rod may flex and allow the passing of the anchors. The alternative embodiments shown in FIG. 15D for example, or in FIG. 16D in a similar way have the same advantages generally, the main distinction lying in how these locking means (3) are retained in the implant (2) as detailed hereafter. However it will be noted that in FIG. 14G, it is shown that the rod includes two flats, while FIGS. 15F and 16F do not clearly show the presence of a second flat. This potential difference expresses the optional presence of a withdrawal abutment surface and of an advance abutment surface, as detailed later on. Nevertheless it is understood that a notch may be provided on the anchor, comprising two surfaces (141, 142) for opposing the movements of the anchor in both directions. In the examples of FIGS. 18D, 18E and 18F, one resorts to a locking means (3) for each anchor (1) but the proposed layout nevertheless gives the possibility of avoiding weakening of the implant (2), notably by means of an advantageous position and/or orientation of the locking means (3). In these examples, two locking means (3) are provided, formed with two rods substantially parallel to each other and housed in oblique conduits positioned not parallel to the horizontal plane but perpendicularly to the antero-posterior axis of the implant. Although the advantage of a single locking means (3) is lost in this type of embodiment, it nevertheless provides another advantage in allowing easier ablation of the anchors, for example as detailed elsewhere in the present application. On the other hand, these examples of FIG. 18 address the problem of weakness by a substantial distance between the posterior end of the implant and the locking means (3), but this type of solution may further be enhanced by providing locking means (3), abutment and additional conduits which are not parallel, such as for example in the embodiments visible in FIGS. 19C and 19D. Indeed, in these embodiments, the rods forming the locking means (3) as well as their respective complementary conduit in the implant, are oriented obliquely relative to the vertical or horizontal axis, but also obliquely relative to the antero-posterior axis of the implant, so that the amount of material which separates these conduits and the rods is greater than that of the embodiments of FIG. 18, except at the portion where they intersect. Moreover it will be noted that this portion where both locking means intersect may be central (for example mediolateral, as illustrated) and that it is possible, for example in the case of an intersomatic cage like in this example, that the intersection is made at a central cavity of the cage, as for example visible in FIG. 19C or, more generally, at an edge of the implant, so that the latter is not too weakened by this intersection of the rods. Further, FIGS. 18 and 19 clearly show that the anchor has a notch forming the abutment (14) of the anchor which provides locking in the direction of withdrawal and advance. Although no flat is shown in FIGS. 18 and 19, it is possible to provide one like in other embodiments or to provide rods with a non-cylindrical section, but it may be useful to have a cylindrical rod without any flat for limiting any friction between the anchor and the locking means (3), facilitating the manufacturing of the implant and avoiding the requirement of observing any particular orientation upon assembly.

Figure 26A:
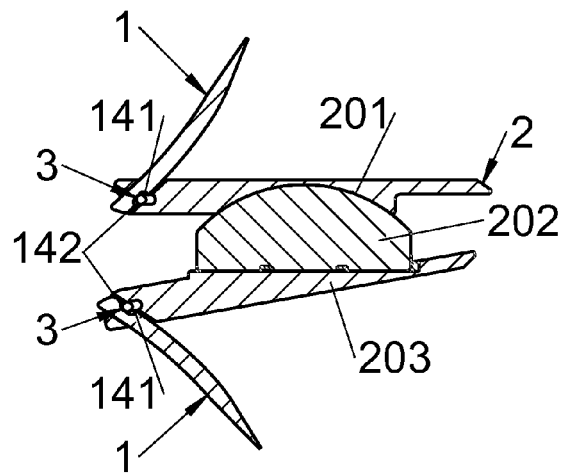
FIGS. 26B and 26A respectively illustrate a profile view and a sectional view along the sectional plane 26A-26A of FIG. 26B, of an intervertebral disc prosthesis according to certain embodiments, FIGS. 26C and 26D respectively illustrate a perspective view of an attachment device and a bottom view of an upper plate of an intervertebral disc prosthesis according to a first alternative embodiment and FIGS. 26E and 26F respectively illustrate a respective view of an attachment device and a bottom view of an upper plate of an intervertebral disc prosthesis according to a second alternative embodiment.
Figure 26B:
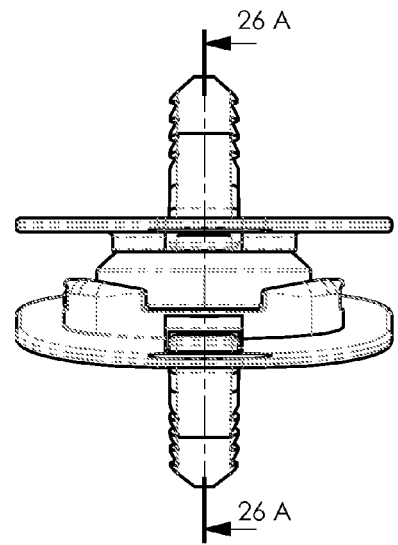
Figure 26C:
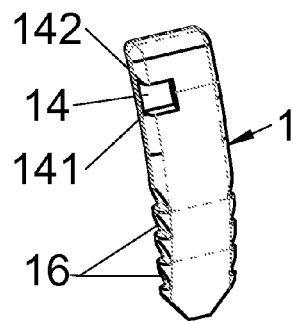
Figure 26D:
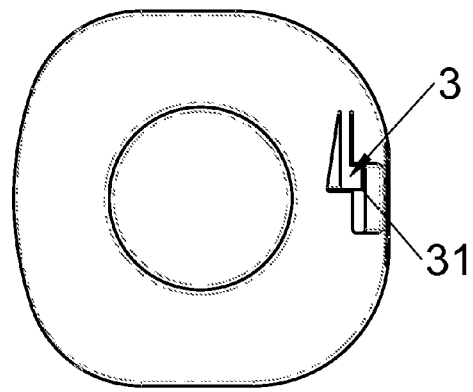
Figure 26E:
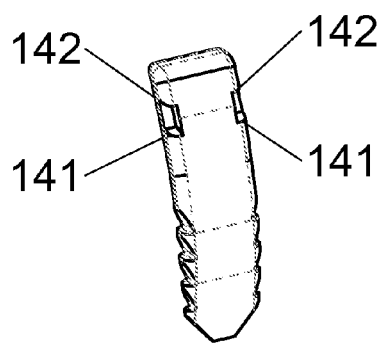
Figure 26F:
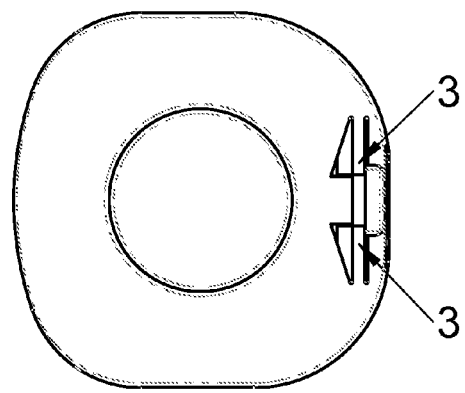

As explained above in the present application, the locking means (3) may be secured to the implant (attached therein or made in one piece with the implant, such as for example illustrated in FIGS. 26D and 26F) but it may also be distinct and housed in the implant. Nevertheless, a locking means housed in the implant is generally useful, as explained in the present application, since the housing and the walls of the implant which surround the bolt (3) prevent it from having degrees of freedom other than in the axis of its displacement for letting through the anchor for an elastic locking function. Thus, in these embodiments where the implant is housed and only has one degree of freedom, it is not only by its dimensions parallel to the insertion axis of the anchor that it retains the latter, but also by the surfaces of the implant itself against which it will be firmly applied for opposing the movement of the anchor in the longitudinal axis of the latter. Thus, it is seen for example in FIG. 26A that, even in the case of intervertebral disc prostheses (or osteosynthesis plates) a bolt housed in the thickness of the plate (or of the osteosynthesis plate) is useful, but flexible tabs which will not be retained may be used, for example like in FIGS. 26D and 26F. Thus a housing might be used if the thickness of the plates of the prosthesis or of the osteosynthesis plate allows this.

Generally, the various layout possibilities of the bolt (3) in the implant (2) are designated here by the fact that the locking means (3) is retained in a housing of the implant (2) (generally oriented along a direction not parallel to the axis of insertion of the anchoring device—or to the antero-posterior axis of the implant, also used as a reference even if they do not generally coincide). The locking means may be retained in the implant simply because it is housed there in a housing from which it cannot escape or because it is retained therein by specific means. Thus, in certain embodiments, the locking means (3) is retained in the implant (2) by at least one retention means (25, 32). Such retention means (32, 25) often prevent the movement of the locking means, such as of the abutment (31), generally in the direction of insertion and/or withdrawal of the anchoring device (1). Such a retention means (32, 25) may be obtained by the fact that at least one portion of the locking means (3) is positioned inside a housing in the implant (2), for example a housing avoiding any movement in a direction jeopardizing the locking of the anchor in the implant, or even by the fact that it is secured to the implant (formed in one piece in the implant or attached so that it is fixed relative to the implant). Nevertheless, various possibilities are contemplated, such as for example those detailed in the present application and typically it is only important that the locking means cannot move generally in the direction of the insertion and/or the withdrawal of the anchor, so that the latter is properly locked relative to the implant. Further, in certain embodiments, the retention means (32, 25) are configured so that the locking means (3) is removable. In certain embodiments, the retention means (32, 25) are formed with catches (32) or other type of raised portions or rough portions on at least one surface of the locking means (3) in order to be anchored in the walls of a housing of the implant (2) into which the locking means (3) is inserted. For example, the locking means (3) illustrated in FIG. 1D has catches intended to act against the movement of the locking means (3) in the direction for withdrawing the anchor and/or in the direction for withdrawing the locking means (3) from its housing or conduit in the implant. Also, in the example of FIG. 18B, the locking means is forcibly fitted into a housing of the implant, by a retaining portion (32). For example, the retention exerted by this portion may for example be improved by providing that is of an identical size with that of its housing, or even slightly larger so that it may be forcibly fitted in the inside. It is also possible, among other options, to provide a thread, for example mating a tapping in the housing of the implant or simply a threading or any type of raised or rough portions which allow insertion into the housing and will be sufficient for exerting effective retention. In certain embodiments, the retention means (32, 25) are formed by a housing (32) in the locking means (3) intended to receive a stick (25) inserted into this housing (32) through a conduit (250) of the spinal implant (2). This retention by a mechanism of the pin-mortise type may naturally find many embodiments. For example, in certain embodiments, the retention means (32, 25) are formed by a recess (32) in the locking means (3) intended to receive a pin (25) or a staple (25) inserted through the spinal implant (2) in order to cooperate with this recess (32). For example FIGS. 2D, 3F, 10G, 14B, 14E, 14F, 15C, 15D, 16C, 17B, 17G show various non-exhaustive alternatives (such as pins, staples, sticks or other simple and functional structures) of retention means (32, 25) giving the possibility of avoiding that the locking means (3) moves out of the implant. In the case of locking means (3) comprising a rod housed in the implant as detailed above and with reference to FIGS. 18D, 18E and 18F, but also in other embodiments such as those shown for example in FIGS. 4C, 6A and 6C, it is intended to take advantage of the simplicity of the layout for providing a simple and efficient solution for retaining the locking means (3) in the implant (2). Indeed, a shoulder or a butt located at one end, or near an end of the body of the locking means (for example a butt (32) at the end of the rod in FIG. 18I) allows the latter to be retained in the implant (2). For example, in FIGS. 4C, 6A, 6C and 6E, the locking means (3) may be inserted into its housing through a conduit of the implant and it is therefore possible to provide, for example at (or near) its end opposite to the one which retains the anchors, a butt or tabs (or any equivalent type of abutment) so as to bear upon the inlet of this conduit, such as for example illustrated in FIG. 6E, or for being housed in a housing in the walls of this conduit, as for example illustrated in FIG. 6C. Further, in the case of such tabs (32), it is possible to provide a flexible portion, for example obtained by means of a cutout forming at least two branches bearing the retaining tabs (32). This type of alternative gives the possibility of inserting the locking means in this conduit from the end of the conduit opening at the anchors (1). Further, in the case of tabs being housed in the recesses of the walls of the conduit, such as for example in FIG. 6E, the layout gives the possibility that the locking means (3) be retained in the direction of its withdrawal and in the direction of its advance into the conduit, which may be useful in the case of FIGS. 6B, 6C and 6E since the locking means (3) include abutment surfaces (311, 312) for opposing the withdrawal of the anchor (1) but also for limiting the advance of the latter in the implant (2). It is therefore understood that various layouts of the retention means (25, 32) are provided in the present application for avoiding movement of the locking means (3) in diverse directions and also guaranteeing the locking of the anchor (1) which must not move in the direction of the advance (penetration) and/or in the direction of the withdrawal. Generally, retention (25, 32) of the locking means (3) is therefore preferably provided depending on the blocking which it is intended to exert on the anchor (1).

In certain useful embodiments, such as for example illustrated in FIG. 18H, the retention means (32, 25) are formed by at least one shoulder (32) of the locking means (3) intended to abut against the anchoring device (1), on either side of its abutment (14), so that the anchoring device (1) prevents movement of the locking means (3) in the spinal implant (2). This type of retention means may have the additional advantage of not requiring that an additional conduit or one wider than the one required for inserting the locking means (3) in the implant be provided. Further, in the example of FIG. 18H, the rod forming the locking means (3) in fact includes two shoulders (32) since the abutment (31) is formed by thinning of the rod (preferably to a thickness which is possible if this is allowed by the conduit). This alternative embodiment may have the additional advantage of allowing the rod to be retained in its conduit once that the anchor (1) has been locked by this thinned portion forming the abutment (31), by providing that the notch (14) of the anchor has dimensions complementary to the thinned portion and is smaller than the two thicker portions on either side of the abutment. Thus, the rod may be retained in both directions along its conduit. This may have the additional advantage of facilitating machining of the parts since it is then possible to insert the locking means (3) in its conduit from a face of the implant, while providing the housing for its displacement during the passing of the anchor, without requiring a larger conduit on the other side for its insertion, such as for example required in the case of FIG. 18E. In certain alternative embodiments, the retention means (25, 32) may also include a threading on the periphery of the locking means (3), for example complementary to a tapping in the implant as explained above, for retaining the locking means (3). Nevertheless it will be noted that according to the orientation of the locking means (3) relative to the anteroposterior axis of the implant, it is possible not to provide any retention means (25, 32) to the locking means (3), or it is sufficient that it is forcibly fitted or hooked up in a conduit, since it may not be likely to move out of the implant, the retention means then being formed by the fitting or the hooking-up, such as for example in FIG. 5E, 7G or 9F. In the example of the useful embodiments of the type of those of FIG. 19D, it is possible to provide such a retention means (threading, roughness, fitting) (32) of the locking means (3). Nevertheless, in such examples, there may be a lesser need for a threading or rough or raised portions thanks to the path of the locking rod (3) relative to the passage of the anchors. Indeed, the locking rod of an anchor may for example partly cross the passage of the other anchor, while slightly jutting out inside, so that this other anchor, once it is inserted in its passage, bears against the locking rod and thereby blocks it in its conduit, as for example visible in FIG. 19D. On the other hand, in embodiments where two rods intersect, it is possible to provide that the intersection is made on a portion where the conduits of both rods are not yet flared (the flaring allows flexure of the rods), and to then provide a crossed path where both rods come into contact with each other through a retention portion (32) for example formed by a notch with a shape mating a portion of the section of the other rod (similar to the notches (32) of FIGS. 14G and 15F, but the function of the retaining pin or peg (25) here being fulfilled by the locking rod of the other anchor).

Spinal Implant (Rachidian/Intervertebral Implant):

In certain embodiments, the spinal implant (2) is formed with at least one intersomatic cage, comprising a body forming a means for maintaining the height of the intervertebral space. This body includes at least one passage crossing it from a peripheral wall to a vertebral contact surface of the cage. Examples of such embodiments are illustrated on many figures of the present application, except for those of FIGS. 26A, 26B, 26D, and 26F. Many features of such cages are known from the prior art and do not therefore need to be detailed, but it is useful to generally describe some useful embodiments of the passage and its shape, as well as the layouts of the locking means.

In certain embodiments, the spinal implant (2) is formed with at least one intervertebral disc prosthesis, comprising at least two plates jointed together by at least one curved surface. Typically, such a curved surface is generally present on one of the plates and generally cooperates with another curved surface either present on the other plate, or on a moveable core relative to at least one of the plates. At least one of both plates includes at least one passage crossing it, from a peripheral edge of the plate (or from an internal face of the prosthesis), to a vertebral contact surface of the prosthesis. Examples of such embodiments are illustrated in FIGS. 26A, 26B, 26D, and 26F.

In certain embodiments (not shown), the spinal implant (2) is formed with at least one osteosynthesis plate crossed by the passage from an outer face to a vertebral contact face of the osteosynthesis plate. In certain embodiments (not shown), the spinal implant (2) is formed with at least one corporectomy cage, for example comprising modular elements assembled together. Typically, at least one portion of these modular elements is intended to be in contact with the vertebrae and therefore include passages for the anchors and the locking devices according to various embodiments of the present disclosure.

In certain embodiments, for example those wherein the implant is a prosthesis or a plate, the locking means (3) may be directly machined in the thickness of said vertebral plate or of said plate. Indeed, the vertebral plates and the plates are often in solid materials, such as for example titanium and it is therefore may be useful to provide the locking means directly in the material of these elements.

Figure 24A:
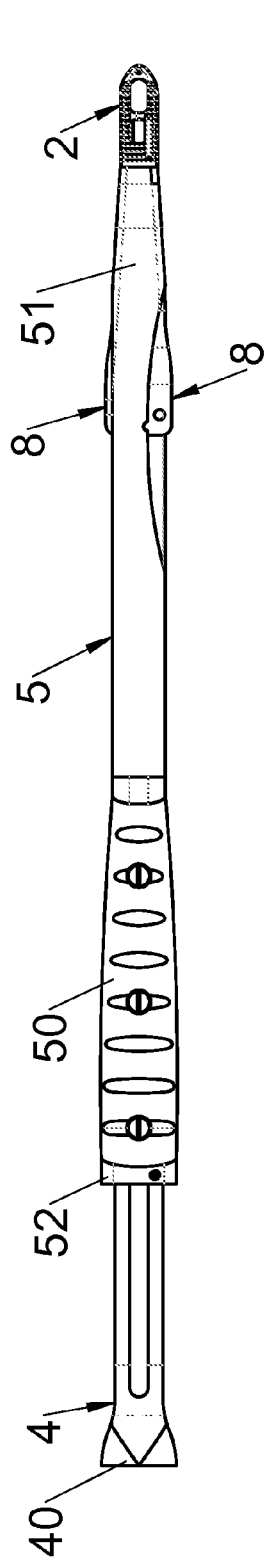
FIGS. 24A, 24B and 24C respectively illustrate a top view, a profile view and a sectional view along the sectional plane 24C-24C of FIG. 24B, of an implant-holder bearing an implant crossed by attachment devices by means of an impactor according to certain embodiments.
Figure 24B:
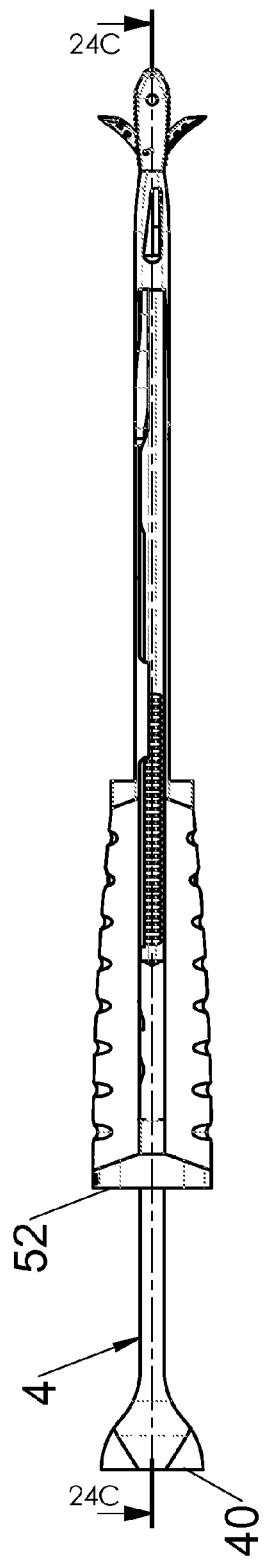
Figure 24C:
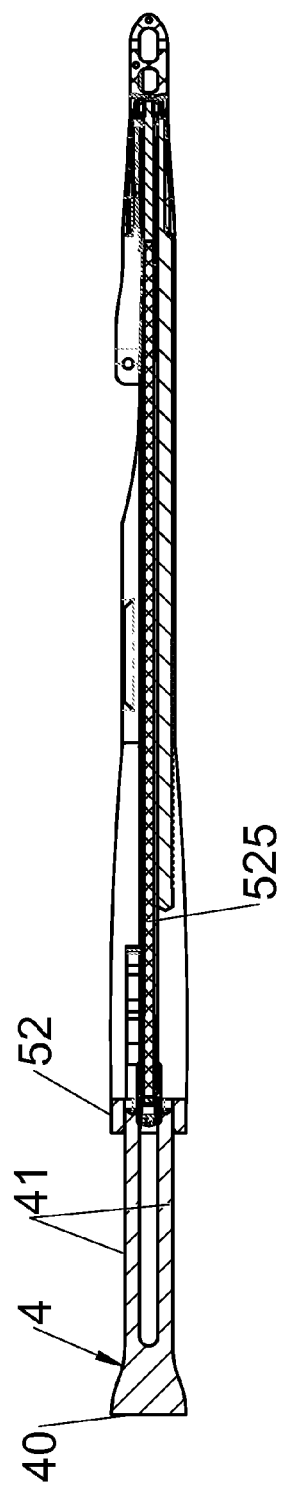
Figure 25A:
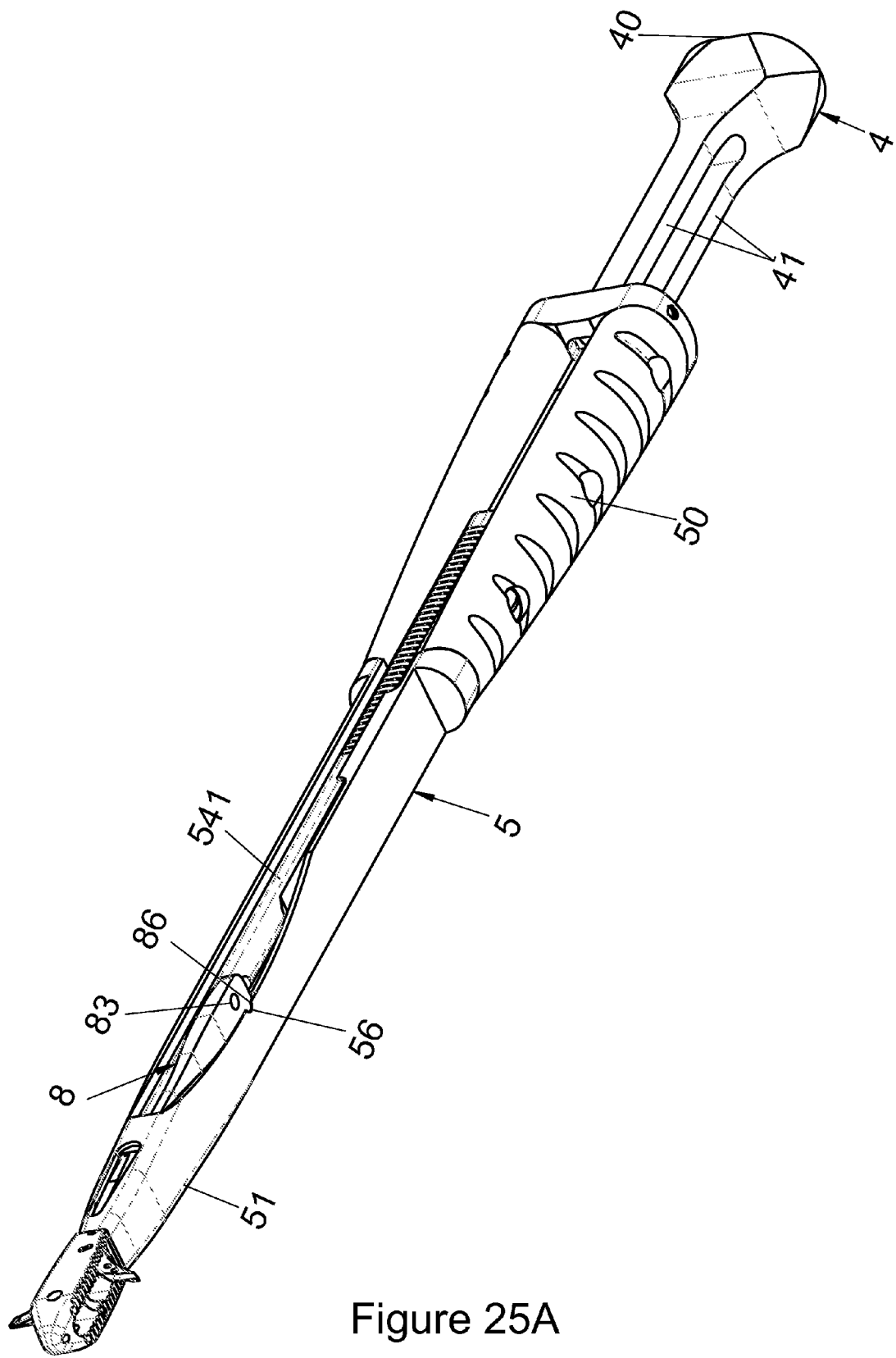
FIG. 25A illustrates a perspective view of an implant-holder bearing an implant crossed by attachment devices by means of an impactor according to certain embodiments.

In certain embodiments, the spinal implant (2) includes at least one hooking-up means (26, 27) for it to be grasped by a surgical instrument. It will be noted that the spinal implant (for example an intersomatic cage) includes at least one hooking-up means (26, 27) for its grasping by means of an instrument, such as an implant-holder (5) for example. This grasping may be achieved by cooperation of these hooking-up means (26, 27) of the implant (2) with at least one means (525) for grasping an implant which equips the instrument. In certain embodiments, the implant includes a single hooking-up means, such as for example a hole in one of its walls, for example the so-called posterior wall through which the anchor is inserted into the passage. This hole for example may be tapped in order to cooperate with a threading of the means (525) for grasping an implant, for example formed with a threaded rod, the screwing into the hole (26) of which being controlled for example by means of a knurl (52) of the instrument (FIG. 24C). In certain embodiments, the implant may include a second hooking-up means (27) such as for example illustrated in FIGS. 1B, 2B, 3B, 4B, 5B and 6B. This second means may for example be formed with a groove into which will be inserted a tongue of the instrument, or with a groove comprising a recess, such as for example visible in FIG. 5D, into which will be inserted a lug of the instrument. This type of double hooking-up means allows better grasping of the implant and provides a lever arm for pivoting the implant around the antero-posterior axis if need be. Nevertheless, in the present application, it is possible to take advantage of the layout of the anchors and of the implants by using preloaded anchors in the implant for obtaining this lever arm. Thus, a single hooking-up means may be provided since it is possible to use the anchors loaded in the instrument and at least partly engaged into the implant for stabilizing the implant and allowing possible rotation if need be.

Implantation

The present disclosure also relates to surgical instrumentation for implanting a spinal implant (2) according to various embodiments of this disclosure and others within the scope of the claims, and for attaching this implant (2) to at least one vertebra by at least one anchoring means (1) according to various embodiments of this disclosure and others within the scope of the claims. This instrumentation may, for example, comprise one or more of the following structures or other structures with similar function:

- an implant-holder (5) of elongated shape along a longitudinal axis extending between a first end, a so-called end for grasping the implant (2) and a second end, a so-called pusher, the grasping end including a head (51) provided at its end with at least one means (525) for grasping the implant (2), the head (51) being crossed by a longitudinal passage opening onto the implant (2) and capable of receiving said anchoring device (1).
- at least one impactor (4) of elongated shape along a longitudinal axis extending between both ends of the impactor, one of the ends at least comprising a branch (41) capable of penetrating into the implant-holder (5) for pushing directly or via another device (for example a rod inside the implant-holder and extending the branch of the impactor, as for example detailed hereafter), the posterior end of said anchoring device (1), while the other end of the impactor comprises a so-called impaction surface, laid out for receiving a thrust or an impact for having the anterior end of said anchoring device (1) penetrate into a vertebra through the passage of the implant (2),
- at least one guiding surface for the anchoring device (1) for guiding the sliding of the latter in the implant-holder (5) right through into the implant (2).

Illustrative and non-limiting examples of such instrumentation are illustrated in FIGS. 23A, 23B, 23C, 23D, 24A, 24B, 24C and 25A. These examples illustrate various exemplary elements in combination with each other, but it is clear that they may each form a particular element independently of each other and be claimed separately, notably as regards the loader (8), the impactor (4) or the implant-holder (5).

This instrumentation may include at least one means for actuating the locking means (3) for pushing back the locking means (3) during the insertion of said anchoring device (1) into the passage of the implant (2), via at least one means for accessing the locking means (3), for example a means for accessing the complementary abutments (14, 31) of the anchoring device (1) and of the locking device (3). Indeed, as explained earlier, provision is often made in many embodiments for accessing the locking means (3) in order to push back the abutments during the period for implanting the anchors, so as to facilitate implantation. Thus, in certain useful embodiments, the instrumentation includes at least one means for actuating the locking means (3). Typically, the means (525) for grasping an implant is configured for cooperating with at least one hooking-up means (26, 27) of said implant. This grasping means (525) may therefore for example be used as an actuation means if it is used as detailed in FIG. 21F and as explained above on the insertion of at least one pin into the hooking-up means (26) of the implant.

In certain embodiments, the instrumentation may include at least one retention means (84, FIG. 23C) capable of cooperating with said abutment (14) of the anchoring device (1) for retaining the latter in the implant-holder with actuation of the impactor (4).

In certain embodiments, the surgical instrumentation may include at least one loader (8) capable of sliding in the head of the impact holder (5) and provided with said guiding surface. In some of these embodiments, said retention means (84) is provided on these loaders (8). This type of loader (8) may include a housing or a cutout (85) forming a guide for impacting the anchors by guiding the passage of the branches of the impactor or of extender rods as described hereafter. Further, this loader may include a retention means (86) allowing it to be retained in the head of the implant-holder (5), as for example visible in FIG. 23A. In certain embodiments, the loader (8) may also include at least one hooking-up means (83) so as to be able to be manipulated, for example for sliding it in the head of the implant-holder (5), for engaging it therein or for extracting it for example.

In certain embodiments, the surgical instrumentation includes two loaders (8), each of them being, on the one hand, provided with a guiding surface, for example with a retention means (84) and on the other hand capable of sliding in the head of the implant-holder (5).

In some embodiments, the impactor (4) may include two branches (41) capable of pushing simultaneously two anchoring devices (1) loaded on two loaders (8) in the head of the implant-holder (5). The impactor (4) may have a shape of a tuning fork, for example, the two branches (41) of which are able to push simultaneously through the head of the implant-holder (5) both loaders (8) on which are loaded both anchoring devices (1). In certain alternatives, such as for example illustrated in FIG. 24B, the impactor may in fact push on extender rods slidably mounted inside the implant-holder and transmitting the thrust to the anchors (1).

In certain embodiments, the surgical instrumentation may include a tool (9) for withdrawal of the anchoring device comprising a hooking-up means (17) for one end (97) of the withdrawal tool (9) which is configured for hooking up the anchoring device (1), so that traction on the tool allows withdrawal of the latter from its passage in the implant. This tool may for example be configured for accessing the hooking-up means (17) of the anchoring device (1) via a means for accessing an implant (2) according to certain embodiments.

This disclosure also relates to a rachidian surgery system that may, for example, include at least one anchoring device (1) according to various embodiments of this disclosure and at least one spinal implant (2) according to various embodiments of this disclosure, at least one locking means (3) allowing said anchoring device (1) to be locked relative to the spinal implant (2) in order to ensure stabilization of the latter in a vertebra.

In certain embodiments, the system includes at least one instrument from the various implantation instrumentation embodiments of this disclosure.

The present application describes various technical characteristics and advantages with reference to the figures and/or to various embodiments. One skilled in the art will understand that the technical characteristics of a given embodiment may in fact be combined with characteristics of another embodiment unless the opposite is explicitly mentioned or it is obvious that these characteristics are incompatible. Further, the technical characteristics described in a given embodiment may be isolated from the other characteristics of this embodiment unless the opposite is explicitly mentioned.

After appreciating this disclosure, it should be obvious for those skilled in the art that other embodiments in many other specific forms may be configured without departing from the scope of the claims. Therefore, the present embodiments should be considered as illustrations, which may be modified without departing from the scope of the appended claims, and this disclosure should not be limited to the details given above.

The invention claimed is:

1. A combination for treating a spine, the combination comprising:
    an anchor comprising
        an anterior end configured for penetration of a vertebral surface,
        a posterior end configured for impacting the anchor into a vertebra,
        a longitudinal axis extending between the anterior end and the posterior end,
        an elongated plate-like body disposed along the longitudinal axis, the plate-like body having a width and a height defined by a first cross section of the plate-like body oriented generally perpendicular to the longitudinal axis, and
        a lock abutment surface disposed between the anterior end and the posterior end and oriented angularly to the longitudinal axis; and
    a spinal implant comprising
        an access surface configured to be accessible with the implant when the implant is implanted in a spine,
        a vertebral contact surface,
        a passage extending from the access surface to the vertebral contact surface defining an insertion axis for the anchor, the passage having a width and a height defined by a second cross section of the passage oriented generally perpendicular to the insertion axis, and
        a lock comprising
            an anchor abutment surface disposable along the passage and orientable angularly to the insertion axis, the anchor abutment surface configured to operatively mate with the lock abutment surface of the anchor, and a flexible portion having a resting position defining a first anchor abutment surface position in which the anchor abutment surface is extendable into the passage and engagable with the lock abutment surface of the anchor, and a second anchor abutment surface position in which the anchor abutment surface is retracted from the passage to permit passage of the anchor through the passage past the lock.

2. The combination of claim 1, in which first cross section and the second cross section have complementary shapes and dimensions.

3. The combination of claim 1, in which the first cross section defines an L shape.

4. The combination of claim 1, in which the first cross section defines a V shape.

5. The combination of claim 1, in which the first cross section defines a T shape.

6. The combination of claim 1, in which the first cross section defines a U shape.

7. The combination of claim 1, in which the plate-like body has a curvilinear shape along the longitudinal axis.

8. The combination of claim 7, in which the passage has a curvilinear shape along the insertion axis complementary to the curvilinear shape of the plate-like body.

9. The combination of claim 7, in which the passage has a rectilinear shape along the insertion axis complementary to the curvilinear shape of the plate-like body.

10. The combination of claim 1, in which the anterior end of the anchor includes a notch configured to facilitate penetration of the anterior end into a vertebral surface.

11. The combination of claim 1, in which the plate-like body has an opening configured to allow bone ingrowth.

12. The combination of claim 1, in which the lock has a body extending into a recess of the spinal implant oriented transversely to the insertion axis.

13. The combination of claim 1, in which the lock has a body extending into a recess of the spinal implant oriented angularly to the passage.

14. The combination of claim 1, in which movement of the anchor abutment surface from the first anchor abutment surface position to the second anchor abutment surface position occurs at least in part by torsion of at least a portion of the lock.

15. A system comprising the combination of claim 1 and a surgical instrument for implanting the spinal implant and attaching the spinal implant to a vertebra with the anchor, the surgical instrument comprising an implant holder elongated along a longitudinal axis extending between a grasping end and a pushing end and comprising a head having an implant connector, an implant facing surface, and a passage extending through the head and opening on the implant facing surface; an impactor elongated along a longitudinal axis extending between a posterior end and an anterior end of the impactor, the anterior end comprising a branch disposable into the implant holder passage; an anchor guiding surface configured to guide the anchor through the head and into the spinal implant; and a release configured to unlock the anchor from the spinal implant.

16. The system of claim 15, further comprising a first loader slidable in the head on which the anchor guiding surface is disposed.

17. The system of claim 16, further comprising a second loader, with the impactor comprising two branches configured to push the first loader and second loader simultaneously.

18. The system of claim 15, further comprising an anchor extraction tool configured with a release configured to unlock the anchor from the spinal implant.

19. A method for treating a spine, the method comprising:
obtaining the system of claim 15;
flexing the flexible portion to place the anchor abutment surface in the second anchor abutment surface position;
inserting the anchor into the spinal implant while the anchor abutment surface is in the second anchor abutment surface position and the anterior end of the anchor penetrates a vertebral surface and the lock abutment surface is engagable with the anchor abutment surface; and
extending the anchor abutment surface into the second anchor abutment surface position to engage the anchor abutment surface with the lock abutment surface of the anchor.

20. The method of claim 19, in which the step of flexing the flexible portion and the step of inserting the anchor into the spinal implant are performed at least partly concurrently.

* * * * *